United States Patent
Muse et al.

(10) Patent No.: US 11,746,181 B2
(45) Date of Patent: Sep. 5, 2023

(54) ALCOHOL-RESISTANT SILICONIZED POLYCARBONATE POLYURETHANES AND MEDICAL DEVICES INCORPORATING THE SAME

(71) Applicants: Jay Allen Muse, Salt Lake City, UT (US); Nathaniel J. Fredin, Layton, UT (US); Sriram Venkataramani, Draper, UT (US)

(72) Inventors: Jay Allen Muse, Salt Lake City, UT (US); Nathaniel J. Fredin, Layton, UT (US); Sriram Venkataramani, Draper, UT (US)

(73) Assignee: Piper Access, LLC, Salt Lake City, UT (US)

( * ) Notice: Subject to any disclaimer, the term of this patent is extended or adjusted under 35 U.S.C. 154(b) by 1263 days.

(21) Appl. No.: 16/195,724

(22) Filed: Nov. 19, 2018

(65) Prior Publication Data

US 2019/0153147 A1    May 23, 2019

Related U.S. Application Data

(63) Continuation of application No. PCT/US2018/061708, filed on Nov. 17, 2018.

(60) Provisional application No. 62/617,051, filed on Jan. 12, 2018, provisional application No. 62/587,761, filed on Nov. 17, 2017.

(51) Int. Cl.
| | |
|---|---|
| A61L 29/06 | (2006.01) |
| A61L 29/16 | (2006.01) |
| A61L 29/18 | (2006.01) |
| A61M 25/00 | (2006.01) |
| A61M 25/01 | (2006.01) |
| C08G 18/32 | (2006.01) |
| C08G 18/40 | (2006.01) |
| C08G 18/44 | (2006.01) |
| C08G 18/61 | (2006.01) |
| C08G 18/65 | (2006.01) |
| C08G 18/66 | (2006.01) |
| C08G 18/76 | (2006.01) |
| C08K 3/30 | (2006.01) |

(52) U.S. Cl.
CPC .......... *C08G 18/4009* (2013.01); *A61L 29/06* (2013.01); *A61L 29/16* (2013.01); *A61L 29/18* (2013.01); *A61M 25/0054* (2013.01); *A61M 25/0105* (2013.01); *C08G 18/3206* (2013.01); *C08G 18/44* (2013.01); *C08G 18/61* (2013.01); *C08G 18/6511* (2013.01); *C08G 18/664* (2013.01); *C08G 18/7664* (2013.01); *C08G 18/7671* (2013.01); *C08K 3/30* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 5,133,742 A | | 7/1992 | Pinchuk |
| 5,430,121 A | * | 7/1995 | Pudleiner ........... C08G 18/4009 525/464 |
| 6,313,254 B1 | * | 11/2001 | Meijs ................. C08G 18/6511 528/26 |
| 6,420,452 B1 | | 7/2002 | Gunatillake et al. |
| 6,437,073 B1 | | 8/2002 | Gunatillake et al. |
| 6,627,724 B2 | * | 9/2003 | Meijs ...................... A61L 15/26 528/26 |
| 7,026,423 B2 | | 4/2006 | Gunatillake et al. |
| 7,494,665 B1 | | 2/2009 | Ding et al. |
| 7,618,411 B2 | | 11/2009 | Appling |
| 7,772,296 B2 | | 8/2010 | Garey, Jr. et al. |
| 8,242,189 B2 | * | 8/2012 | Rega ...................... C08L 83/10 524/413 |
| 8,623,986 B2 | | 1/2014 | Mehrabi et al. |
| 8,674,035 B2 | * | 3/2014 | Padsalgikar ........... C08G 18/10 528/25 |
| 9,175,130 B2 | | 11/2015 | Padsalgikar |
| 9,512,261 B2 | * | 12/2016 | Padsalgikar ............ A61L 27/50 |
| 9,580,558 B2 | | 2/2017 | Ding et al. |
| 2003/0018156 A1 | | 1/2003 | Meijs et al. |
| 2003/0153983 A1 | | 8/2003 | Miller et al. |
| 2008/0051759 A1 | | 2/2008 | Murphy et al. |
| 2009/0182111 A1 | | 7/2009 | Padsalgikar |
| 2009/0326560 A1 | | 12/2009 | Lampropoulos et al. |
| 2010/0256546 A1 | | 10/2010 | Davis et al. |
| 2014/0276650 A1 | * | 9/2014 | Muse ...................... A61L 29/18 604/533 |
| 2017/0210844 A1 | | 7/2017 | Padsalgikar |

FOREIGN PATENT DOCUMENTS

| | | |
|---|---|---|
| JP | 2001-500912 A | 1/2001 |
| JP | 2008-101194 A | 5/2008 |

(Continued)

OTHER PUBLICATIONS

International Searching Authority, International Search Report in International Application No. PCT/US2018/061708, dated Feb. 1, 2019, 2 pages.

(Continued)

*Primary Examiner* — Melissa A Rioja
(74) *Attorney, Agent, or Firm* — Med Venture Management, LLC; Daniel C. Higgs

(57) ABSTRACT

An alcohol-resistant siliconized polycarbonate polyurethane can include a soft segment and a hard segment. The soft segment can include a polycarbonate polyol and a polysiloxane, which can be present in an amount less than the polycarbonate polyol. The hard segment can include an isocyanate and a chain extender. Peripherally inserted central catheter (PICC) devices can include one or more components that are at least partially formed from one or more formulations of the siliconized polycarbonate polyurethane catheter. The PICC devices can withstand alcohol locking, and can be power injectable both before and after alcohol locking events.

24 Claims, 16 Drawing Sheets

(56) References Cited

FOREIGN PATENT DOCUMENTS

| JP | 2009-531474 A | 9/2009 |
| JP | 2016-199702 A | 12/2016 |
| WO | 2019/099964 A1 | 5/2019 |

OTHER PUBLICATIONS

International Searching Authority, Written Opinion in International Application No. PCT/US2018/061708, dated Feb. 1, 2019, 3 pages.
European Patent Office, Extended European Search Report in European Patent Application No. 18878620.6, dated Jul. 19, 2021, 6 pages.
Japan Patent Office, Notice of Reasons for Rejection in Japanese Patent Application No. 2020-545053, dated Nov. 2, 2022, 7 pages.
Xu et al., Proteins, Platelets, and Blood Coagulation at Biomaterial Interfaces (published in final edited form as Colloids Surf B Biointerfaces), PubMed Central®, Aug. 26, 2016, 54 pages.
Yu et al., Crosslinked waterborne polyurethane with high waterproof performance, Polymer Chemistry, May 2, 2016, pp. 3913-3922, vol. 7, issue 23.
Biomerics, Introducing Prolix™ Medical Fluid Management Tubing, published no later than Mar. 7, 2017, 10 pages.
Biomerics, Quadra™ Family of Medical Polyurethanes, published no later than Mar. 7, 2017, 6 pages.
Advansource Biomaterials, ChronoSil®, available at http://www.advbiomaterials.com/products/polycarbonate/chronosil.html, copy obtained on Sep. 13, 2017, 2 pages.
DSM PTG, CarboSil® thermoplastic silicone polycarbonate-urethane, Oct. 2009, 2 pages.
DSM, CarboSil® Thermoplastic Silicone Polycarbonate Polyurethane (TSPCU), 2012, 2 pages.
Plasticseurope, Eco-profiles of the European Plastics Industry: POLYOLS, Mar. 2005, 19 pages.

* cited by examiner

ALCOHOL-RESISTANT SILICONIZED POLYCARBONATE POLYURETHANES AND MEDICAL DEVICES INCORPORATING THE SAME

CROSS REFERENCE TO RELATED APPLICATIONS

This application claims the benefit under 35 U.S.C. § 119(e) of U.S. Provisional Patent Application No. 62/587,761, titled ALCOHOL-RESISTANT SILICONIZED POLYCARBONATE POLYURETHANES AND MEDICAL DEVICES INCORPORATING THE SAME, filed on Nov. 17, 2017, and U.S. Provisional Patent Application No. 62/617,051, titled ALCOHOL-RESISTANT SILICONIZED POLYCARBONATE POLYURETHANES AND MEDICAL DEVICES INCORPORATING THE SAME, filed on Jan. 12, 2018; further, pursuant to 35 U.S.C. §§ 120 and 365(c), this application is a continuation of prior International Application No. PCT/US2018/061708, which has an international filing date of Nov. 17, 2018, and is titled ALCOHOL-RESISTANT SILICONIZED POLYCARBONATE POLYURETHANES AND MEDICAL DEVICES INCORPORATING THE SAME, which International Application claims the benefit of U.S. Provisional Patent Application No. 62/587,761, titled ALCOHOL-RESISTANT SILICONIZED POLYCARBONATE POLYURETHANES AND MEDICAL DEVICES INCORPORATING THE SAME, filed on Nov. 17, 2017, and U.S. Provisional Patent Application No. 62/617,051, titled ALCOHOL-RESISTANT SILICONIZED POLYCARBONATE POLYURETHANES AND MEDICAL DEVICES INCORPORATING THE SAME, filed on Jan. 12, 2018; the entire contents of each of the foregoing applications are hereby incorporated by reference herein.

TECHNICAL FIELD

Certain embodiments described herein relate generally to polyurethanes, and relate more particularly to polycarbonate polyurethanes. Further embodiments relate generally to medical devices, such as, for example, catheters, that incorporate such polycarbonate polyurethanes.

BACKGROUND

Polyurethane is a versatile plastic material that can be adapted for a variety of applications. For example, polyurethanes have been employed in insulation panels, gaskets, hoses, tires, wheels, synthetic fibers, surface coatings, furniture, footwear, adhesives, medical devices, and a variety of other materials and devices. Typically, polyurethanes are formed by reacting a polyol with a diisocyanate or other polyisocyanate in the presence of suitable catalysts, additives, or the like. Due to the variety of starting materials that can be used, a broad spectrum of polyurethane materials can be prepared to meet the needs of a variety of specific applications.

Polycarbonate polyurethanes, or polyurethanes formed with polycarbonate polyols, may be used in a variety of applications. However, known polycarbonate polyurethanes suffer from various drawbacks or limitations when used in certain medical devices, such as certain catheters. Embodiments disclosed herein overcome shortcomings of prior polycarbonate polyurethanes in at least this regard, as will be apparent from the discussion that follows.

BRIEF DESCRIPTION OF THE DRAWINGS

The written disclosure herein describes illustrative embodiments that are non-limiting and non-exhaustive. Reference is made to certain of such illustrative embodiments that are depicted or otherwise described in the figures, in which.

DETAILED DESCRIPTION

Figure 1:
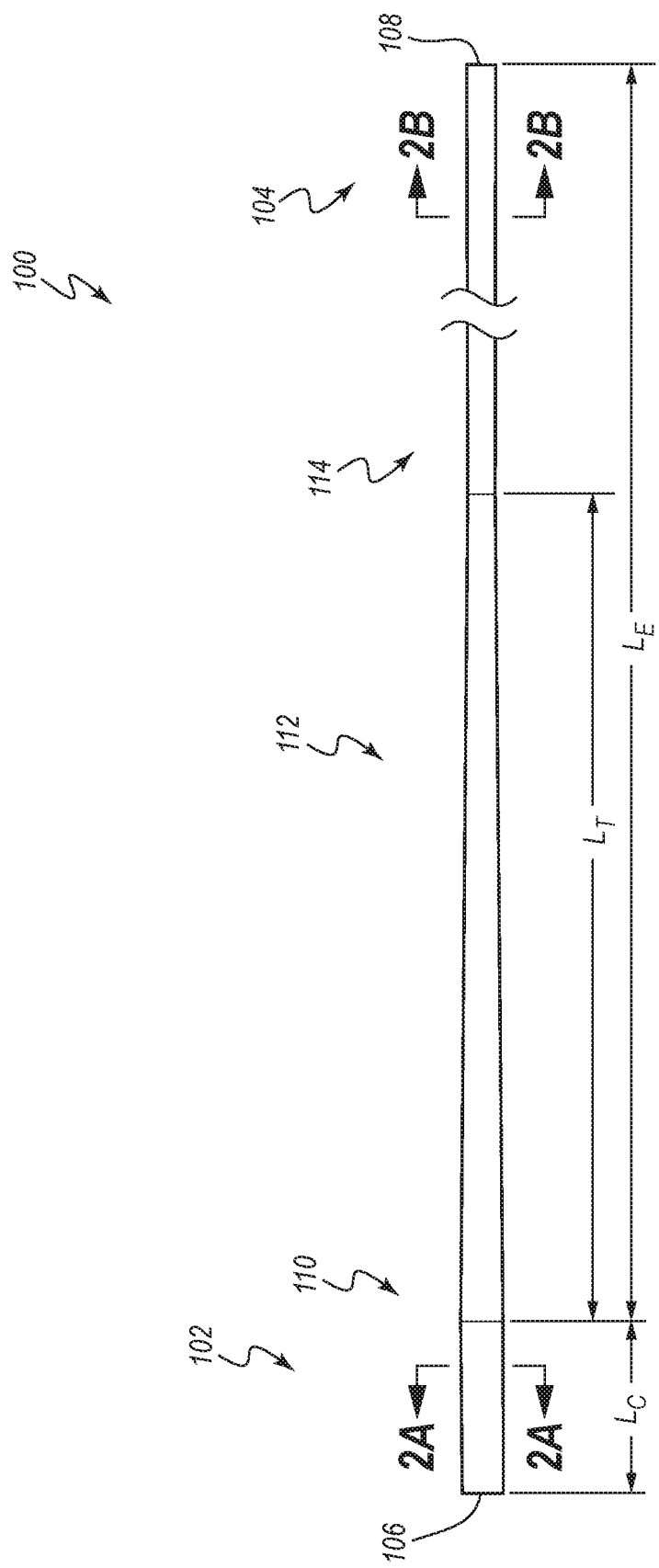
FIG. 1 is an illustrative embodiment of a catheter shaft that may suitably be formed, at least in part, from any of various embodiments of siliconized polycarbonate polyurethanes disclosed herein.

The current disclosure relates generally to alcohol-resistant polymers, which may be of particular use in medical applications. More specifically, the current disclosure relates to alcohol-resistant siliconized polycarbonate polyurethanes, or polycarbonate polyurethanes that include polysiloxane components, which may be formulated for advantageous use in medical devices such as, for example, catheters. The siliconized polycarbonate polyurethanes may be referred to as siliconized polycarbonate polyurethanes; silicone-containing or silicone-bearing polycarbonate polyurethanes; polysiloxane, polycarbonate polyurethanes; or polyurethane-siloxane copolymers, with each such term being intended to identify a polycarbonate polyurethane that includes a polysiloxane component. In particular, these terms designate a polyurethane that includes a soft segment into which each of the polycarbonate and the polysiloxane components are chemically incorporated.

In some embodiments, catheters, such as central venous catheters (CVCs) or, more particularly, peripherally inserted central catheters (PICCs), comprise one or more components that are each at least partially formed of one or more formulations of the alcohol-resistant siliconized polycarbonate polyurethane. For example, in some embodiments, a PICC shaft that defines at least one lumen comprises a formulation of the siliconized polycarbonate polyurethane that enables the lumen of the shaft to be disinfected or sterilized, cleared, or otherwise treated via alcohol locking, which may also be referred to as ethanol locking, in which alcohol (ethanol, typically) is retained within the lumen for a treatment or exposure period (e.g., at least one hour) to achieve the specified treatment or objective (e.g., disinfection and/or occlusion removal). In various embodiments, the siliconized polycarbonate polyurethane can substantially fully recover from the alcohol lock within a recovery period (e.g., no less than one hour), which may be sufficiently short to permit alcohol locking and subsequent power injection of the catheter to take place in, for example, outpatient clinical settings. In various embodiments, the PICC device may be power injectable both before and after the alcohol lock (e.g., after a specified recovery period). In further embodiments, the PICC device may be suitable for use as a pediatric PICC or other catheter, including for very small patients (e.g., in neonates weighing down to 2.3 kg).

In some embodiments, a PICC device includes a shaft that includes a first formulation of siliconized polycarbonate polyurethane according to the present disclosure, one or more extension tubes that include a second formulation of siliconized polycarbonate polyurethane according to the present disclosure, and a junction hub that includes a third formulation of siliconized polycarbonate polyurethane according to the present disclosure. One or more of the first, second, and third formulations may be the same as or different from one or more of the remainder of the first, second, and third formulations. The PICC can be substantially free from leaks or bursts during normal use (for example, at relatively low injection or aspiration pressures, after multiple openings and closings of the extension tubes via clamps, etc.) and/or during power injection, both before and after an alcohol lock event. Numerous other or further embodiments and advantages are also disclosed.

I. Definitions and Disclosure Conventions

As used herein, "medical catheter" or "catheter" each refers to a medical device that includes a flexible shaft, which contains one or more lumens which may be inserted into a subject in any suitable manner and/or into any suitable portion of the anatomy or system thereof for introduction of material, such as, for example, fluids, nutrients, medications, blood products; monitoring of the subject, such as, for example, with respect to pressure, temperature, fluid, analytes, etc.; removal of material, such as for example, one or more body fluids; deployment of balloons, stents, grafts, or other devices; or any combination thereof. A catheter may further include various accessory components such as extension tubes, junction hubs (e.g., hubs overmolded to the shaft and/or extension tubes), fittings, connectors, and so forth. A catheter may also have various tip and shaft features including holes, splits, tapers, overmolded tips or bumps, and so forth.

As used herein, "vascular access device" refers to a device that provides access to the vascular system of a patient, such as the venous system or, in some specific instances, the central venous circulation system. This includes, but is not limited to, central venous catheters; peripherally inserted venous catheters, such as peripheral intravenous (PIV) lines; midlines; ports (e.g., implantable devices); dialysis catheters; and apheresis catheters. Vascular access devices may remain in place from days to years. The typical construction of a vascular access catheter includes a flexible shaft with one or multiple lumens with various tips, splits, tapers, and so forth, that is connected by a junction hub to extension tubes with luer fitting for attachment to other devices.

As used herein, "central access device" refers to a device that provides direct access to the central venous circulation system. As used herein, "central venous catheter" or "CVC" refers to a catheter configured to have its tip placed directly in the central venous circulation system. This term includes any such device, whether wholly implanted or partially implanted (e.g., via percutaneous insertion), that delivers medication to the central parts of the heart, such as the vena cava. Central venous catheters are examples of central access devices.

As used herein, "peripherally inserted central catheter" or "PICC" refers to a central venous catheter that is configured to enter the body of a patient through the skin (i.e., percutaneously) at a peripheral site and extend through the vasculature of the patient such that a distal end thereof is positioned directly in the central venous circulation system, such as in the superior vena cava. PICCs may also be referred to as peripherally inserted central lines. PICCs can remain in place, or dwell within the vasculature, for extended periods, such as days, weeks, months, or years.

As used herein, "pediatric catheter" refers to a catheter that is configured for use in the vasculature of a patient of age 18 years or less. Some pediatric catheters may be suitable for use in small children, such as children ages 5, 3, or 1 or less. Some pediatric catheters may be suitable for use in infants or neonates, such as infants weighing no less than, for example, 2.3 kg in some instances, and in further instances, weighing even less than 2.3 kg.

As used herein, "power injection" is consistent with the generally accepted definition of this term, and refers to pressurized infusions that occur at high flow rates, such as up to 4.0 mL/s or up to 5.0 mL/sec; that often involve injection of viscous materials, such as materials (e.g., contrast media) having a viscosity of 11.8 cP+/−0.3 cP; and that take place at elevated pressures. In like manner, a "power injectable" catheter is one that is capable of sustaining power injection without leaking, bursting, or swelling to a size that is not usable within the vasculature. For example, a power injectable catheter may be one that complies with the power injection specifications of the International Standards Organization (ISO) standard ISO 10555-1. Thus, for example, a power injectable PICC is a PICC configured to sustain power injections. PICCs may also be used for other functions, such as intravenous therapy at lower pressures or standard infusion and aspiration or blood sampling.

As used herein, "biocompatible" refers to compatibility with or suitability for use in a patient, such as for extended periods of time (e.g., weeks or months). The term may be used to designate compliance with generally accepted standards for or regulations governing a particular device, such as a catheter. For example, biocompatibility may designate compliance with one or more of ISO standards ISO 10993-1, 4, 5, 6, 10, or 11 and/or compliance with regulations of a specific jurisdiction, such as regulations set forth by the Food and Drug Administration of the Unites States of America. A biocompatible catheter may be one that is non-cytotoxic, non-sensitizing, non-irritant, non-toxic, non-pyrogenic, non-hemolytic, does not activate the complement system, has minimal effects on partial thromboplastin time, has an acceptable interaction with blood (for example, an acceptable thrombogenicity), and/or may be implanted for a desired period without significant adverse effects.

The term "patient" is used broadly herein and is not intended to be limiting. A patient can be, for example, any individual into whom a catheter or other medical device discussed herein may be placed, whether in a hospital, clinic, or other setting. The term "patient" includes humans, mammals, or any other animal possessing anatomy compatible with embodiments described herein.

As used in this specification and the appended claims, the singular forms "a," "an," and, "the" include plural referents unless the context clearly dictates otherwise. Thus, for example, reference to "a device" may include one or more of such devices, reference to "an isocyanate" may include reference to one or more isocyanates, and reference to "a siliconized polycarbonate polyurethane" may include reference to one or more of such compounds.

The terms "comprises," "comprising," "containing" and "having" and the like can have the meaning ascribed to them in U.S. patent law and can mean "includes," "including," and the like, and are generally interpreted to be open-ended terms. If an item is said to comprise, include, etc., a list of one or more components, structures, steps, or other items, that list may be nonexclusive or non-exhaustive, or it may alternatively be exclusive or exhaustive. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential, chronological, preferred, or other order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used.

As used herein, and unless otherwise expressly defined, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" or "an embodiment" means that a particular feature, structure, or characteristic described in connection with the example or embodiment is included in at least one embodiment. Thus, appearances of the phrases "in an example" or "in an embodiment" in various places throughout this specification are not necessarily all referring to the same embodiment.

It is further noted that various features are sometimes grouped together in a single embodiment, figure, or description thereof for the sake of brevity. However, this method of description is not intended to require that any given claim include more features than those expressly recited in that claim. Rather, as reflected in the claims following the present disclosure, inventive aspects may be present in a combination of less than all features presented in any single example disclosed herein.

II. Illustrative Unmet Needs Addressed by Various Embodiments

As described above, polyurethanes are typically formed by reacting a polyol, meaning a compound that includes multiple hydroxyl functional groups available for organic reactions, with a diisocyanate or other polyisocyanate. Further, polyurethanes can include both hard and soft segments. The hard segments can typically include the isocyanate component of the polyurethane in combination with a chain extender. The soft segment can typically include the polyol component of the polyurethane. In some examples, the type of polyol employed can depend on the environment in which the polyurethane will be used. For example, where a polyurethane is intended to be used in an aqueous environment, it can be desirable to use a polyether-based polyol. In other examples, where a polyurethane is intended to be used in a hydrocarbon environment, it can be desirable to use a polyester-based polyol. Further, the molecular weight, compositional ratio, chemical type, and other characteristics of the hard and soft segments can be varied to achieve desired characteristics of the polyurethane.

However, many polyurethane materials that are configured for use in aqueous environments do not have suitable resilience against or resistance to organic solvents. For example, some polyurethane materials that are configured for use in aqueous environments, such as biological environments, can experience swelling, cracking, reduced hardness, reduced mechanical strength, or the like when exposed to organic solvents. Thus, preparing a polyurethane material that is resilient in both an aqueous environment as well as an organic environment can be challenging. In some instances, polyurethanes improved in this manner, or so as to be capable for general use in aqueous environments and being resistant to occasional exposure to organic solvents, may be of particular use in certain medical devices, such as catheters.

Certain catheters may be introduced, for example, into the vasculature of a patient (e.g., the venous system) for a variety of purposes. For example, catheters may be introduced into the vasculature for purposes of delivering fluids, nutrition, blood, glucose solutions, medications, diagnostic agents, and so forth. Catheters may also be introduced for the purposes of withdrawing blood from the vasculature, for example, in order to treat the blood, to carry out diagnostics on the blood, and so forth.

Catheter shafts, including those used in central venous catheters, are typically made from polymers. Suitable polymers are typically biocompatible, can be formed into tubing of a variety of diameters, including some sufficiently small to reside within the vasculature, and may be flexible enough to be routed through the vasculature without causing trauma to the patient. When formed into tubing, the polymer chosen may also desirably provide strength sufficient to ensure that the lumen does not collapse in the vasculature, and be resistant to repeated flexure. The shaft material may desirably provide chemical resistance, burst resistance, radiopacity, durability, and/or additional properties. Silicone- or polyurethane-based polymers are commonly employed to meet these criteria, however polyurethane catheters may be preferred because they generally are mechanically stronger. In some instances, thermoplastic polyurethanes may desirably be used for catheters. Thermoplastic polyurethanes may be melt processable and may be extruded and/or molded using heat processing, while thermoset polyurethanes may be cast molded.

In the process of carrying out medically necessary or desirable tasks, or during indwelling periods between such tasks, a catheter can become colonized with microbes, such as bacteria or fungus, that can harm the patient. Additionally, in the case of, for example, the delivery of nutrition, the catheter can become fully or partially occluded with lipids. The presence of microbes and/or lipid occlusions may be particularly problematic for central venous catheters, which may reside within a patient for extended periods.

Certain methods of reducing or eliminating microbes or lipid occlusions can involve direct and prolonged exposure of a catheter to an alcohol, such as isopropyl alcohol or ethanol. One such method of exposing a catheter alcohol is referred to by clinicians as an alcohol lock. Alcohol locking of a catheter refers generally to techniques or procedures where alcohol is introduced into the catheter lumen and maintained in the lumen for a treatment period (e.g., greater than about 10 minutes, greater than about 30 minutes, greater than about one hour, or for about one hour or more), with an alcohol (e.g., ethanol) concentration from between 25% and 100% (e.g., 70%), for the purpose of disinfection or sterilization and/or lipid occlusion elimination. The practices of alcohol locking or other internal, or external, application of liquid alcohol are each referred to herein as direct and prolonged alcohol exposure.

Silicone catheters are generally used as central venous catheters when there will be direct and prolonged exposure to alcohol. However, silicone catheters can suffer from certain drawbacks, such as inferior mechanical strength and durability, as compared with polyurethane catheters. Nevertheless, it is also well known by clinicians and manufacturers that the mechanical properties of polyurethane catheters can be adversely affected when such catheters undergo direct and prolonged exposure to alcohol. Accordingly, when direct and prolonged exposure to alcohol is not used or is not expected to be used, polyurethane catheters are often preferred for use by clinicians, rather than their silicone counterparts, due to the increased durability achievable with polyurethane, particularly in power injection applications that require high flow rates and associated high pressures.

Certain thermoplastic polyurethanes can be subject to swelling in the presences of alcohol, water, and other polar solvents. For example, when central venous catheters formed of such thermoplastic polyurethanes are exposed to these agents, the catheters may soften, swell, and lose their mechanical properties, such as modulus of elasticity and tensile strength. This effect may also be accelerated at body temperatures (e.g., 37° C.). The resultant loss of these mechanical properties may cause central venous catheter failures including, but not limited to, tip instability, tip malposition, excessive swelling and/or bursts during power injection, lumen collapse during fluid aspiration, cyclic fatigue failures from repeated bending or clamping, and leakage at the junction hub from the extension legs or the catheter shaft. Accordingly, in many applications, medical device manufacturers are required to design in safety factors or specify the conditions under which polyurethane central venous catheters may be used. In many instances, manufacturers expressly caution against or disallow (e.g., provide warnings in the instructions for use against) the use of alcohol and other materials with the catheters to prevent these failures. Stated otherwise, polyurethane central venous catheters are generally not compatible with alcohol locking, as the catheters may rapidly degrade to a point where they can no longer be used as intended, particularly where the catheters are otherwise power injectable.

As a further example, certain catheters manufactured with polyurethanes, such as, for example, TECOFLEX®, TECOTHANE®, or PELLETHANE®, each available from Lubrizol Advanced Materials, of Cleveland, Ohio; QUADRATHANE® or QUADRAFLEX®, each available from Biomerics, LLC, of Salt Lake City, Utah; CHRONO-FLEX®, available from AdvanSource Biomaterials Corp., of Wilmington, Mass.; or the like, may degrade or otherwise suffer diminished performance during or after prolonged exposure to alcohol. For example, such catheters may burst during power injection or leak due to cyclic kink. This loss of performance is directly related to alcohol-related degradation in mechanical properties, such as increased swell, decreased stress crack resistance, and loss of certain mechanical properties such as hardness, modulus, and strength. Accordingly, manufacturers of central venous catheters, in many instances, explicitly disallow the use of direct and prolonged exposure to alcohol with their catheters.

Polycarbonate polyurethanes may outperform polyether polyurethanes with respect to alcohol locking, in that polycarbonate polyurethanes generally do not degrade quite as much. Moreover, aromatic varieties of either polyurethane generally outperform aliphatic varieties. Thus, alcohol locking can cause differing amounts of degradation on the following materials, which are listed, generally, in order from greatest to least degradation: aliphatic polyether polyurethanes, aromatic polyether polyurethanes, aliphatic polycarbonate polyurethanes, aromatic polycarbonate polyurethanes. However, even aromatic polycarbonate polyurethanes, when formed into catheter shafts, are generally unable to withstand the rigors of power injection after an alcohol locking event, or after many of such alcohol locking events.

The present disclosure relates to alcohol-resistant aromatic polycarbonate polyurethanes that include polysiloxane in their soft segment. Embodiments of the siliconized polycarbonate polyurethanes can demonstrate improved resistance to alcohol, as compared, for example, to polycarbonate polyurethanes. Also disclosed herein are alcohol-resistant catheters comprising the alcohol-resistant siliconized polycarbonate polyurethanes disclosed herein. In some embodiments, catheters exhibit reduced swelling, improved stress crack resistance, and/or greater retention of certain mechanical properties such as hardness, modulus, and strength, upon exposure to alcohol, as compared with other polyurethanes. Embodiments of the catheters are power injectable. Moreover, the catheters can recover well after alcohol locking, and can be suitable for long-term use in a patient. For example, some embodiments comprise PICC devices that may be suitable for long-term use in a patient, including pediatric patients.

Certain embodiments of catheters that include the siliconized polycarbonate polyurethanes may also perform well at retaining additives compounded therein. For example, the catheters may retain radiopacifiers, such as barium sulfate, sufficiently well to permit the catheters to be used with small children, and even neonates. Stated otherwise, the materials, when extruded into catheter shafts, may yield relatively small amounts of leachates when the shafts are positioned within a patient. One or more of the foregoing advantages and/or other advantages of embodiments of the siliconized polycarbonate polyurethanes and/or devices into which these materials may be incorporated are discussed further below and/or will be apparent from the present disclosure.

III. Siliconized Polycarbonate Polyurethanes

The present disclosure describes, inter alia, embodiments of a siliconized polycarbonate polyurethane that is suitable for use in an aqueous environment and that has good resistance to or resilience against a variety of organic solvents, such as, for example, alcohol (e.g., ethanol). The siliconized polycarbonate polyurethane can include a soft segment and a hard segment. The soft segment can include a polycarbonate polyol and a polysiloxane. In some instances, the polycarbonate polyol can be present in an amount greater than or equal to the amount of polysiloxane. In some embodiments, formulations in which the polysiloxane forms a specified percentage of the soft segment are particularly well suited for use in catheters, such as, for example, power injectable PICC catheters. The hard segment can include an isocyanate and a chain extender.

In further detail, a variety of polycarbonate polyols, or combinations of polycarbonate polyols, can be employed to prepare the soft segment of the polyurethane. In some examples, the polycarbonate polyol can be or include a polycarbonate diol. In some examples, the polycarbonate polyol can have a structure according to formula (I):

$$\text{HO}\left[\underset{\text{R}}{\phantom{X}}\text{O}\underset{\text{O}}{\overset{\text{O}}{\|}}\text{O}\right]_n\text{A} \quad (I)$$

where R is selected from a linear or branched, substituted or unsubstituted $C_1$-$C_{24}$ alkyl or alkylene group, A is selected from hydrogen (H) or R'OH, and n is an integer from 2 to 30. In some specific examples, A can be H. In yet other examples, A can be R'OH. In certain of such instances, R and R' can be the same. In yet other instances, R and R' can be different. In either case, R' can be selected from a linear or branched, substituted or unsubstituted $C_1$-$C_{24}$ alkyl or alkylene groups. In some examples, R and R' can be independently selected from $C_4$-$C_{12}$ linear or branched, substituted or unsubstituted alkyl or alkylene groups. In some examples, R, R', or both can be a linear alkyl or alkylene group. Thus, in some examples, the polycarbonate polyol can have a structure similar to or according to formula (II):

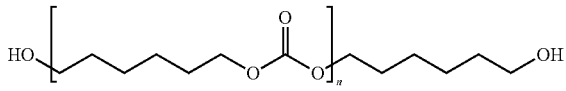

In other examples, R, R', or both can be a branched alkyl or alkylene group. Where R, R', or both include branching, any suitable number of branches can be present. In some specific examples, one or two branches can be present per R group, R' group, or both. In some examples, branches can include substituted or unsubstituted $C_1$-$C_6$ alkyl or alkylene groups. In some specific examples, branches can include a methyl, ethyl, propyl, or butyl group, or a combination thereof. Thus, for example, in some cases, the polycarbonate polyol can have a structure similar to or according to formula (III):

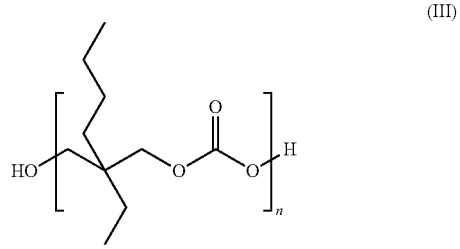

In some specific examples, one or more carbon groups in R, R', or both can be substituted. Where R, R', or both are substituted, the substitution can include oxygen, nitrogen, sulfur, hydroxyl, amino, nitro, thiol, carboxyl, another suitable substitution group, or a combination thereof. In some specific examples, R and R' are independently selected from linear, unsubstituted $C_4$-$C_{10}$ alkyl groups. In some examples, R and R' can be independently selected from a pentyl, hexyl, or heptyl group. In some examples, n can be an integer from 5 to 25, or from 10 to 15.

The polycarbonate polyol can have a variety of molecular weights, depending on the desired material properties for the siliconized polycarbonate polyurethane. For example, in some cases, increasing the molecular weight of the polycarbonate polyol can decrease the mechanical strength of the siliconized polycarbonate polyurethane and reduce the stiffness of the material. Conversely, in some cases, decreasing the molecular weight of the polycarbonate polyol can increase the mechanical strength and stiffness of the siliconized polycarbonate polyurethane. In some examples, the polycarbonate polyol can have a number average molecular weight ($M_n$) of from about 500 g/mol to about 5000 g/mol. In yet other examples, the polycarbonate polyol can have an $M_n$ of from about 500 g/mol to about 2500 g/mol, from about 1000 g/mol to about 4000 g/mol, from about 1500 g/mol to about 2500 g/mol, from about 1800 g/mol to about 2200 g/mol, or from about 1840 g/mol to about 2200 g/mol.

Generally, the polycarbonate polyol can make up greater than 50 wt % of the soft segment. In some examples, the polycarbonate polyol can make up greater than or equal to 80 wt %, 85 wt %, 88 wt %, 89 wt %, or 90 wt % of the soft segment. In some specific examples, the soft segment can include from about 50 wt % to about 98 wt % of polycarbonate polyol, though other amounts can be used as desired. In some examples, the soft segment can include from about 70 wt % to about 96 wt %, from about 75 wt % to about 85 wt %, from about 85 wt % to about 95 wt %, from about 88 wt % to about 94 wt %, from about 88 wt % to about 92%, from about 89 wt % to about 91% polycarbonate polyol.

Conversely, the polysiloxane can generally make up less than 50 wt % of the soft segment. In some examples, the polysiloxane can make up less than or equal to 20 wt %, 15 wt %, 12 wt %, 11 wt %, or 10 wt % of the soft segment. In some specific examples, the soft segment can include from about 2 wt % to about 50 wt % of polysiloxane, though other amounts can be used as desired. In some examples, the soft segment can include from about 4 wt % to about 30 wt %, from about 15 wt % to about 25 wt %, from about 5 wt % to about 15 wt %, from about 6 wt % to about 12 wt %, from about 8 wt % to about 12 wt %, from about 9 wt % to about 11 wt %, or from about 9.5% to about 10.5% polysiloxane.

A variety of polysiloxanes, or combinations of polysiloxanes, can be used to prepare the soft segment of the siliconized polycarbonate polyurethane. In some examples, the polysiloxane can have a structure according to formula (IV):

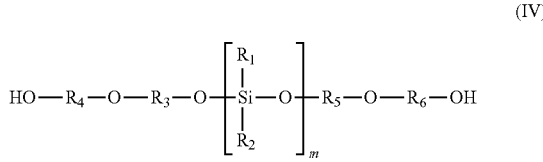
(IV)

where $R_1$ and $R_2$ are independently selected from a linear $C_1$-$C_6$ alkyl group or a hydrogen group, $R_3$ and $R_5$ are independently selected from a $C_1$-$C_{12}$ alkyl or alkylene group, $R_4$ and $R_6$ are independently selected from a $C_1$-$C_8$ alkyl or alkylene group, and m is an integer from 2 to 30. In some examples, one or more of $R_1$ and $R_2$ can be different. In yet other examples, each of $R_1$ and $R_2$ can be the same. In some examples, one or more of $R_1$ and $R_2$ can be hydrogen. In some examples, one or more of $R_1$ and $R_2$ can be a methyl group. In some specific examples, each of $R_1$ and $R_2$ can be a methyl group. In some examples, $R_3$ and $R_5$ can be independently selected from a $C_1$-$C_8$ alkyl or alkylene group. In some examples, $R_3$ and $R_5$ can be independently selected from a $C_2$-$C_8$ alkyl group. In some specific examples, $R_3$ and $R_5$ can both be an ethyl, propyl, or butyl group. In some examples, $R_4$ and $R_6$ can be independently selected from a $C_1$-$C_4$ alkyl or alkylene group. In some examples, $R_4$ and $R_6$ can be independently selected from a $C_1$-$C_4$ alkyl group. In some specific examples, $R_4$ and $R_6$ can both be a methyl, ethyl, or propyl group. In some examples, m can be an integer from 2 to 20, or from 6 to 14.

The polysiloxane can have a variety of molecular weights, depending on the specific material properties desired for the siliconized polycarbonate polyurethane. In some examples, the polysiloxane can have an $M_n$ of from about 300 g/mol to about 3000 g/mol. In some examples, the polysiloxane can have an $M_n$ from about 500 g/mol to about 1500 g/mol, from about 800 g/mol to about 1200 g/mol, from about 1500 g/mol to about 2500 g/mol, or from about 700 g/mol to about 2300 g/mol.

The polycarbonate polyol and polysiloxane can be present in the soft segment in a variety of weight ratios. In some examples, the polycarbonate polyol and polysiloxane can be present in a weight ratio of from about 20:1 to about 1:1 polycarbonate polyol to polysiloxane. In other examples, the polycarbonate polyol and polysiloxane can be present in a weight ratio of from about 20:1 to about 4:1, about 20:1 to about 8:1, about 19:1 to about 9:1, about 11:1 to about 8:1, about 11:1 to about 9:1, about 10:1 to about 9:1, or about 10:1 to about 8:1 polycarbonate polyol to polysiloxane.

The amount of soft segment and hard segment in the siliconized polycarbonate polyurethane can be adjusted to achieve desired material properties. For example, while a relatively larger hard segment can generally increase the hardness of the material, and vice versa, other material properties can also be affected by altering the relative percentages of the hard and soft segments. In some examples, the siliconized polycarbonate polyurethane can include from about 30 wt % to about 80 wt % soft segment. In yet other examples, the siliconized polycarbonate polyurethane can include from about 30 wt % to about 60 wt % soft segment. In still other examples, the siliconized polycarbonate polyurethane can include from about 40 wt % to about 70 wt % soft segment. In yet other examples, the siliconized polycarbonate polyurethane can include from about 30 wt % to about 40 wt %, from about 35 wt % to about 45 wt %, from about 40 wt % to about 50 wt %, from about 45 wt % to about 55 wt %, from about 50 wt % to about 60 wt %, from about 55 wt % to about 65 wt %, from about 54 wt % to about 58 wt %, from about 60 wt % to about 70 wt %, or from about 65 wt % to about 75 wt % soft segment. In various embodiments, the siliconized polycarbonate polyurethane can include about 69 wt %, about 56 wt %, or about 50 wt % soft segment.

Conversely, the siliconized polycarbonate polyurethane can include from about 10 wt % to about 60 wt % hard segment. In yet other examples, the siliconized polycarbonate polyurethane can include from about 10 wt % to about 30 wt %, or from about 20 wt % to about 40 wt % hard segment. In still other examples, the siliconized polycarbonate polyurethane can include from about 30 wt % to about 50 wt % hard segment. In yet other examples, the siliconized polycarbonate polyurethane can include from about 20 wt % to about 30 wt %, from about 25 wt % to about 35 wt %, from about 30 wt % to about 40 wt %, from about 35 wt % to about 45 wt %, from about 42% to about 46%, from about 40 wt % to about 50 wt %, from about 45 wt % to about 55 wt %, or from about 50 wt % to about 60 wt % hard segment. In various embodiments, the siliconized polycarbonate polyurethane can include about 31 wt %, about 44 wt %, or about 50 wt % hard segment.

The siliconized polycarbonate polyurethane can include the soft segment and hard segment at a variety of weight ratios. In some examples, the soft segment and the hard segment can be present at a weight ratio of from about 5:1 to about 1:3 soft segment to hard segment. In yet other examples, the soft segment and hard segment can be present at a weight ratio of from about 3:1 to about 1:2 soft segment to hard segment. In still other examples, the soft segment can be present at a weight ratio of from about 3:1 to about 1:1, about 3:1 to about 3:2, about 2:1 to about 1:2, or about 2:1 to about 1:1 soft segment to hard segment.

As previously described, the hard segment can include an isocyanate and a chain extender. It is noted that, as used herein, "isocyanate" or an "isocyanate compound" refers to a compound having a plurality of isocyanate groups. As such, an "isocyanate" or "isocyanate compound" can refer to a diisocyanate, or other polyisocyanate. Thus, the isocyanate can include a diisocyanate, other polyisocyanate, or a combination thereof. A variety of isocyanates can be used in the siliconized polycarbonate polyurethane. Non-limiting examples can include 4,4'-methylene diphenyl diisocyanate, bitolylene diisocyanate, methylene bis cyclohexyl diisocyanate, para-phenylene diisocyanate, trans-cyclohexane-1,4-diisocyanate, 1,6-diisocyanatohexane, 1,5-naphthalene diisocyanate, para-tetramethylxylene diisocyanate, meta-tetramethylxylene diisocyanate, 2,4-toluene diisocyanate, isophorone diisocyanate, other diisocyanates or polyisocyanates, or combinations thereof. In some specific examples, the isocyanate can be or can include 4,4'-methylene diphenyl diisocyanate. In some instances, the isocyanate can be an aromatic isocyanate.

The hard segment can include varying amounts of the isocyanate, depending on desired material properties of the siliconized polycarbonate polyurethane. In some examples, the hard segment can include from about 50 wt % to about 90 wt % isocyanate. In some further examples, the hard segment can include from about 60 wt % to about 90 wt % isocyanate. In some specific examples, the hard segment can include from about 70 wt % to about 80 wt %, from about 75 wt % to about 85 wt %, or from about 80 wt % to about 90 wt % isocyanate.

A variety of chain extenders can be included in the hard segment of the siliconized polycarbonate polyurethane. Non-limiting examples can include 1,2-propanediol, 1,3-propandiol, 2,2-dimethylpropane-1,3-diol, 2-ethyl-2-(hydroxymethyl)propane-1,3-diol, 1,4-butanediol, 1,5-pentanediol, 1,6-hexanediol, 1,7-heptanediol, 1,8-octainediol, 1,9-nonanediol, 1,10-decanediol, 1,11-undecanediol, 1,12-dodecanediol, 1,4-cyclohexanediol, 1,4-cyclohexanedimethanol, 1,4-bis(2-hydroxyethoxy)benzene, para-xyleneglycol, 1,3-bis(4-hydroxybutyl) tetramethyldisiloxane, 1,3-bis (6-hydroxyethoxypropyl) tetramethyldisiloxane, trimethylolpropane and combinations thereof. In some specific examples, the chain extender can be or can include 1,4-butanediol.

The chain extender can be included in the hard segment in various amounts, depending on the desired material properties of the siliconized polycarbonate polyurethane. In some examples, the hard segment can include from about 10 wt % to about 50 wt % chain extender. In some further examples, the hard segment can include from about 10 wt % to about 40 wt % chain extender. In some specific examples, the hard segment can include from about 20 wt % to about 30 wt %, from about 15 wt % to about 25 wt %, from about 10 wt % to about 20 wt %, or from about 20 wt % to about 22 wt % chain extender.

The isocyanate and the chain extender can be present in the hard segment in a variety of weight ratios. In some examples, the isocyanate and the chain extender can be present in the hard segment at a weight ratio of from about 10:1 to about 1:1 isocyanate to chain extender. In yet other examples, the isocyanate and the chain extender can be present in the hard segment at a weight ratio of from about 5:1 to about 1:1 isocyanate to chain extender. In still additional examples, the isocyanate and the chain extender can be present in at a weight ratio of from about 10:1 to about 5:1, about 7:1 to about 3:1, or from about 4:1 to about 2:1 isocyanate to chain extender.

In some embodiments, one or more crosslinkers may be used, such that the siliconized polycarbonate polyurethane includes crosslinked chains yielding, for example, greater mechanical and/or thermal stability as compared with otherwise identical siliconized polycarbonate polyurethane in which the crosslinkers are not employed. Non-limiting examples of crosslinkers can include trimethylolpropane, castor oil, poly(vinyl alcohol), glycerine, one or more of the polyisocyanates described above, or combinations thereof.

The siliconized polycarbonate polyurethane can also include a variety of other additives, which are not typically considered part of the hard segment or the soft segment, unless otherwise specified. For example, in some cases, the siliconized polycarbonate polyurethane can include a radiopacifier, a lubricant, a catalyst, an antioxidant, a radical inhibitor, a colorant, a filler, a nucleating agent (e.g., fumed silica), the like, or combinations thereof.

In some specific examples, the siliconized polycarbonate polyurethane can include a radiopacifier. Generally, radiopacifiers are dense fillers added to polymers to enable resultant medical devices, including catheter shafts, for instance, to be viewed under radiography when in the body. Non-limiting examples of radiopacifiers can include barium sulfate, tungsten metals, tungsten carbide, bismuth metals, bismuth oxide, bismuth oxychloride, bismuth subcarbonate, platinum, palladium, gold, zirconium oxide, the like, or combinations thereof. Where a radiopacifier is used, it can typically be included in the siliconized polycarbonate polyurethane in an amount from about 5 wt % to about 45 wt %, from about 10 wt % to about 30 wt %, from about 15 wt % to about 40 wt %, or from about 25 wt % to about 35 wt %. In various embodiments, the radiopacifier may be present in an amount no less than 20%, 25%, or 30%.

In some instances, the addition of higher amounts of filler and/or more dense fillers may increase the radiopaqueness of the resultant medical catheter shaft, but may also deteriorate the mechanical properties of the material (elongation, tensile strength, burst strength, biocompatibility, modulus, and chemical resistance, for example). Thus, the amount of filler added to a catheter material may be dependent on the particular application requirements of the material. For example, in small-diameter, thin-walled catheters—which may become difficult to see under radiography—the appropriate amount of filler may depend highly on parameters of the device as well as the expected use of the device. Moreover, for catheters that may dwell within a patient for extended periods, such as PICC devices, it can be desirable to reduce the amount of radiopacifier that leaches into the blood. A reduction of leachates may be achieved by reducing the amount of radiopacifier compounded into the polymer material, although this may render the catheter dimmer or otherwise less visible under radiography. Embodiments disclosed herein, however, can advantageously retain the radiopacifier (e.g., barium sulfate) within the polymer, thus reducing the amount of radiopacifier leachates without sacrificing a high radiopacifier content with good imaging visibility.

In some additional specific examples, the siliconized polycarbonate polyurethane can include a lubricant, such as a lubricant useful for extrusion or a mold release agent. Non-limiting examples of suitable lubricants can include polyethylene, fluorocarbon polymers (e.g., polytetrafluoroethylene), silicone resins, organic waxes (such as, for example, stearate waxes, bis-amide waxes, including ethylene bis stearamide (EBS), etc.), the like, or combinations thereof. One illustrative example of a suitable lubricant is GLYCOLUBE™ VL, available from Lonza, of Switzerland. Where a lubricant is used, the lubricant can be present in the siliconized polycarbonate polyurethane in an amount from about 0.05 wt % to about 5 wt %, or from about 0.1 wt % to about 0.5 wt %.

In yet other specific examples, the polyurethane polycarbonate can include a colorant. The colorant can include any suitable dye or pigment, or combination thereof, and can impart any suitable color to the siliconized polycarbonate polyurethane. Where a colorant is used, it can be present in the siliconized polycarbonate polyurethane in an amount from about 0.1 wt % to about 10 wt %, or from about 0.3 wt % to about 3 wt %.

The siliconized polycarbonate polyurethane can have a variety of molecular weights. Typically, the siliconized polycarbonate polyurethane can have a weight average molecular weight (Mw) of from about 50,000 g/mol to about 300,000 g/mol. In some examples, the siliconized polycarbonate polyurethane can have an Mw of from about 70,000 g/mol to about 300,000 g/mol. In other examples, the siliconized polycarbonate polyurethane can have an Mw of from about 120,000 g/mol to about 250,000 g/mol. In still other examples, the siliconized polycarbonate polyurethane can have an Mw from about 50,000 g/mol to about 150,000 g/mol, from about 150,000 g/mol to about 220,000 g/mol, from about 160,000 g/mol to about 200,000 g/mol, from about 150,000 g/mol to about 190,000 g/mol, or from about 170,000 g/mol to about 210,000 g/mol.

The siliconized polycarbonate polyurethane can also have any of a variety of isocyanate indexes. In some examples, the siliconized polycarbonate polyurethane can have an isocyanate index (i.e., the number of moles of isocyanate groups/moles of hydroxyl groups) of from about 0.98 to about 1.10, such as from about 1.00 to about 1.10. In yet other examples, the siliconized polycarbonate polyurethane can have an isocyanate index of from about 1.00 to about 1.08, about 0.98 to about 1.00, about 1.00 to 1.02, about 1.02 to about 1.05, about 1.03 to about 1.08, about 1.03 to about 1.06, about 1.04 to about 1.10, from about 1.01 to about 1.06, from about 1.02 to about 1.04, from about 1.03 to about 1.04, from about 1.04 to about 1.06, or from about 1.045 to about 1.055.

The siliconized polycarbonate polyurethane can also have a range of durometer values. In some examples, the siliconized polycarbonate polyurethane can have a Shore A durometer value of from about 65 to about 100. In yet other examples, the siliconized polycarbonate polyurethane can have a Shore A durometer value of from about 70 to about 90, from about 75 to about 85, from about 91 to about 100, from about 94 to about 98, from about 96 to about 100, from about 95 to about 99, from about 96 to about 98, or from about 97 to about 100 (including to a hardness slightly off the high end of the Shore A scale, or harder than 100). In still other examples, the siliconized polycarbonate polyurethane can have a Shore D durometer value of from about 15 to about 85, from about 60 to about 80, or from about 65 to about 75.

Methods of preparing a siliconized polycarbonate polyurethane are also disclosed. In some examples, a method can include mixing or combining a polycarbonate polyol, a polysiloxane, an isocyanate, and a chain extender to prepare a siliconized polycarbonate polyurethane. The polycarbonate polyol can be present in an amount greater than or equal to the amount of polysiloxane.

In some examples, one or more of the raw materials can be melted or otherwise pre-processed prior to combining with other components of the siliconized polycarbonate polyurethane. For example, in some cases, the polycarbonate polyol can be melted prior to combining with other components of the siliconized polycarbonate polyurethane. For example, certain polycarbonate polyols can be pre-melted at a temperature of from about 160° F. to about 200° F. In other instances, such as with certain polycarbonate diols, the pre-melting temperature may be lower, such as from about 90° F. to about 150° F. In some examples, the polycarbonate polyol can be stored at a temperature of from about 160° F. to about 175° F., with or without melting as previously described, prior to being combined with one of more other components. In some further examples, the polycarbonate polyol can be stored under a nitrogen atmosphere, argon atmosphere, or other suitable atmosphere to protect from moisture prior to being combined with one or more other components.

In some examples, the polysiloxane can also be stored at an elevated temperature, such as from about 140° F. to about 160° F., for example, prior to being combined with one or more other components. In some further examples, the polysiloxane can be stored under a nitrogen atmosphere, argon atmosphere, or other suitable atmosphere to protect from moisture prior to being combined with one or more other components.

In some examples, the isocyanate can be melted at a temperature of from about 125° F. to about 160° F. In some further examples, the isocyanate can be decanted from insoluble dimers that settle out of the liquid phase. In certain of such instances, the decanted isocyanate can be stored at about 125° F. to about 140° F. for subsequent use. In some additional examples, the isocyanate can be titrated to determine percent isocyanate content. This can allow formulation adjustments as necessary to maintain an appropriate or desired isocyanate index. In some examples, the chain extender can also be melted, as desired, prior to mixing.

The polycarbonate polyol, polysiloxane, isocyanate, and chain extender can be combined or mixed in a variety of ways and/or in one or multiple steps. For example, in some cases, the polycarbonate polyol, polysiloxane, isocyanate, and chain extender all can be added together into a common vessel and mixed contemporaneously, or stated otherwise, can be combined in a one-shot mixing process. In some instances, the components are mixed for a set period of time, such as within the range of from about 30 seconds to about 20 minutes. In other or further instances, the components are mixed until a threshold, target, or predetermined temperature is reached. For example, the reaction can be exothermic and the temperature of the mixture can increase from about 120° F. to about 230° F. or higher as mixing continues. In some instances, it may be desirable to discontinue mixing and to pour the mixture from the vessel when the threshold temperature is reached. In various instances, the threshold temperature may be within a range of from about 200° F. to about 230° F.

In some instances, a temperature of the mixture can be controlled during mixing, such as by introducing heat to the mixture from external sources or by removing heat from the mixture in a controlled manner. In other instances, such as just described, a temperature of the mixture is not controlled as reactions proceed. For example, although the starting temperatures of the various reactants may be maintained at desired starting points, once the reactants are added to the mixture, no further control of their temperature may be externally applied. Rather, although the temperature of the mixture may thereafter change, the change occurs naturally (e.g., increases) due to the thermal nature of the reaction (e.g., exothermic) and heat dissipation to the ambient environment. This temperature can be monitored, such as via any suitable temperature monitoring equipment. The process of temperature monitoring, and the use of such temperature monitoring equipment, applies equally to other portions of the present disclosure involving temperature determinations of various mixtures. In various embodiments, whether or not the temperature is controlled during the reaction, mixing of the mixture may be said to take place at a temperature of, for example, from about 120° F. to about 230° F. This convention of indicating that mixing takes place "at" a temperature or temperature range, regardless of whether the temperature is actively controlled to remain at the specified temperature or within the specified temperature range, is used consistently throughout the present disclosure and the claims.

In some examples, mixing of the components can proceed in multi-step processes. For example, in some instances, the polysiloxane and the polycarbonate polyol can be mixed prior to addition of the isocyanate and the chain extender. In certain of such instances, the polysiloxane and polycarbonate polyol can generally be added together in a first mixture and mixed at a temperature from about 120° F. to about 200° F. for a suitable mixing period, such as from about 30 seconds to about 15 minutes. Stated otherwise, rather than controlling or maintaining a temperature of the mixture during mixing, a temperature of the mixture may naturally increase within a range of from about 120° F. to about 200° F. as the mixing proceeds. In some examples, the polysiloxane and polycarbonate polyol can be mixed for 12 to 48 hours under vacuum to remove moisture and dissolved gases. In some examples, the isocyanate can then be added to the mixture of polycarbonate polyol and polysiloxane prior to adding the chain extender. Stated otherwise, after completion of mixing the first mixture, a second mixture may be formed by adding the isocyanate to the first mixture, and subsequently, a third mixture may be formed by adding the chain extender to the second mixture. The mixture of polycarbonate polyol, polysiloxane, and isocyanate—i.e., the second mixture—can be mixed for a suitable mixing period, such as from about 2 minutes to about 30 minutes. In some instances, a temperature at which the mixing takes place is not specifically or actively controlled, or stated otherwise, is not maintained within a specified or predetermined range. For example, in some instances, the isocyanate (in a preheated state, as described above) is added to the mixture of polycarbonate polyol and polysiloxane and mixed therewith, without further application of heat to the mixture. Any temperature changes that may occur during mixing at this stage may be due to heating due to the exothermal nature of the reaction and cooling due to heat transfer from the reaction vessel. After mixing the polycarbonate polyol, the polysiloxane, and the isocyanate (i.e., after mixing the second mixture), the chain extender can be added to the mixture (i.e., the third mixture can be formed) and mixed. A temperature of the third mixture may range from about 160° F. to about 230° F. as mixing continues. In some instances, the mixing proceeds for a suitable or predetermined mixing period, such as from about 30 seconds to about 15 minutes. In other or further instances, the mixing proceeds until a target temperature is reached. In various instances, the target temperature may be within a range of from about 200° F. to about 230° F.

It may be said that the first mixture is mixed for a first period. After completion of the first period, the second mixture is formed and mixed for a second period. After completion of the second period, the third mixture is formed and mixed for a third period. The term "after completion" signifies at the termination point, or at any point thereafter. For example, the first period may be terminated concurrently with the creation of the second mixture, such as by introducing the isocyanate into the polycarbonate/polysiloxane mixture. In other instances, some amount of time may pass between completion of the first mixing period and formation of the second mixture. This convention of indicating that some event takes place "after completion" of a mixing period, whether that event occurs immediately upon the termination of the mixing period or at some point in time thereafter, is used consistently throughout the present disclosure and the claims.

In yet other examples, the diisocyanate and the chain extender can be added contemporaneously to the mixture of polycarbonate polyol and polysiloxane. Stated otherwise, the first mixture can include the polycarbonate polyol and the polysiloxane, and the second mixture can be formed by adding both the isocyanate and the chain extender to the first mixture. In some instances, the components (i.e., of the second mixture) are then mixed, and the temperature of the mixture may range from about 120° F. to about 230° F. as mixing continues. In some instances, the mixing proceeds for a suitable or predetermined mixing period, such as from about 30 seconds to about 15 minutes. In other or further instances, the mixing proceeds until a target temperature is reached. In various instances, the target temperature may be within a range of from about 200° F. to about 230° F.

In yet other examples, the polysiloxane and the isocyanate can be mixed prior to addition of the polycarbonate polyol and the chain extender. Stated otherwise, the first mixture can include the polysiloxane and the isocyanate. In certain of such instances, the polysiloxane and the isocyanate can be mixed, for example, at a temperature of from about 120° F. to about 180° F. for a suitable mixing period, such as from about 2 minutes to about 30 minutes.

In some examples, the polycarbonate polyol can then be added to the mixture of polysiloxane and isocyanate prior to adding the chain extender. Stated otherwise, a second mixture can be formed by adding the polycarbonate polyol to the first mixture, and subsequently, a third mixture can be formed by adding the chain extender to the second mixture. The mixture of polysiloxane, isocyanate, and polycarbonate polyol (i.e., the second mixture) can be mixed at a temperature from 130° F. to 190° F. for a suitable mixing period, such as from about 2 minutes to about 30 minutes. The chain extender can then be added to the mixture of polysiloxane, isocyanate, and polycarbonate polyol (i.e., the third mixture can be formed) and mixed at a temperature of from 160° F. to 230° F. for a suitable mixing period, such as from about 30 seconds to about 15 minutes. In other or further instances, the mixing proceeds until a target temperature is reached. In various instances, the target temperature may be within a range of from about 200° F. to about 230° F.

In yet other examples, the polycarbonate polyol and the chain extender can be added contemporaneously to the mixture of polysiloxane and isocyanate. Stated otherwise, the second mixture can be formed by adding both the polycarbonate polyol and the chain extender to the first mixture, which includes the polysiloxane and the isocyanate. The second mixture can be mixed at a temperature of from 130° F. to 230° F. for a suitable mixing period, such as from about 2 minutes to about 15 minutes. In other or further instances, the mixing proceeds until a target temperature is reached. In various instances, the target temperature may be within a range of from about 200° F. to about 230° F.

Mixing, such as described in the foregoing paragraphs, can be achieved via any suitable mixing apparatus. For example, in some instances an overhead stirrer may be used. In certain of such instances, the overhead stirrer may be used with a gate paddle or other suitable attachment, and may be operated at a moderate speed.

In some examples, a lubricant, antioxidant, catalyst, or other suitable additive, or combinations thereof, can be added to a suitable mixture of the polycarbonate polyol, the polysiloxane, the isocyanate, and the chain extender to provide the siliconized polycarbonate polyurethane with desired characteristics. In some examples, the additive can be added in an amount from about 0.05 wt % to about 5 wt %, or from about 0.1 wt % to about 0.5 wt % of the siliconized polycarbonate polyurethane.

In some examples, the mixture of polycarbonate polyol, polysiloxane, isocyanate, chain extender, and optional additive can be cured. Curing can typically be performed at a temperature of from about 210° F. to about 250° F., though other curing temperatures can also be used with some formulations or where desirable. Further, the curing can typically be performed for a curing period of from about 12 hours to about 36 hours, though other curing periods can also be used where desirable.

Curing can be performed to prepare a cured siliconized polycarbonate polyurethane that can optionally be further compounded or otherwise processed to prepare the siliconized polycarbonate polyurethane, as desired. For example, in some cases, the cured siliconized polycarbonate polyurethane can be granulated. In certain of such instances, the siliconized polycarbonate polyurethane can be granulated to have an average particle size, for example, of from about 1 millimeter to about 10 millimeters, or from about 2 millimeters to about 8 millimeters.

In some examples, the granulated siliconized polycarbonate polyurethane can be further compounded with a radiopacifier, a colorant, a wax and/or lubricant, a nucleating agent, or other suitable compounding agent, or combinations thereof, to prepare the siliconized polycarbonate polyurethane. In some examples, the compounding agent, the granulated siliconized polycarbonate polyurethane, or both can be dried prior to compounding. The compounding agent can be added in various amounts depending on the type of compounding agent and the desired characteristics of the siliconized polycarbonate polyurethane. In some examples, the compounding agent can be added in an amount from about 5 wt % to about 45 wt %, from about 10 wt % to about 30 wt %, from about 15 wt % to about 40 wt %, or from about 25 wt % to about 35 wt %. In yet other examples, the compounding agent can be added in an amount from about 0.1 wt % to about 10 wt %, or from about 0.3 wt % to about 3 wt %.

In some further examples, the granulated siliconized polycarbonate polyurethane, optionally mixed with a compounding agent, can be further extruded and pelletized for subsequent use. Any suitable extrusion apparatus is contemplated. Two illustrative examples are models LSM 30.34 and ZSE 27, available from Leistritz, of Germany. In some instances, extrusion is achieved via twin-screw- or single-screw-extrusion. In certain of such embodiments, temperatures of various extruder zones may be set at, for example, between about 300° F. and about 600° F. In some instances, the extruder zone temperatures may be within a range of from about 340° F. to about 520° F. In further instances, screw speeds of from about 50 to about 500 RPM may be employed, for any suitable length/diameter (L/D) ratio of the auger or augers. For example, in various embodiments, the auger diameter may be within a range of from about 25 millimeters to about 35 millimeters, and the L/D ratio may be within a range of from about 25 to about 55. In certain instances, the screw speeds may be about 100 RPM with one or more augers each having, for example, a 34 millimeter diameter and an L/D ratio of 30, or each having a 27 millimeter diameter and an L/D ratio of 50. In various instances, strand pelletization or underwater pelletization may be performed on the extrusions to obtain pellets for subsequent use.

Further embodiments of siliconized polycarbonate polyurethanes and illustrative methods for forming the same will now be described, followed by more specific examples.

Any of the polycarbonate polyols described above are either provided in liquid form or are melted prior to use. In some instances, the polycarbonate polyol is melted at a temperature of from about 160° F. to about 200° F. The polycarbonate polyol can optionally be stored prior to use. In some instances, the polycarbonate polyol is stored at a temperature within a range of from about 160° F. to about 175° F. until use. In some instances, the polycarbonate polyol is protected from moisture (e.g., under nitrogen or other gas) during storage prior to use. Illustrative examples of the polycarbonate polyol include poly(hexamethylene carbonate) diols according to formula (II), above, including, without limitation, those having a number average molecular weight ($M_n$) within a range of from about 1840 g/mol to about 2200 g/mol.

Any of the polysiloxane polyols described above are either used at room temperature or are stored at a temperature within a range of from about 140° F. to about 160° F. until use. In some instances, the polysiloxane polyol is protected from moisture (e.g., under nitrogen or other gas) during storage prior to use. Illustrative examples of the polysiloxane polyol are carbinol-modified polydimethylsiloxanes according to formula (V), below, including, without limitation, those having a number average molecular weight ($M_n$) within a range of from about 925 g/mol to about 1025 g/mol, which exhibit reactivity at both ends.

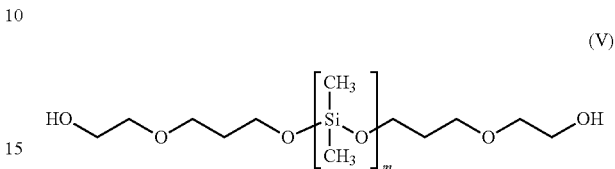

(V)

As previously noted with respect to formula (IV), above, m is an integer from 2 to 30. This polysiloxane polyol exhibits relatively high reactivity, which can, in some instances, advantageously allow it to easily be incorporated into the polyurethane chain. This polysiloxane polyol can likewise exhibit good miscibility with other polyols, which may be advantageous in some instances. For example, such an increased miscibility can improve uptake of the polysiloxane into the resultant polycarbonate polyurethane. In other examples, polysiloxane polyols may have structures similar to that of formula (V), above, but with different linkers between the polydimethylsiloxane center of the chain and the terminal hydroxyl functionalities.

Any of the isocyanates described above are either provided in liquid form or are melted prior to use. In some instances, the isocyanate is melted at about 140° F. In further instances, the melted isocyanate is decanted to remove insoluble dimers that settle out of the liquid phase. The decanted (e.g., clear) portion can be stored at an elevated temperature until use, such as within a range of from about 125° F. to about 140° F. In some instances, the isocyanate is protected from moisture (e.g., under nitrogen or other gas) during storage prior to use. A sample of the decanted liquid can be taken for titration for use in adjustment of the overall formulation. Specifically, the percentage of NCO can be determined from the titration. An illustrative example of the isocyanate is methylene diphenyl diisocyanate (MDI).

Any of the chain extenders described above are either provided in liquid form or are melted prior to use. The chain extender can be stored at an elevated temperature prior to use, such as at about 80° F. In some instances, the chain extender is protected from moisture (e.g., under nitrogen or other gas) during storage prior to use. An illustrative example of the chain extender is 1,4-butanediol (BDO).

An amount of each of the foregoing components (polycarbonate polyol, polysiloxane polyol, isocyanate, chain extender) can be selected to achieve a desired isocyanate index, which may fall within any of the ranges described above. For example, the isocyanate index may be within the range of from about 1.00 to about 1.10. Stated otherwise, a formulation of the siliconized polycarbonate polyurethane may be adjusted or fine-tuned prior to combining any of the components. In the formulation adjustment, the hydroxyl number and the $H_2O$ percentage for each of the polyols, the NCO percentage for the isocyanate, and the $H_2O$ percentage for the chain extender can be used. In some instances, adjusting the isocyanate index can represent a very small change in the mass ratios of the various components, but can have a significant effect on the properties of the final siliconized polycarbonate polyurethane.

In some instances, the isocyanate and the polysiloxane polyol are poured into a common vessel and mixed for a suitable period, such as described above. For example, the mixing may take place for a period that is within the range of from about 2 minutes to about 30 minutes. In some instances, the mixing may take place for about 5 minutes. In some instances, combining the isocyanate and the polysiloxane first can yield a more thorough and/or more uniform distribution of the polysiloxane in the final siliconized polycarbonate polyurethane material.

In some instances, the polycarbonate polyol is then added to the mixture. The mixture can be mixed for an additional period of time, such as from about two minutes to about fifteen minutes. In further instances, the mixing period is about 5 minutes.

The chain extender can then be added to the mixture of polysiloxane, isocyanate, and polycarbonate polyol and mixed at a temperature of from 160° F. to 230° F. for a suitable mixing period, such as from about 30 seconds to about 15 minutes. Alternatively, a temperature of the mixture can be monitored, and the mixing can be terminated when the temperature reaches a threshold value, which can correspond to a point at which the mixture starts to thicken. In various embodiments, the threshold value may be within a range of from about 200° F. to about 230° F. In some particular instances, the mixing time is within a range of from about 1 to about 2 minutes and/or threshold value of the temperature is within a range of from about 200° F. to about 210° F.

Upon completion of the mixing, the mixture can be poured into pans or sheets of any suitable size and construct (e.g., Teflon-coated). The mixture can then be cured in an oven, for example, at about 230° F. for about 16 to about 24 hours.

In some instances, cured cakes are removed from the pans and are chopped into smaller bricks. The bricks are then ground, or granulated, to a size that is sufficiently small to feed into compounders. Any of the granulation sizes described above are contemplated.

In some instances, the granulated siliconized polycarbonate polyurethane is dried, such as, for example, within a temperature range of from about 140° F. to about 180° F. In further instances, it may be desirable to compound a radiopacifier with the siliconized polycarbonate polyurethane. In certain of such instances, the radiopacifier may also be dried. For example, in some embodiments barium sulfate is dried prior to compounding.

In some instances, the granulated and dried siliconized polycarbonate polyurethane is compounded with any of the additives described above, such as one or more radiopacifiers and/or colorants. In some embodiments, the siliconized polycarbonate polyurethane, a radiopacifier (e.g., barium sulfate), and a colorant are weighed and then introduced into a bag, such as a large polymeric bag. The bag may be closed and tumbled (e.g., in a cement mixer) to blend.

After blending, the mixed material is fed into a pre-warmed extruder, such as a twin-screw extruder. The extrudate may be pelletized, such as to any of the pellet sizes described above. In further instances, the pellets may then be introduced into a separate extruder to form a medical component, such as a catheter shaft.

Example 1

Five test samples of siliconized polycarbonate polyurethane materials (Samples 1-5) were formulated according to a fractional factorial design of experiment (DoE) to test the effects of varying each of three parameters among low, mid, and high target values. The first parameter was the percentage by mass of the hard segment relative to the total weight of the formulation, with the low target value being approximately 37%, the mid target value being approximately 41%, and the high target value being approximately 44%. The second parameter was the percentage by mass of the polysiloxane polyol relative to the total weight of the polyol content, with the low target value being approximately 10%, the mid target value being approximately 20%, and the high target value being approximately 30%. The third parameter was the isocyanate index of the formulation, with the low target value being approximately 1.02, the mid target value being approximately 1.035, and the high target value being approximately 1.05. The actual formulation for each of Samples 1-5 is provided in Table 1, below.

TABLE 1

| Sample # | DoE Targets* (% HS-% PDMS-Iso. Index) | Measurement Description | Polycarbonate diol Soft Segment | PDMS | MDI Hard Segment | BDO | Isocyanate Index | Hardness (Shore A Durometer) |
|---|---|---|---|---|---|---|---|---|
| 1 | low-low-high | weight (g) | 7754.2 | 841.9 | 4098.6 | 954.7 | 1.049 | 90 |
| | | individual wt % | 56.8 | 6.2 | 30.0 | 7.0 | | |
| | | wt % of polyol component | 90.2 | 9.8 | n/a | n/a | | |
| | | soft segment wt % vs. hard segment wt % | 63.0 | | 37.0 | | | |
| 2 | low-high-low | weight (g) | 6062.5 | 2531.2 | 4123.6 | 925.8 | 1.017 | 91 |
| | | individual wt % | 44.4 | 18.6 | 30.2 | 6.8 | | |
| | | wt % of polyol component | 70.5 | 29.5 | n/a | n/a | | |
| | | soft segment wt % vs. hard segment wt % | 63.0 | | 37.0 | | | |
| 3 | high-low-low | weight (g) | 6894.4 | 784.5 | 4739.6 | 1270.6 | 1.015 | 97 |
| | | individual wt % | 50.4 | 5.7 | 34.6 | 9.3 | | |
| | | wt % of polyol component | 89.8 | 10.2 | n/a | n/a | | |
| | | soft segment wt % vs. hard segment wt % | 56.1 | | 43.9 | | | |
| 4 | high-high-high | weight (g) | 5390.4 | 2249.9 | 4823.7 | 1180.9 | 1.046 | 96 |
| | | individual wt % | 39.5 | 16.5 | 35.4 | 8.7 | | |
| | | wt % of polyol component | 70.6 | 29.4 | n/a | n/a | | |
| | | soft segment wt % vs. hard segment wt % | 56.0 | | 44.0 | | | |

TABLE 1-continued

| Sample # | DoE Targets* (% HS-% PDMS- Iso. Index) | Measurement Description | Polycarbonate diol Soft Segment | PDMS | MDI Hard Segment | BDO | Isocyanate Index | Hardness (Shore A Durometer) |
|---|---|---|---|---|---|---|---|---|
| 5 | mid-mid-mid | weight (g) | 6468.3 | 1576.9 | 4492.2 | 1098.5 | 1.035 | 95 |
| | | individual wt % | 47.4 | 11.6 | 32.9 | 8.1 | | |
| | | wt % of polyol component | 80.4 | 19.6 | n/a | n/a | | |
| | | soft segment wt % vs. hard segment wt % | 59.0 | | 41.0 | | | |

*Samples 1-5 were formulated according to a fractional factorial design of experiment (DoE) to test the effects of varying each of three parameters among low, mid, and high target values, as follows: Parameter 1: wt % of hard segment (relative to total weight of formulation), with low ≈37%, mid ≈41%, and high ≈44%; Parameter 2: wt % of the PDMS diol (relative to total weight of polyol content), with low ≈10%, mid ≈20%, and high ≈30%; Parameter 3: isocyanate index, with low ≈1.02, mid ≈1.035, and high ≈1.05.

For each of Samples 1-5, the polycarbonate polyol was poly(hexamethylene carbonate) diol (PHMCD) with a molecular weight of 2020 g/mol±180 g/mol. The polycarbonate polyol was melted at a temperature of from 160° F. to 200° F. and then stored at a temperature of from 160° F. to 175° F. until use. During storage, the polycarbonate polyol was protected from moisture under nitrogen.

For each of Samples 1-5, the polysiloxane polyol was carbinol-modified polydimethylsiloxane (PDMS) according to formula (V), above, with a molecular weight of 975 g/mol±50 g/mol. The polysiloxane polyol was stored at room temperature and protected from moisture under nitrogen until use.

For each of Samples 1-5, the isocyanate was monomeric diphenylmethane 4,4'-diisocyanate. The isocyanate was melted at 140° F. and decanted to remove insoluble dimers that settled out of the liquid phase. The decanted portion was stored at a temperature of from 125° F. to 140° F. and protected from moisture under nitrogen until use. A sample of the decanted liquid was taken for titration to determine the NCO concentration by which the overall formulation was adjusted according to the DoE isocyanate index target.

For each of Samples 1-5, the chain extender was 1,4 butanediol. The chain extender was stored at 80° F. and protected from moisture under nitrogen until use.

For each of Samples 1-5, the polysiloxane polyol and the molten MDI were added to a bucket and mixed for 5 minutes via an overhead stirrer at a moderate speed. The polycarbonate diol was then added to the bucket and the mixture was mixed for an additional 5 minutes via the overhead stirrer at the moderate speed. The BDO was then added to the bucket and the mixture was mixed for an additional 1 to 2 minutes via the overhead stirrer at the moderate speed. The overhead stirrer was then stopped and the mixture was poured onto baking sheets and cured overnight in an oven at 230° F.

After curing, the material was removed from the baking sheets and mechanically ground into particles having an average particle size less than about 10 millimeters. The particles were then dried in a desiccant dryer and subsequently stored for subsequent use.

For each of Samples 1-5, a small quantity of the dried siliconized polycarbonate polyurethane particles was injection molded to form test plaques, which were then tested according to the ASTM D2240 standard using a Check-Line HPSA manual durometer. The measured durometers are reported in the final column of Table 1.

Example 2

Five lots of materials—Lots 1-5—were prepared using portions of each of Samples 1-5 of Example 1, above, respectively. To prepare each of Lots 1-5, a respective quantity of one of the siliconized polycarbonate polyurethanes of Samples 1-5 was introduced into a polymeric bag, along with a quantity of barium sulfate in an amount suitable to achieve radiopacity of the material (e.g., when extruded into a catheter shaft), and with a quantity of powdered colorant in an amount suitable to achieve a desired and consistent coloring of the material. In particular, the relative amounts of the components were 69.1% siliconized polycarbonate polyurethane, 29.6% barium sulfate, and 1.3% colorant. This is summarized in Table 2, below. The bag was closed and tumbled in a cement mixer to thoroughly blend the components. Each mixture was then fed to a twin-screw extruder for compounding, was pelletized, and was then dried. Lots 1-5 were stored for subsequent use.

TABLE 2

| | Siliconized Polycarbonate Polyurethane | | | |
|---|---|---|---|---|
| Lot # | Sample # (from Example 1) | wt % | Barium Sulfate wt % | Colorant wt % |
| 1 | 1 | 69.1 | 29.6 | 1.3 |
| 2 | 2 | 69.1 | 29.6 | 1.3 |
| 3 | 3 | 69.1 | 29.6 | 1.3 |
| 4 | 4 | 69.1 | 29.6 | 1.3 |
| 5 | 5 | 69.1 | 29.6 | 1.3 |

Figure 2A:
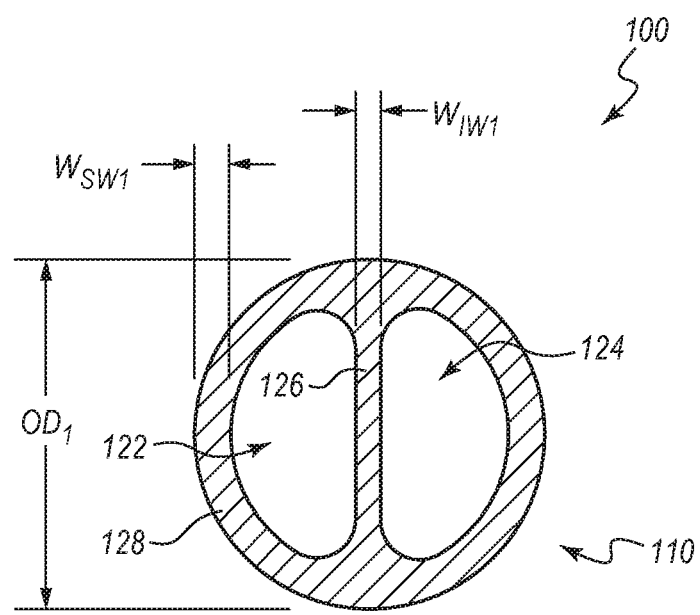
FIG. 2A is a cross-sectional view of the catheter shaft of FIG. 1 taken along the view line 2A-2A in FIG. 1.
Figure 2B:
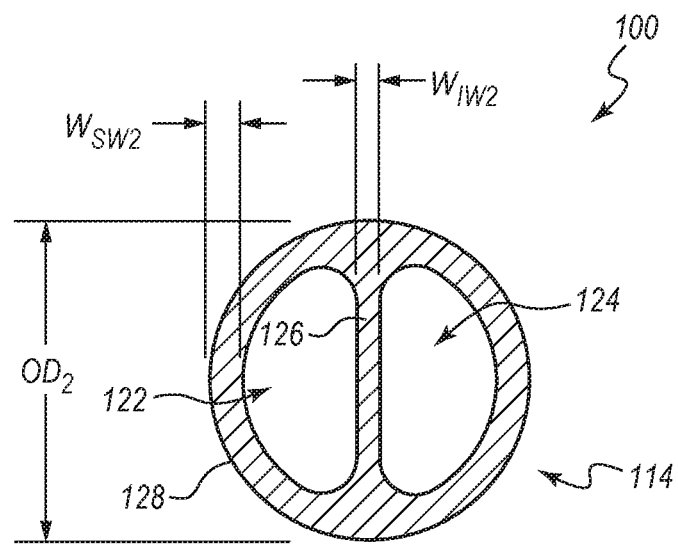
FIG. 2B is a cross-sectional view of the catheter shaft of FIG. 1 taken along the view line 2B-2B in FIG. 1.

A quantity of each of Lots 1-5 was extruded into multiple dual-lumen, reverse taper catheter shafts of the form depicted in FIGS. 1, 2A, and 2B. The effect of alcohol locking on the burst pressure of the catheter shafts was then tested.

In particular, as shown in FIG. 1, a catheter 100 of the specified form extends from a proximal end 102 to a distal end 104. The proximal end 102 of the catheter 100 terminates at a proximal tip 106 and the distal end 104 terminates at a distal tip 108.

The proximal end 102 includes a connection region 110 at which any suitable connection device can be coupled to the catheter shaft 100. For example, in some instances, a junction hub can be overmolded to the connection region 110, which junction hub can further be connected with one or more extension legs, each of which may be coupled with a connector (e.g., a luer connector). For each of the catheter shafts of the present Example 2, a female luer connector (not shown) was adhered directly to the connection region 110.

The catheter shaft 100 further includes a reverse taper region 112, which may alternatively be referred to as a bump, and a reduced diameter region 114, which extends from a distal end of the reverse taper region 112 to the distal tip 108 of the catheter shaft 100. For the catheter shafts of the present Example 2, the length $L_C$ of the connection region 110 was within a range of from 0.35 inches to 0.51 inches, the length $L_T$ of the reverse taper region 112 was no greater than 2 inches, and the effective length $L_E$ of the catheter shaft 100 (which includes the reverse taper region 112 and the reduced diameter region 114) was no less than 26 inches. Accordingly, the length of the reduced diameter region 114 was at least approximately 23.5 inches. The reduced diameter region 114 may also be referred to as an insertion region.

As shown in FIGS. 2A and 2B, the catheter shaft 100 defines two lumens 122, 124 that are separated from each other along the full length of the catheter shaft 100 via an inner wall 126, which may also be referred to as a septum or central barrier, which defines an inner surface of each lumen. In typical use, each lumen 122, 124 may be accessed separately, such as via separate extension tubes that are each in fluid communication with only one of the lumens 122, 124. For each of the catheter shafts of the present Example 2, however, a female luer connector (not shown) that provided simultaneous access to both lumens 122, 124 was adhered via Loctite 4011 adhesive to the connection region 110.

FIG. 2A depicts a cross-section through the enlarged connection region 110, and FIG. 2B depicts a cross-section through the reduced diameter region 114. The inner wall 126 defines a first width $W_{IW1}$ in the connection region 110 and a second width $W_{IW2}$ in the reduced diameter region 114. The width of the inner wall 126 can taper from the first width $W_{IW1}$ to the second width $W_{IW2}$ along the length $L_T$ of the reverse taper region 112. For the catheter shafts of the present Example 2, the first width $W_{IW1}$ was no less than 0.007 inches and the second width $W_{IW2}$ was no less than 0.005 inches.

With continued reference to FIGS. 2A and 2B, an outer surface of each lumen 122, 124, which extends from one end of the inner surface to an opposite end thereof, is defined by a sidewall 128. The sidewall 128 extends about the full circumference of the catheter shaft 100. The sidewall 128 defines a first width $W_{SW1}$ in the connection region 110 and a second width $W_{SW2}$ in the reduced diameter region 114. The width of the sidewall 128 can taper from the first width $W_{SW1}$ to the second width $W_{SW2}$ along the length $L_T$ of the reverse taper region 112. For the catheter shafts of the present Example 2, the first width $W_{SW1}$ was no less than 0.007 inches and the second width $W_{SW2}$ was no less than 0.004 inches.

An outer surface of the sidewall 128 defines an outer diameter of the catheter shaft at each position along a full length thereof. The sidewall 128 defines a first outer diameter $OD_1$ in the connection region 110 and a second outer diameter $OD_2$ in the reduced diameter region 114. The outer diameter of the sidewall 128 can taper from the first outer diameter $OD_1$ to the second outer diameter $OD_2$ along the length $L_T$ of the reverse taper region 112. For the catheter shafts of the present Example 2, the first outer diameter OD was no greater than about 6 French and the second outer diameter $OD_2$ was 5 French. The catheter shaft 100 can define the second outer diameter $OD_2$ along no less than 75, 80, 90, or 95 percent of an insertable portion of the effective length $L_E$. The catheter shafts 100 may be referred to as 5 French, dual-lumen, reverse taper (or bump) catheter shafts. Shafts of such a configuration may be particularly suitable for use, for example, in power-injectable PICC devices.

Samples of the numerous catheter shafts that were extruded from Lots 1-5 were subjected to initial burst pressure tests to determine viability for further testing. The catheter shafts formed from Lot 2 did not meet minimum performance benchmarks, and thus further testing proceeded only with respect to catheter shafts formed from Lots 1, 3, 4, and 5.

Test catheters that included the catheter shafts formed from Lots 1, 3, 4, and 5 and female luer connectors adhered thereto were conditioned in a variety of ways and then tested to determine the pressure at which bursting occurred for each condition. At least five (5) catheters from each of Lots 1, 3, 4, and 5 were tested for each condition, unless otherwise specified.

A first group of test catheters was subjected to a "No Flush" condition, in which each catheter was submerged in a 0.9% saline bath at 37° C. for a period of at least two hours. This condition is referred to as "No Flush" because it does not involve priming the catheter with ethanol and subsequently flushing the primed catheter with saline, as other conditions do. The catheters were then removed from the saline bath and tested.

A second group of test catheters was subjected to a "Flush" condition, in which each catheter was first subjected to the No Flush condition described above, then removed from the saline solution bath. The female luer of the catheter was then coupled with a 10-mL syringe that was filled with 70% ethanol. The syringe was used to flush and prime the catheter shaft with the 70% ethanol. Without removing the syringe from the female luer connector, the distal end of the catheter was folded over and pinched with a binder clip to clamp the shaft shut. The syringe was then removed and immediately replaced with a male luer lock cap. The catheter was then submerged again in the 0.9% saline bath at 37° C. for a period of between 60 and 70 minutes. The catheter was then removed again from the 0.9% saline bath. The male luer lock cap was removed and immediately replaced with a 10-mL syringe filled with 0.9% saline at 37° C. The binder clip was removed and the syringe was used to flush the catheter shaft. After having been subjected to this Flush conditioning, the catheters were then tested.

The Flush conditioning, during which the catheter was primed with 70% ethanol and submerged in the 0.9% saline bath for a period of 60 to 70 minutes, may also be referred to as an alcohol lock or an ethanol lock, and is analogous to alcohol locking in a clinical setting. For example, a PICC catheter, while within a patient, may become infected with bacteria or other microbes and/or may be at least partially occluded by lipids and/or other materials. In this setting, ethanol or isopropyl alcohol may be introduced into the catheter, such that the catheter—in particular, the inner surfaces of the catheter that define the lumen or lumens into which the alcohol has been introduced—maintains direct and prolonged exposure to the alcohol. This exposure can disinfect the lumen or lumens and/or can clear the obstructing lipids or other matter. In clinical settings, an alcohol locking event may desirably occur for a period of at least one hour. The alcohol lock period may be longer or shorter, in some contexts. An alcohol lock of at least one hour, however, can generally achieve clinical objectives, and thus may be referred to herein as a clinically acceptable, clinically relevant, or clinically effective locking period. Depending on the objectives to be achieved from an alcohol lock event, in various instances, a clinically effective locking period may be no less than about 10, 20, 30, 45, or 60 minutes.

Additional groups of test catheters were subjected to a "Flush & ## Minutes" condition, in which each catheter was first subjected to the No Flush and Flush conditions described above, then submerged in the 0.9% saline bath at 37° C. for the recovery period designated by the "## Minutes" term. Recovery periods of 15, 30, 45, 60, and 105 minutes were tested. Thus, for example, a catheter subjected to a Flush & 15 Minutes condition was first subjected to the No Flush condition, followed by the Flush condition, and then submerged in the 0.9% saline bath for a recovery period of 15 minutes. At the completion of soaking for the recovery period, the catheter was removed from the saline bath and tested.

Upon completion of preconditioning, the catheter was clamped at the distal end by folding over approximately 1 inch of the distal end of the tube and securing the folded end with a binder clip. The catheter was then coupled to testing equipment via the female luer connector. The testing equipment filled the catheter with nitrogen gas and increased the pressure of the gas until the catheter shaft burst, and recorded the pressure at which bursting occurred. As previously noted, the catheters were constructed with female luer connectors that establish simultaneous fluid communication with both lumens of the catheter shaft. Accordingly, during pressurization of the catheter shaft, both lumens were simultaneously exposed to identical pressure conditions. The burst pressure for the shaft was reached when either of the lumens was compromised (i.e., when the sidewall 128 ruptured).

Figure 3:
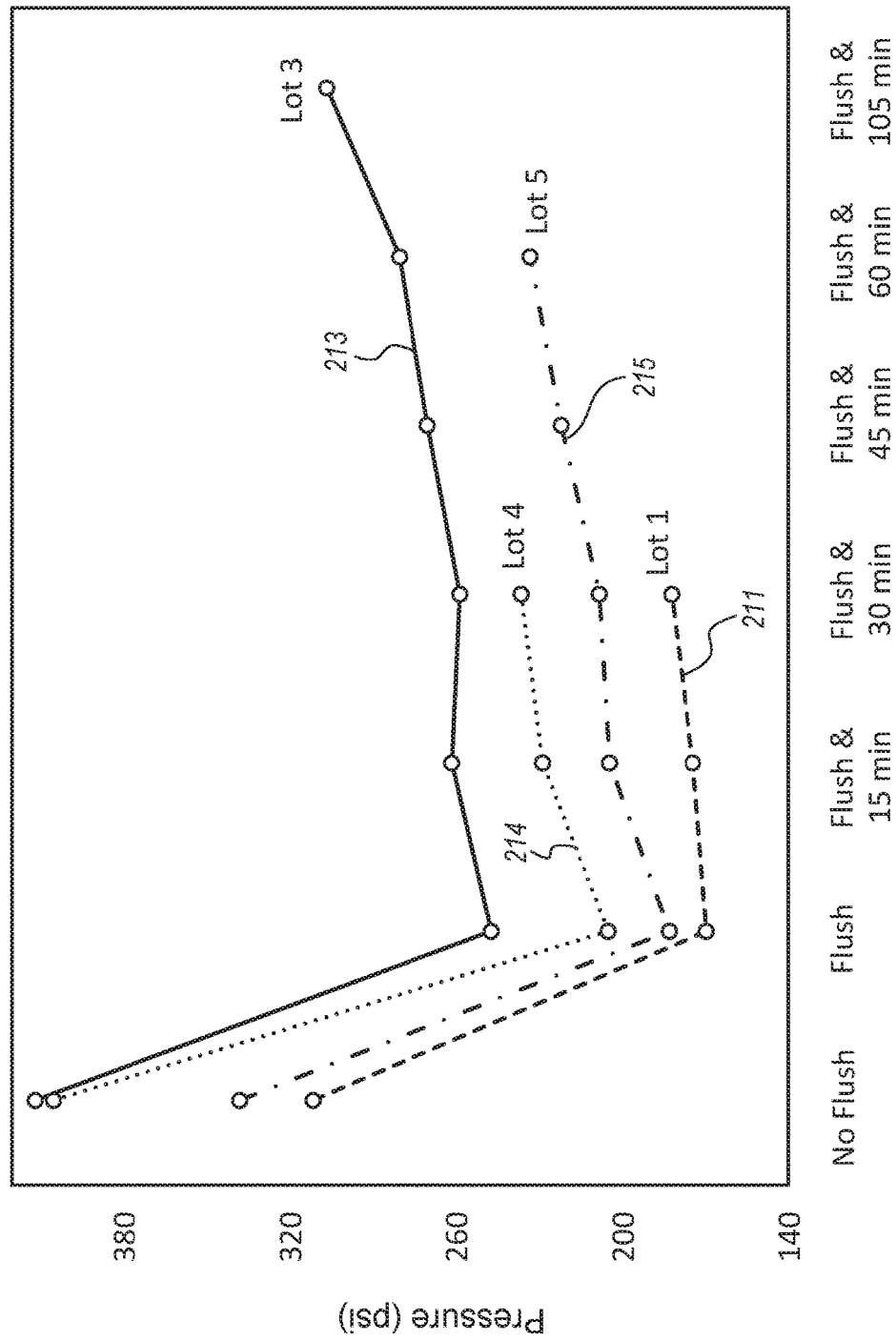
FIG. 3 is a plot of burst pressures exhibited by various catheters that comprised catheter shafts of the form depicted in FIGS. 1, 2A, and 2B, which catheter shafts were extruded from different embodiments of siliconized polycarbonate polyurethanes according to the present disclosure.

The test results are provided in Table 3 below and in FIG. 3. FIG. 3 depicts a plot 200 with a separate curve 211, 213, 214, 215 connecting the data points for the catheters associated with each of Lots 1, 3, 4, and 5, respectively. In plot 200, the uniform horizontal spacing between adjacent test conditions does not, in every instance, accurately portray quantities of time associated with those conditions. Stated otherwise, the horizontal axis is not, in all instances, accurately scaled with respect to time.

recovered from alcohol locking at approximately the same rate as those of the remaining lots.

These are surprising, unexpected, and unpredictable results, particularly when the performance of the material of Lot 3 is compared with that of Lot 4. With reference again to Table 1, the Sample 3 and Sample 4 siliconized polycarbonate polyurethanes that were used in Lot 3 and Lot 4, respectively, were very similar. These materials had nearly identical ratios of soft segment to hard segment and exhibited very similar hardness. These polyurethanes differed, however, in the percentage of the soft segment constituted by the polysiloxane polyol: 10.2% for Lot 3, compared to 29.4% for Lot 4.

For the catheters from these lots that were subjected to the No Flush condition, the average burst pressure of the Lot 3 catheters exceeded that of the Lot 4 catheters by less than 2%. This is unsurprising, in view of the similarities between the substances just discussed. However, for the catheters that were subjected to the Flush condition (i.e., were alcohol locked), the average burst pressure of the Lot 3 catheters exceeded that of the Lot 4 catheters by 17%. Thus, the Lot 3 catheters were significantly more resistant to alcohol locking than were the Lot 4 catheters, which is very surprising. As previously discussed, silicones are known to resist polar organic solvents, such as alcohol, and thus may be employed in catheters that are capable of withstanding alcohol locking. Accordingly, one would expect that a larger silicone content in the soft segment would yield improved alcohol resistance, but the opposite was observed in this series of tests.

The Lot 3 catheters are capable of withstanding high pressures, even after an alcohol locking event. In particular,

TABLE 3

| Shaft Material Lot #* | | 1 | 3 | 4 | 5 |
|---|---|---|---|---|---|
| No Flush | Avg. Burst Pressure (psi) | 311 | 412 | 405 | 338 |
| | Standard Deviation | 55 | 3 | 7 | 9 |
| | Sample Size | 10 | 7 | 5 | 6 |
| Flush | Avg. Burst Pressure (psi) | 170 | 247 | 205 | 183 |
| | Standard Deviation | 6 | 5 | 5 | 4 |
| | Sample Size | 7 | 5 | 7 | 5 |
| Flush & 15 Min | Avg. Burst Pressure (psi) | 174 | 261 | 229 | 204 |
| | Standard Deviation | 3 | 7 | 7 | 4 |
| | Sample Size | 8 | 5 | 8 | 5 |
| Flush & 30 Min | Avg. Burst Pressure (psi) | 182 | 258 | 236 | 208 |
| | Standard Deviation | 3 | 5 | 4 | 4 |
| | Sample Size | 7 | 5 | 7 | 5 |
| Flush & 45 Min | Avg. Burst Pressure (psi) | [not tested] | 270 | [not tested] | 222 |
| | Standard Deviation | [not tested] | 5 | [not tested] | 10 |
| | Sample Size | [not tested] | 5 | [not tested] | 5 |
| Flush & 60 Min | Avg. Burst Pressure (psi) | [not tested] | 280 | [not tested] | 233 |
| | Standard Deviation | [not tested] | 7 | [not tested] | 6 |
| | Sample Size | [not tested] | 5 | [not tested] | 5 |
| Flush & 105 Min | Avg. Burst Pressure (psi) | [not tested] | 306 | [not tested] | [not tested] |
| | Standard Deviation | [not tested] | 30 | [not tested] | [not tested] |
| | Sample Size | [not tested] | 6 | [not tested] | [nottested] |

*The catheter shafts formed from Lot 2 did not meet minimum performance benchmarks, and thus no further testing was performed for this material.

The catheters having catheter shafts formed of the material of Lot 3 exhibited the highest burst pressures under each variety of preconditioning. Moreover, these catheters were more resistant to alcohol locking (i.e., the Flush condition) than were the catheters from the remaining lots. In particular, a comparison of the burst pressures of the No Flush and Flush conditions reveals that the catheters of Lot 1 suffered a 45% drop, those of Lot 4 suffered a 49% drop, and those of lot 5 suffered a 46% drop, whereas those of Lot 3 only suffered a 40% drop. Furthermore, the catheters of Lot 3 the Lot 3 catheters were subjected to an alcohol lock for a locking period of no less than one hour, and were then either burst tested directly or were burst tested after a variety of recovery periods. Even without any recovery period, the Lot 3 catheters would be suitable for use at power injection pressures. In particular, immediately after Flush conditioning (i.e., a locking period of at least one hour), the Lot 3 catheters had a burst pressure of 247±5 psi. Thus, these catheters would be operable at pressures up to about 180, 190, 200, 210, 220, 230, or even 240 psi. The performance of the catheters steadily improved after recovery periods of 15, 30, 45, 60, and 105 minutes. For example, after a recovery period of 15 minutes, the catheters would be operable at pressures up to about 180, 190, 200, 210, 220, 230, 240, or even 250 psi. After a recovery period of 45 minutes, the catheters would be operable at pressures of up to about 180, 190, 200, 210, 220, 230, 240, 250, or even 260 psi. After a recovery period of 60 minutes, the catheters would be operable at pressures of up to about 180, 190, 200, 210, 220, 230, 240, 250, 260, or even 270 psi. And after a recovery period of 105 minutes, the catheters would be operable at pressures of up to about 180, 190, 200, 210, 220, 230, 240, 250, 260, 270, or even 280 psi.

Example 3

A quantity of each of Lots 1, 3, 4, and 5, as described above with respect to Example 2, was extruded into multiple dual-lumen, reverse taper catheter shafts of the form described with respect to Example 2 and depicted in FIGS. 1, 2A, and 2B. The effects of alcohol locking on the tensile strength and strain of the catheter shafts was then tested at three separate regions of the shafts. In particular, the tensile force required to break three different sections of the extruded tubing was measured for a variety of conditions. From five to ten catheters for each of Lots 1, 3, and 5 were tested for each condition. The averaged results of the tensile strength tests are shown in plots 301, 302, and 303 of FIGS. 4A, 4B, and 4C, respectively, and the averaged results of the strain tests are shown in plots 401, 402, and 403 of FIGS. 5A, 5B, and 5C, respectively. In these plots, the curves 311, 313, 315; 321, 323, 325; 331, 333, 335; 411, 413, 415; 421, 423, 425; and 431, 433, 435 connect the data points for the catheters associated with each of Lots 1, 3, and 5, respectively. Further, in these plots, the uniform horizontal spacing between adjacent test conditions does not, in every instance, accurately portray quantities of time associated with those conditions. Stated otherwise, the horizontal axis is not, in all instances, accurately scaled with respect to time For a first group of test catheter shafts, each shaft was cut into three separate three-inch long segments from three specified sections of the shaft, which sections are identified herein as Sections 1, 2, and 3. With reference again to FIG. 1, Section 1 represents a three-inch region of the proximal end of the catheter shaft that includes an entirety of the reverse taper region 112 and, at either end thereof, small portions of each of the connection region 110 and the reduced diameter region 114, respectively. Section 2 represents a three-inch region positioned approximately at the center of the reduced diameter region 114. Section 3 represents a three-inch region positioned slightly proximal of the distal tip 108. After cutting, each segment was then clamped in the testing equipment and tested for ultimate tensile strength and strain.

This first group of test catheter shafts did not undergo any preconditioning involving exposure to saline or other solutions. Accordingly, this condition is referred to herein as "Dry." The Dry tensile strength and strain for the catheter shafts formed from Lot 4 were also tested, but were sufficiently lower than those for Lots 1, 3, and 5 to determine that no further testing would be performed on these catheter shafts. Accordingly, plots 301, 302, and 303 in FIGS. 4A, 4B, and 4C, respectively, are only directed to the test results for Lots 1, 3, and 5.

Additional groups of test catheters were subjected to the No Flush, Flush, and Flush & ## Minutes conditions described above with respect to Example 2. Recovery times of 15, 30, 45, and 60 minutes were tested. For each group, each catheter shaft was then cut into Sections 1, 2, and 3, and each section was then tested.

Figure 4A:
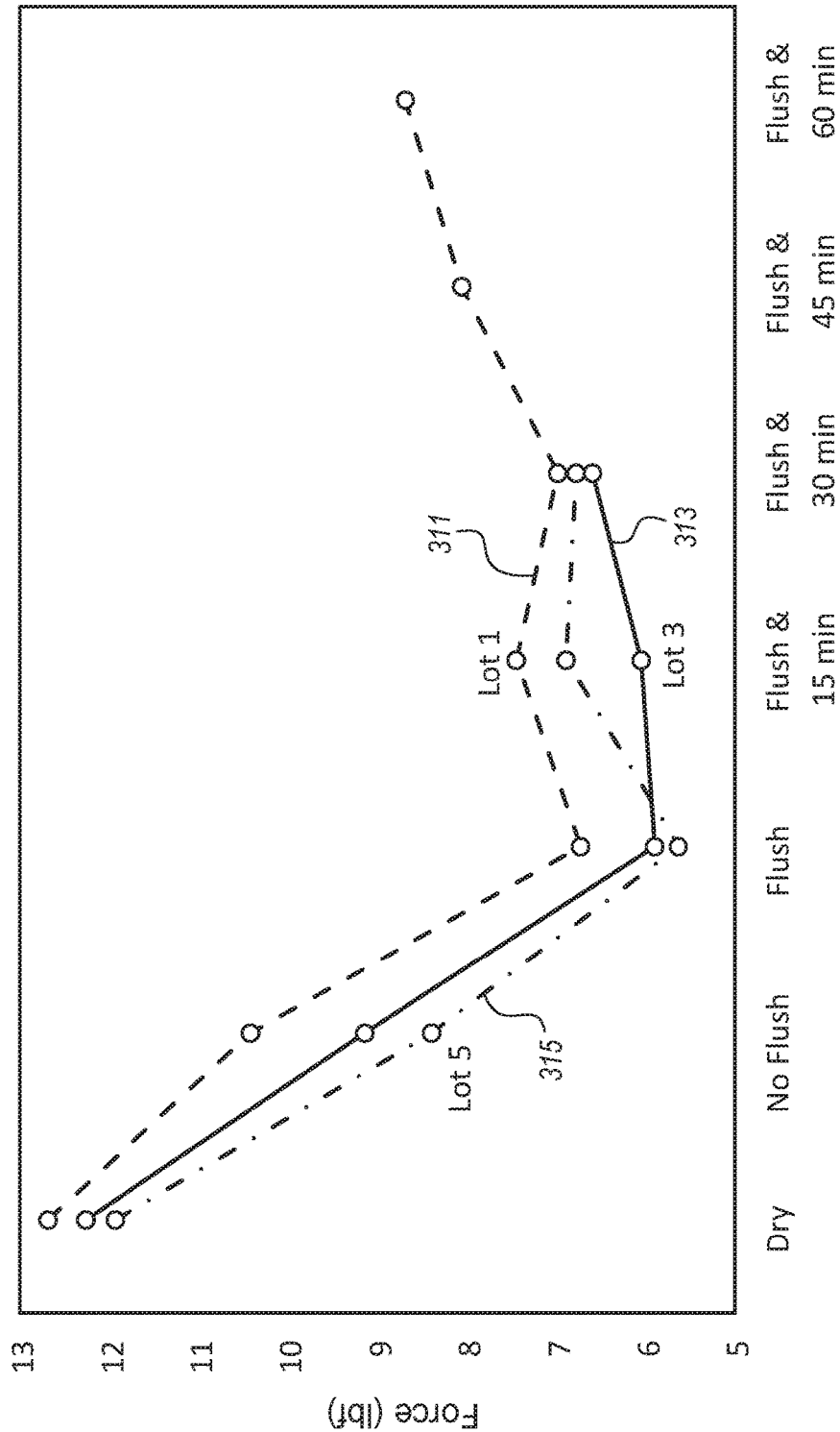
FIGS. 4A-4C are plots of tensile strengths exhibited by various sections cut from catheter shafts of the form depicted in FIGS. 1, 2A, and 2B, which catheter shafts were extruded from different embodiments of siliconized polycarbonate polyurethanes according to the present disclosure.
Figure 4B:
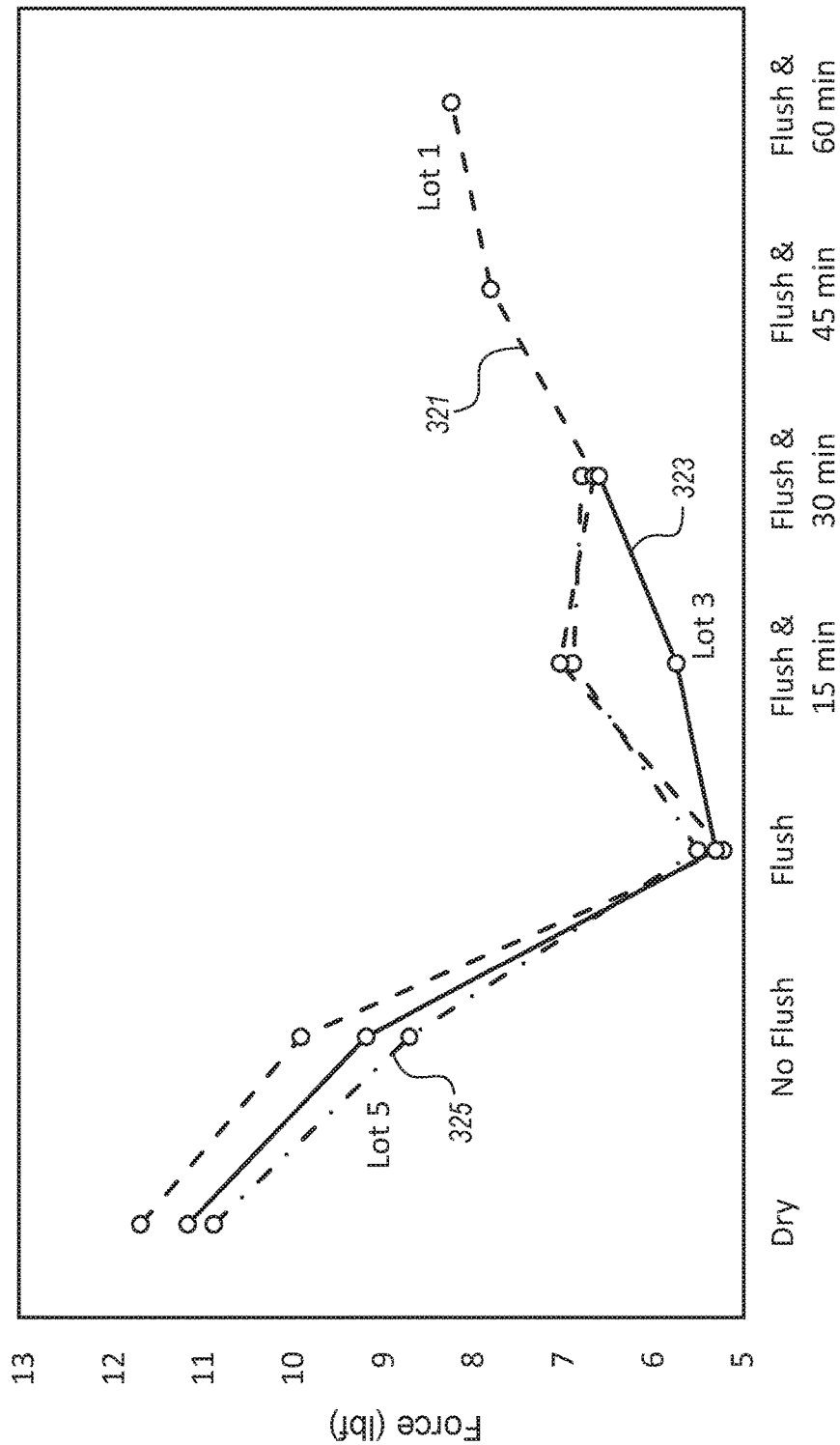
Figure 4C:
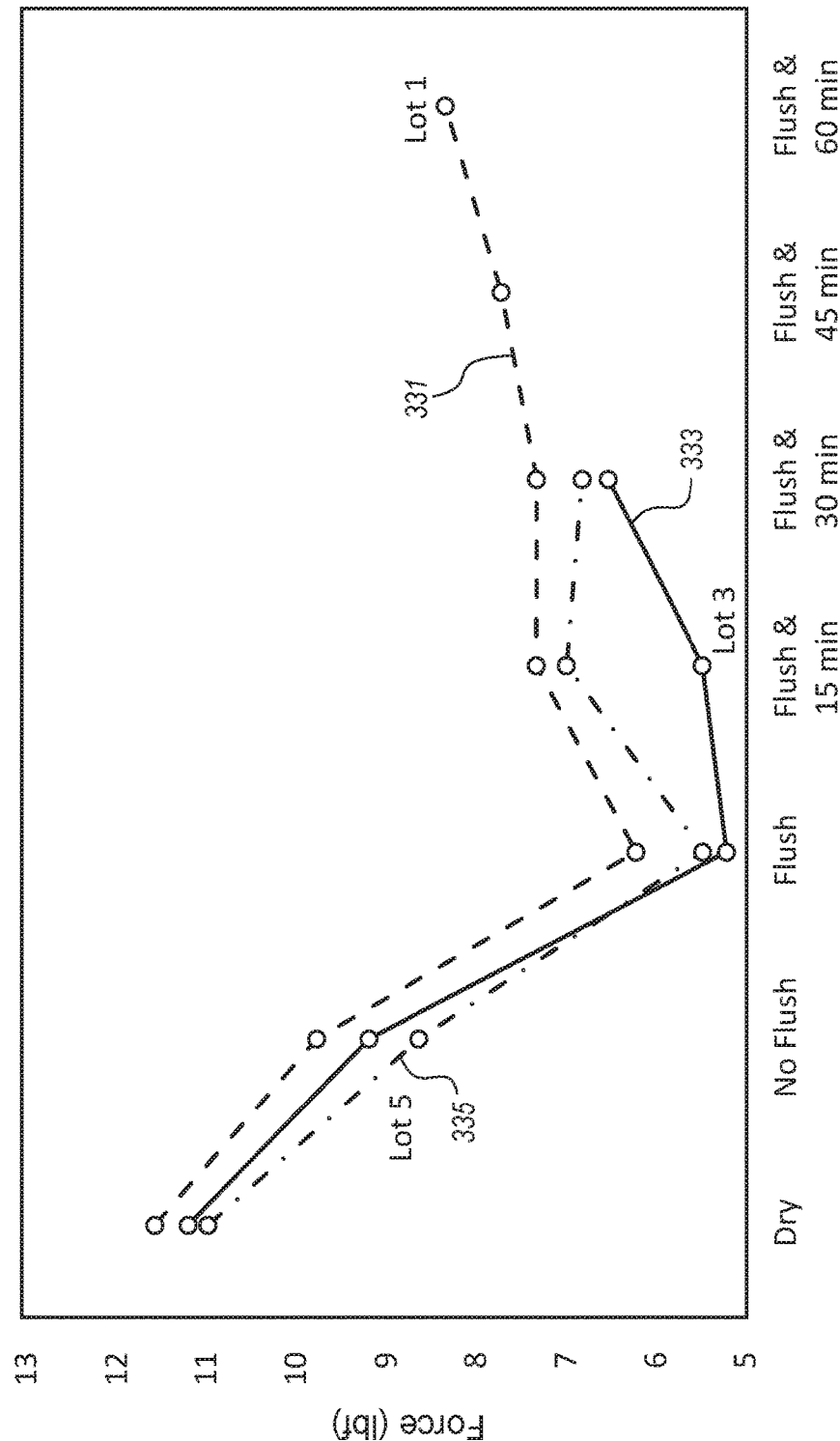

These tests revealed additional surprising, unexpected, and unpredictable results. With respect to ultimate tensile strength, as shown in FIGS. 4A-4C, the catheter shafts formed from the materials from Lots 1, 3, and 5 behave quite similarly to each other, although the Lot 1 group generally exhibits the highest ultimate tensile strength while the Lot 3 group generally exhibits the lowest. It might be expected that those materials that exhibit the highest ultimate tensile strength would likewise exhibit the highest resistance to bursting. This is not what was observed. Although Lot 1 generally performed better with respect to ultimate tensile strength, under all testing conditions, than did the remaining lots, and Lot 3 generally performed the worst, the opposite was true for the burst pressure tests (see FIG. 3). In some instances, the material of Lot 3 may be preferable to that of Lot 1 to form power-injectable catheters due to the elevated pressures involved with power injection and the concomitant importance of burst resistance. Stated otherwise, in such instances, Lot 3 may be preferable to Lot 1 because a superior burst resistance performance may be more relevant to withstanding the rigors of power injection than would a superior ultimate tensile strength performance.

Figure 5A:
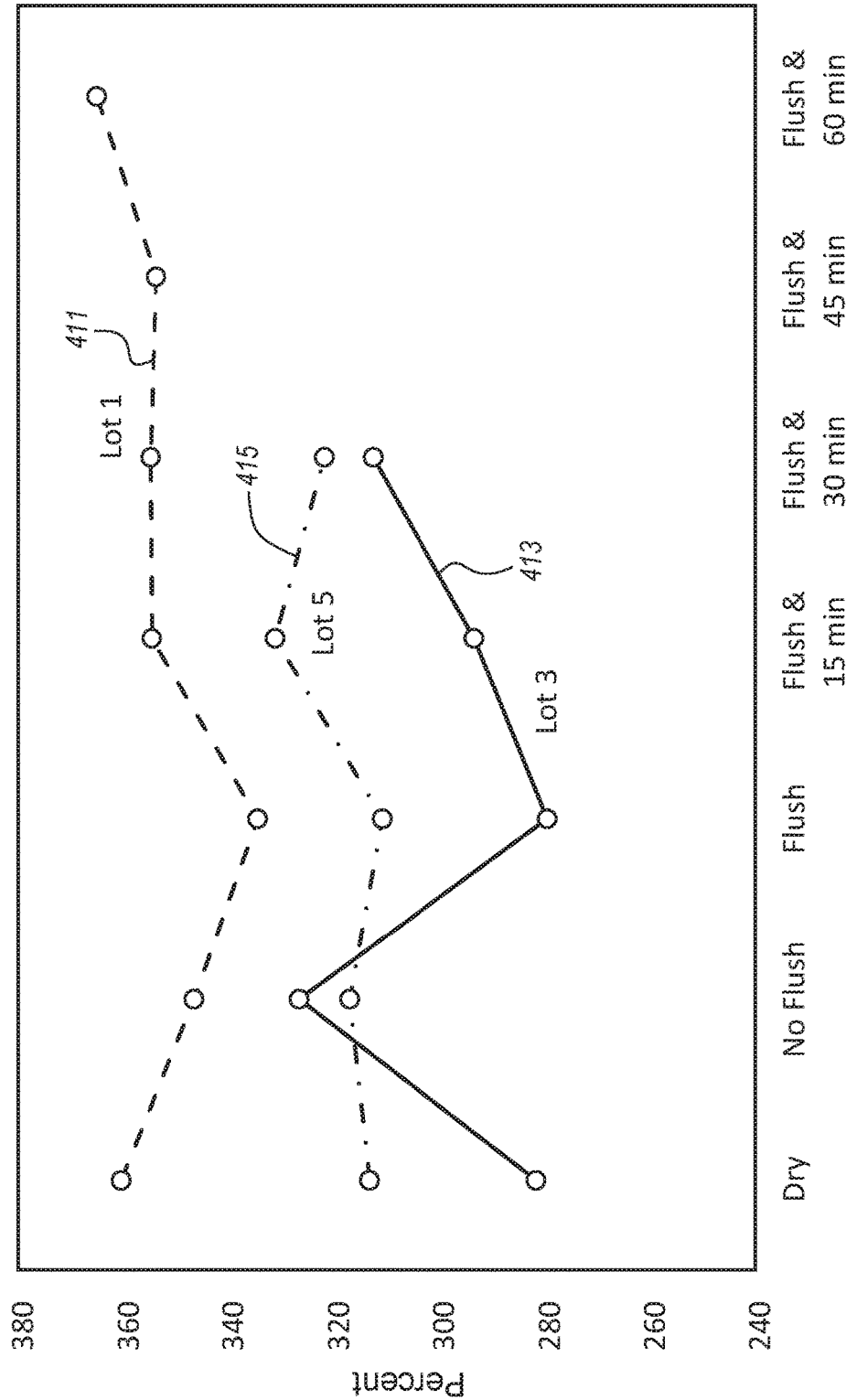
FIGS. 5A-5C are plots of strains at break, or ultimate elongations, exhibited by various sections cut from catheter shafts of the form depicted in FIGS. 1, 2A, and 2B, which catheter shafts were extruded from different embodiments of siliconized polycarbonate polyurethanes according to the present disclosure.
Figure 5B:
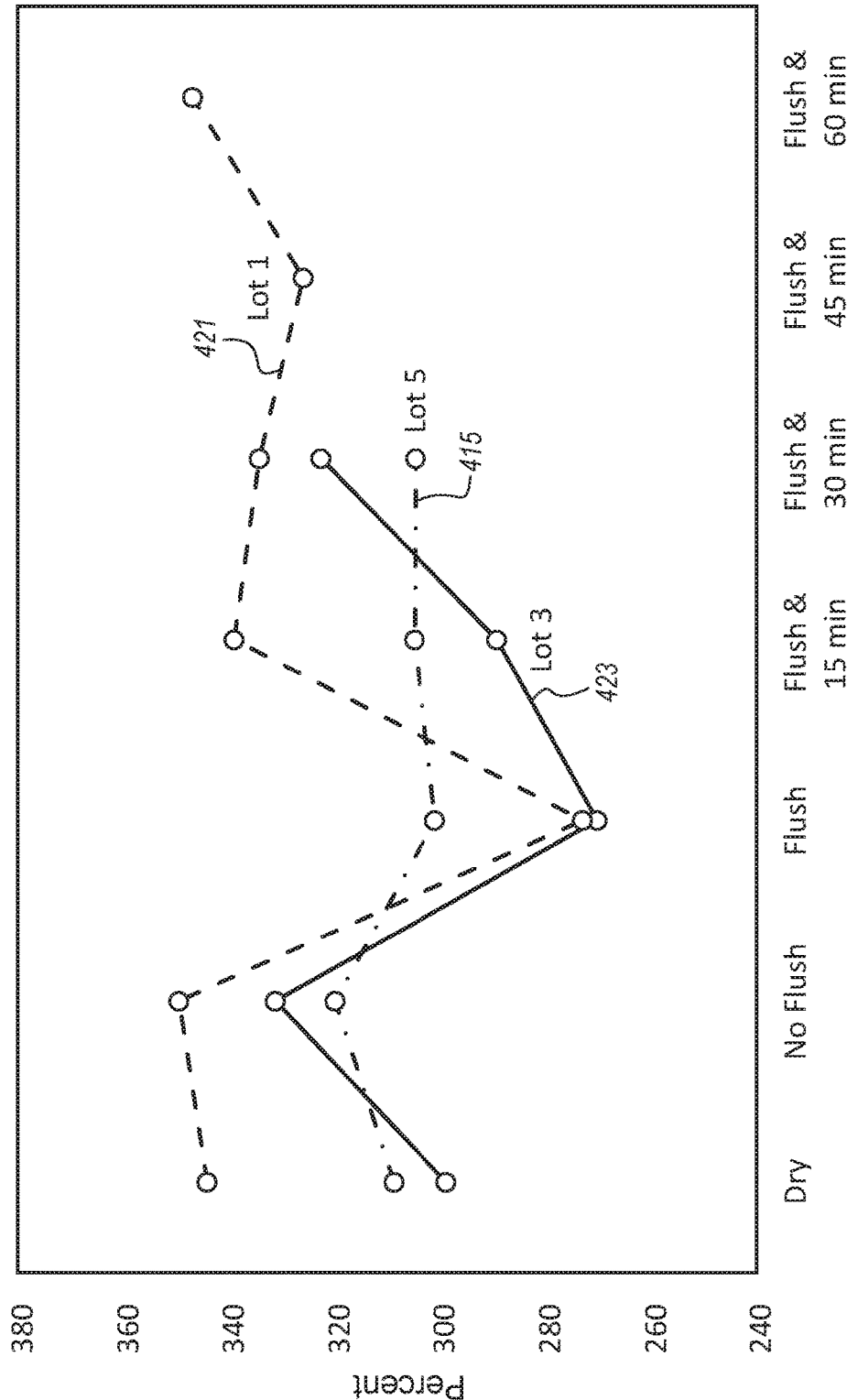
Figure 5C:
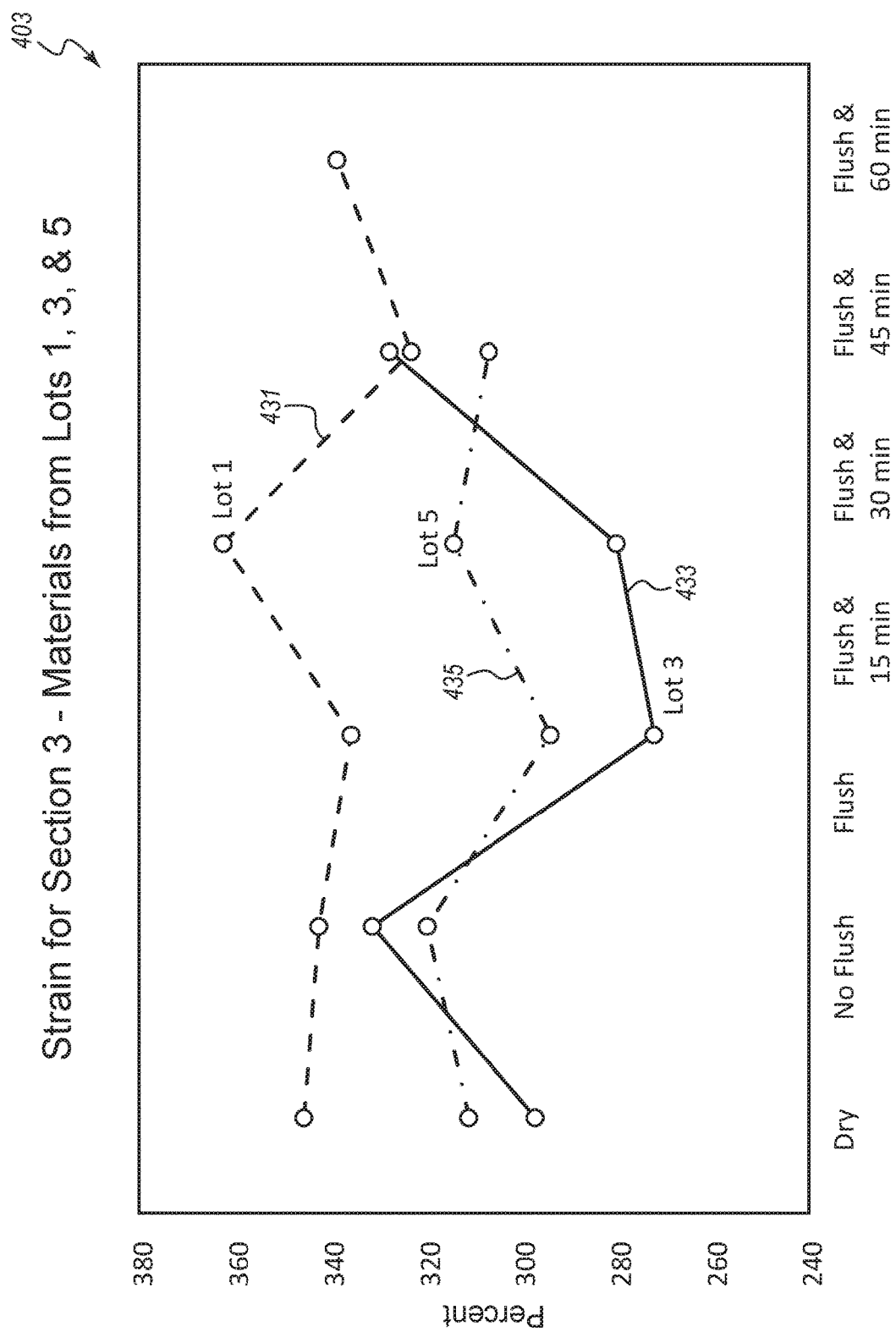

FIGS. 5A-5C also reveal surprising results with respect to the material of Lot 3. Polyurethane performance typically degrades when subjected to aqueous environments at elevated temperatures. The material of Lot 3, however, showed consistently and significantly improved strain after being subjected to the No Flush condition (i.e., after having been soaked in a saline solution at 37° C.). This result was either less pronounced or nonexistent with the catheter shafts formed from the materials of Lots 1 and 5. Moreover, the material of Lot 3 rapidly recovered from the Flush condition (i.e., recovered quickly from alcohol locking).

Example 4

Test catheters were formed from three different materials of similar hardness for purposes of comparison. The first material was formed of approximately 69 wt % of a catheter-grade aliphatic polyether polyurethane sold under the trademark QUADRAFLEX®, which is available from Biomerics, which was compounded with 30 wt % barium sulfate and approximately 1 wt % colorant. The second material was formed of 69 wt % of a catheter-grade aromatic polycarbonate polyurethane formed of poly(hexamethylene carbonate) diol, methylene diphenyl diisocyanate, and 1,4-butanediol, which was compounded with 30 wt % barium sulfate and 1 wt % colorant. The third material was a quantity of Lot 3, as described above with respect to Example 2, and thus included 69.1 wt % of the Sample 3 siliconized aromatic polycarbonate polyurethane described with respect to Example 1, 29.6 wt % barium sulfate, and 1.3 wt % colorant. Each test catheter included a catheter shaft and a luer connector of the same configuration described above with respect to Example 2. The catheters were subjected to preconditioning such as described above with respect to Example 2 and then tested for burst pressure.

Figure 6:
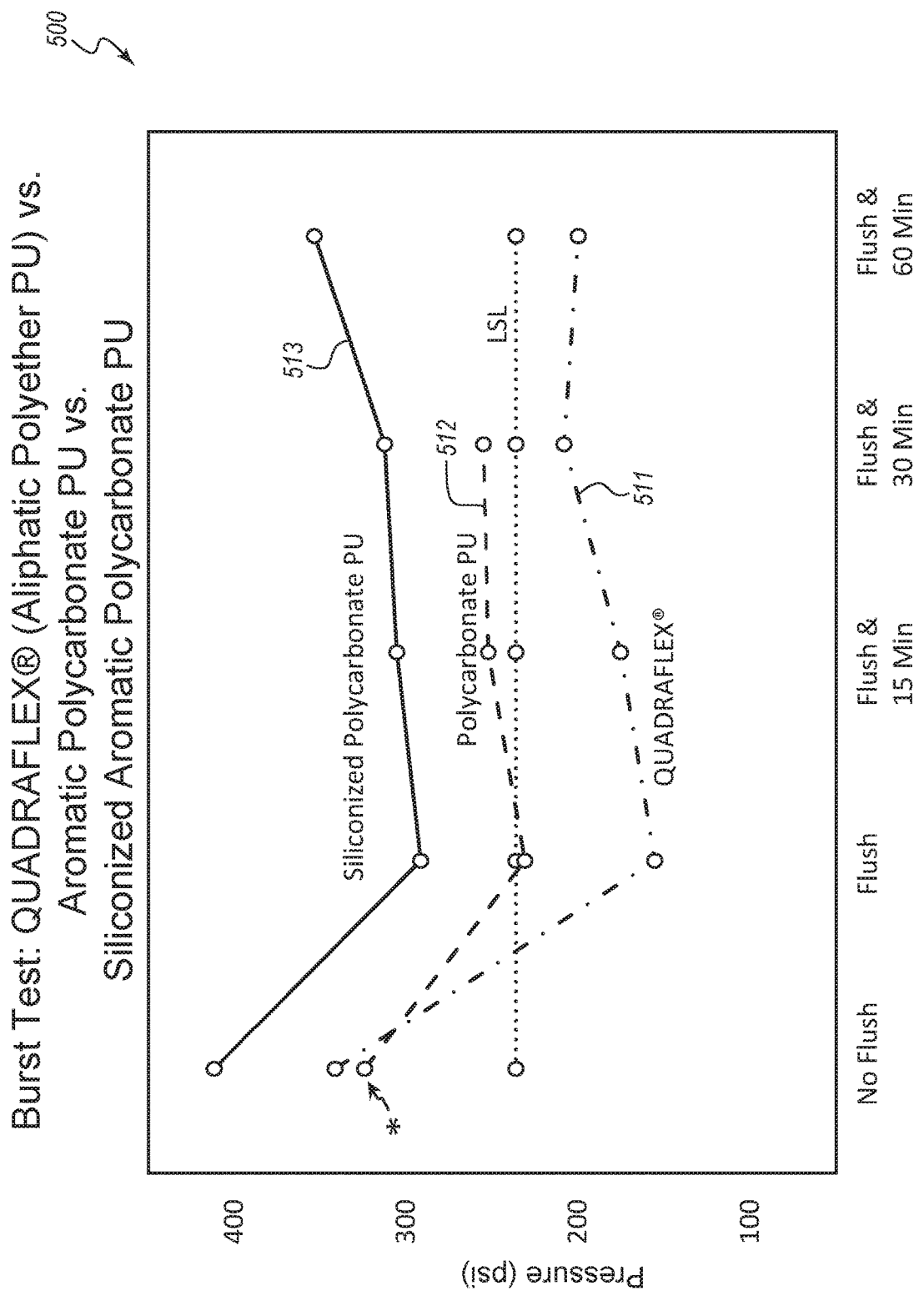
FIG. 6 is a plot of burst pressures exhibited by various catheters that comprised catheter shafts of the form depicted in FIGS. 1, 2A, and 2B, which catheter shafts were extruded from an aliphatic polyether polyurethane, an aromatic polycarbonate polyurethane, and an embodiment of siliconized polycarbonate polyurethane according to the present disclosure.

FIG. 6 provides a plot 500 of the test results. For each data point, from three to six catheters were tested and the average thereof is shown, except for the data point identified with an asterisk (for which a single catheter was tested). Separate curves 511, 512, 513 connect the data points for the catheters associated with the QUADRAFLEX®, the aromatic polycarbonate polyurethane, and the Lot 3 materials, respectively. A further "lower spec limit" (LSL) at 236 psi is also shown, which represents a pressure at which certain catheters may be expected or required to perform without bursting in order to be considered power injectable, in some instances. The conditions identified as No Flush, Flush, and Flush & ## Min on the horizontal axis of plot 500 are the same as the identically named conditions described above with respect to Example 2. As with the plots in FIGS. 3-5C, the horizontal axis is not, in all instances, accurately scaled with respect to time.

It is readily apparent that the siliconized aromatic polycarbonate polyurethane significantly outperformed the aromatic polycarbonate polyurethane and the aliphatic polyether polyurethane. These results also indicate that catheters formed of the siliconized aromatic polycarbonate could withstand the rigors of power injection, even after an alcohol lock event.

Example 5

Various quantities of Lot 3, as described in Example 2 above, were used to perform a series of analytical tests on the material, the results of which are provided in Table 4, below. The tests were performed according to the ASTM standards identified in Table 4. Although the measured values are not expressed with a specified level of uncertainty, it is understood that at least some uncertainty of these values is present. Thus, each value may be bracketed by a small range of values. Moreover, as previously discussed, a range of acceptable values are also possible for the raw materials, such that a concomitant range of the values measured in Table 4 is also contemplated.

TABLE 4

Analysis of Lot 3 Material

| Test Description | Test Standard | Units | Measured Value |
|---|---|---|---|
| Melt Flow Rate | ASTM D1238 | g/10 min | 8.9 |
| Specific Gravity | ASTM D792 | unitless | 1.529 |
| Shore Hardness (A) (Durometer) | ASTM D2240 | Shore A | 97 |
| Ash Test (Barium Sulfate Content) | ASTM D5630 | % | 30.2 |
| Stress @ 100% (Tensile @ 100%) | ASTM 412 | psi | 2,445 |
| Ultimate Elongation | ASTM 412 | % | 394 |
| Ultimate Tensile Strength | ASTM 412 | psi | 3,899 |

IV. PICC Devices

Figure 7:
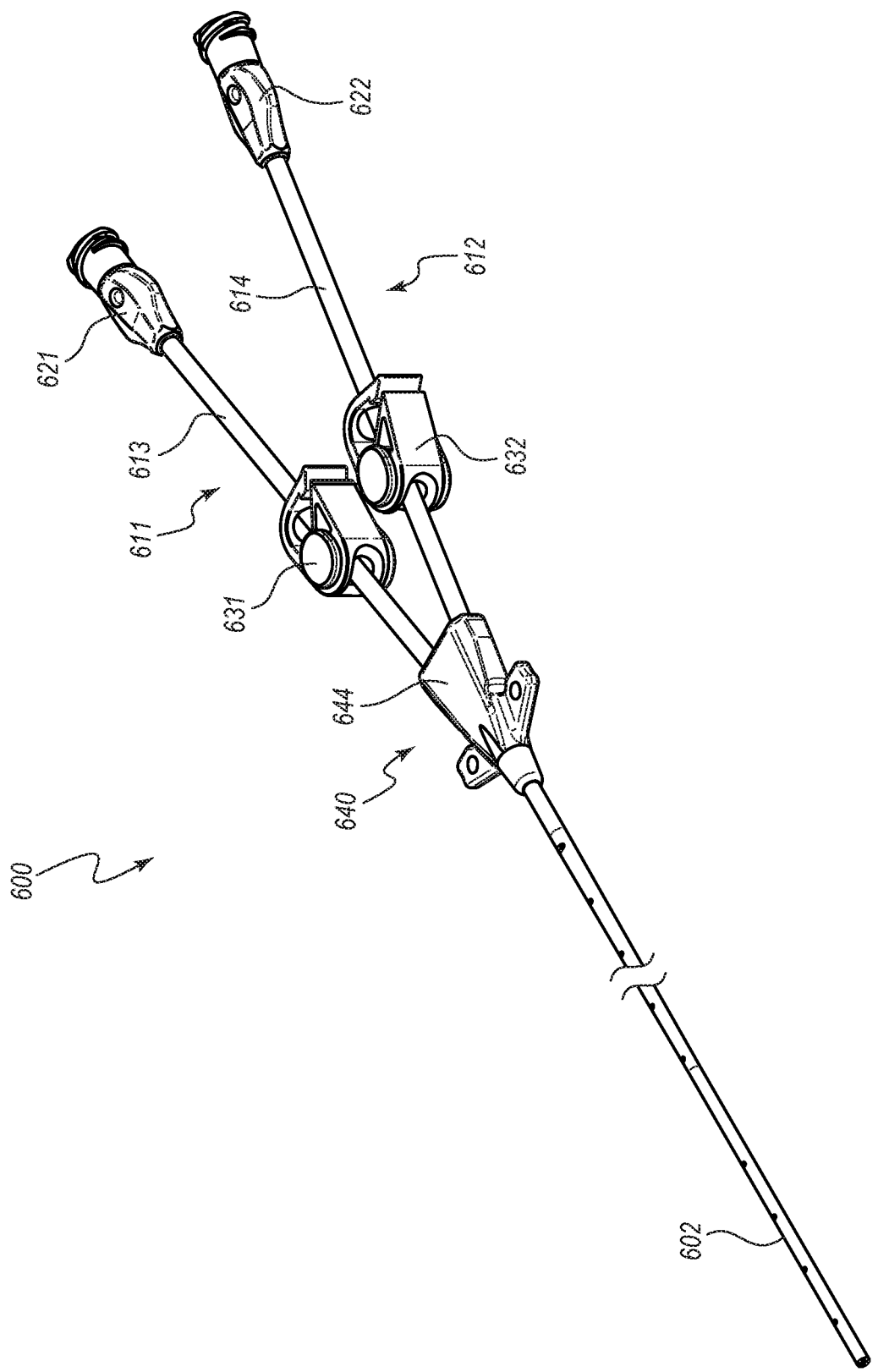
FIG. 7 is a perspective view of an embodiment of a peripherally inserted central catheter (PICC) device, or assembly, that includes a catheter shaft of the form depicted in FIGS. 1, 2A, and 2B connected to extension legs via a two-part, or two-layer, overmolded junction hub, wherein each of the catheter shaft, the extension legs, and the two layers of the junction hub includes one or more embodiments of siliconized polycarbonate polyurethanes according to the present disclosure.

FIG. 7 is a perspective view depicting an illustrative embodiment of a catheter device 600 that can be constructed using embodiments of the present disclosure. The illustrated PICC device 600 is specifically a power-injectable dual-lumen PICC, and thus may also be referred to herein as a PICC device or PICC assembly. The catheter device 600 is merely illustrative of various forms of catheter devices that may be constructed, at least in part, from embodiments of materials disclosed herein. For example, in other instances, catheter devices similar to that depicted in FIG. 7 may include different numbers of extension legs and lumens, may have a catheter shaft with different dimensions (e.g., larger or smaller outer diameter, wall thickness, septum thickness, length), etc. More generally, the PICC device 600 is illustrative of various forms of medical devices that may be constructed, at least in part, from embodiments of materials disclosed herein. Other suitable medical devices may include, for example, any of a variety of implantable devices, such as implantable vascular access ports.

In the illustrated embodiment, the PICC device 600 includes a dual-lumen catheter shaft 602, extension legs 611, 612, and a junction hub 640. The long, insertable distal portion of the catheter shaft 602, which is also referred to herein as the reduced diameter portion 114 (see FIG. 1), is substantially uniform along its full length and may be trimmed to a desired length for accurate placement at a target region with the anatomy of the patient. This region may include markings to assist with the accuracy of such trimming.

The extension legs 611, 612 include extension tubes 613, 614, respectively, which are each in fluid communication with a separate catheter shaft lumen. The extension legs 611, 612 further each include a female luer connector 621, 622 at the proximal end of each extension tube 613, 614 and a clamp 631, 632 disposed on each extension tube 613, 614. The junction hub 640 connects the extension legs 611, 612 to the catheter shaft 602. The junction hub 640 is formed in two parts. In particular, the junction hub 640 includes a junction core 642 (see FIG. 8B) and a junction cover 644. In various embodiments, at least the catheter shaft 602, the extension legs 611, 612, the junction core 642, and the junction cover 644 are formed of embodiments of the siliconized polycarbonate polyurethanes of the present disclosure. Any combination of the formulations for the siliconized polycarbonate polyurethanes disclosed herein are contemplated.

Figure 8A:
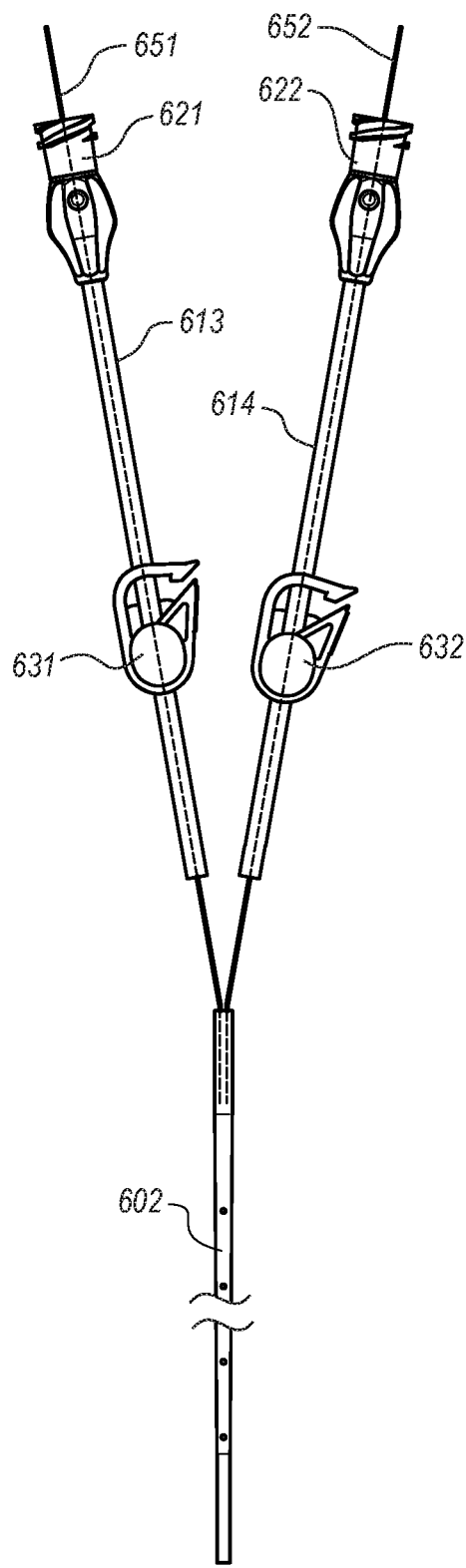
FIGS. 8A-8C are schematic plan views that depict successive stages in an illustrative process for connecting the catheter shaft and the extension legs of FIG. 1 via the two-part junction hub.
Figure 8B:
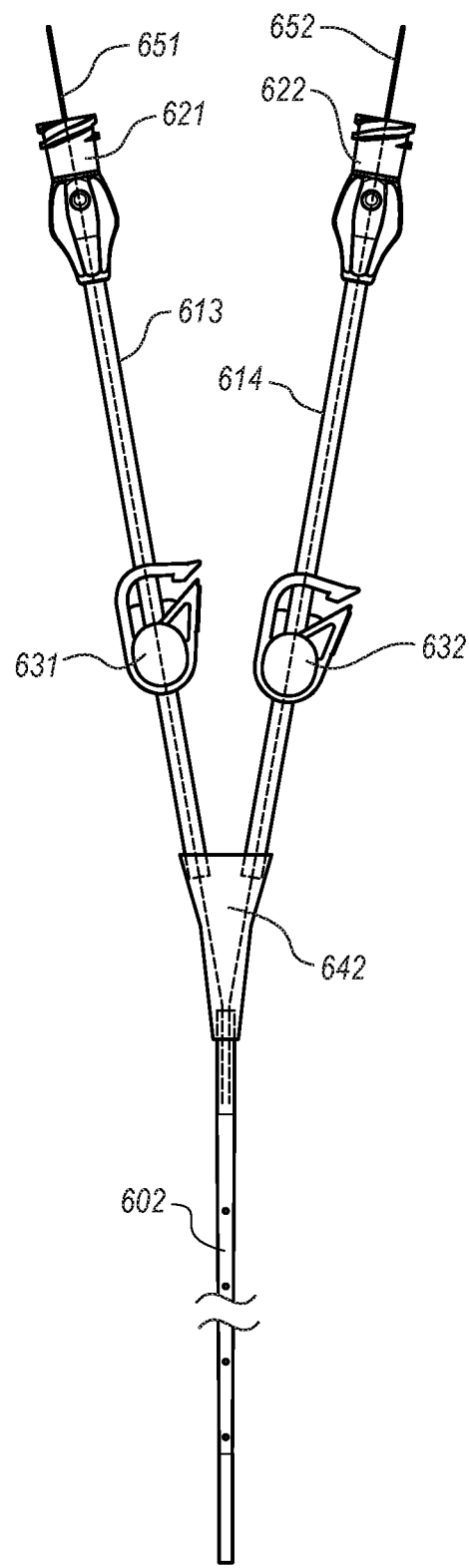
Figure 8C:
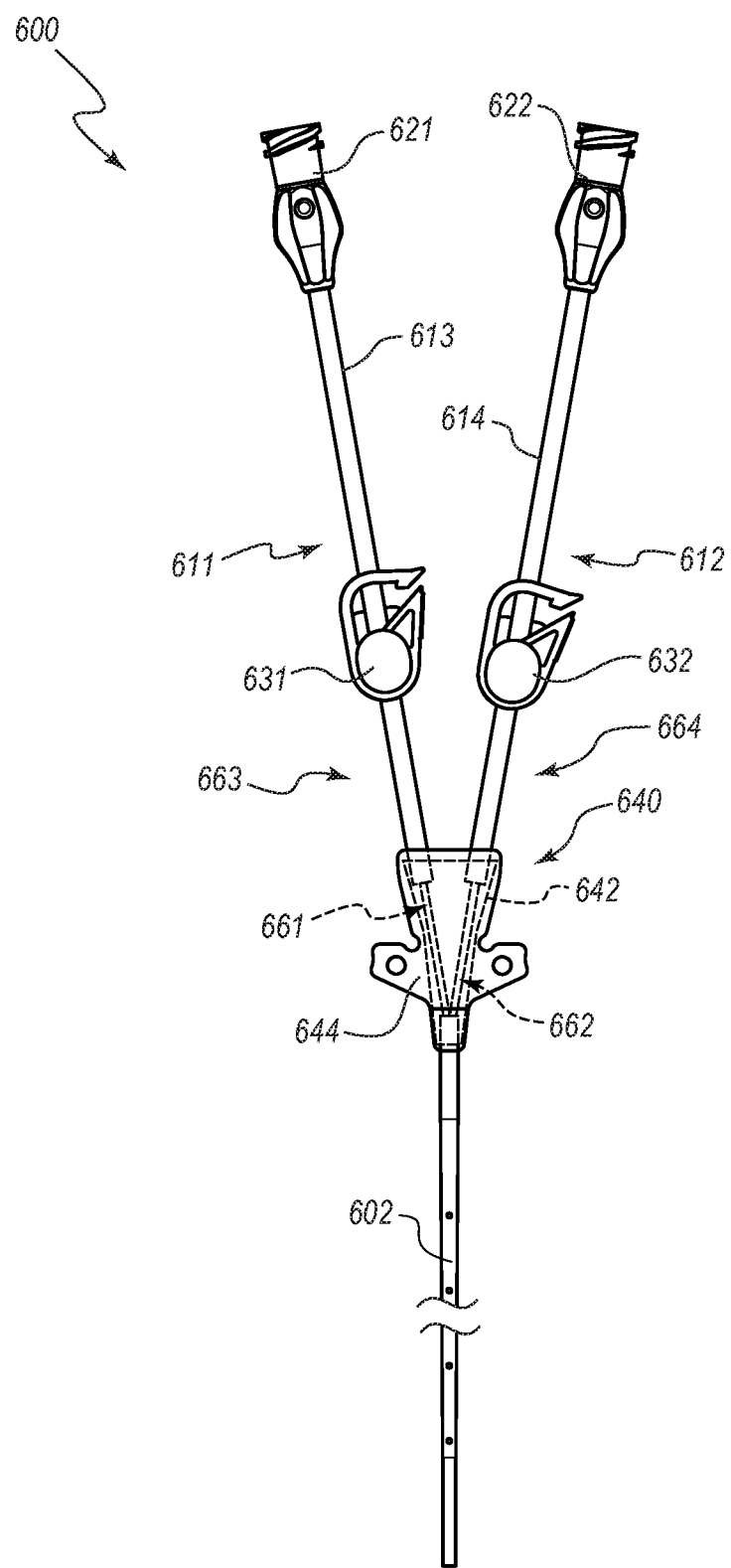

FIGS. 8A-8C depict various stages of an illustrative process for assembling or manufacturing the PICC device 600. Prior to the stage depicted in FIG. 8A, the luer connectors 621, 622 are overmolded onto the proximal ends of the extension tubes 613, 614 using, for example, techniques and equipment commonly known in the art, and the clamps 631, 632 can be advanced over the distal ends of the extension tubes 613, 614. As shown in FIG. 8A, core pins 651, 652 can be inserted through the extension tubes 613, 614 and into the respective lumens of the catheter shaft 602. The lumens are like the lumens 122, 124 of the catheter shaft 100, as depicted in FIGS. 2A and 2B.

With reference to FIG. 8B, the junction core 642 can be overmolded onto the proximal end of the catheter shaft 602 and onto the distal ends of the extension tubes 613, 614. With reference to FIG. 8C, the junction cover 644 can then be overmolded onto the junction core 642, the proximal end of the catheter shaft 602, and the distal ends of the extension tubes 613, 614. The core pins 651, 652 can then be removed proximally through the extension tubes 613, 614, leaving behind fluid passages or channels 661, 662 through the junction core 642 that each fluidly connect one of the extension tubes 613, 614 to a respective one of the lumens of the catheter shaft 602.

Once the PICC device 600 has been formed, it includes two fluid paths 663, 664 along which fluid can be introduced into and/or removed from a patient. The fluid path 663 passes through the extension leg 611, the junction hub 640, and the catheter shaft 602. Stated otherwise, the fluid path 663 includes a fluid passage through the connector 621, a lumen of the extension tube 613, the channel 661 through the junction hub 640, and one of the two lumens of the catheter shaft 602. Similarly, the fluid path 664 passes through extension leg 612, the junction hub 640, and the catheter shaft 602. Stated otherwise, the fluid path 664 includes a fluid passage through the connector 622, a lumen of the extension tube 614, the channel 662 through the junction hub 640, and the other of the two lumens of the catheter shaft 602.

In some embodiments, a single-layer or one-shot junction hub 640 may alternatively be used. The two-layer or two-shot junction hub 640 of the present example, however, may be advantageous for certain applications. For example, in some instances, such as in power injection applications, it can be desirable for the junction core 642 to be significantly harder than the material of the extension tubes 613, 614 and/or the catheter shaft 602. During power injections, pressures can be more elevated toward the proximal region of the PICC device 600, and can decrease in the distal direction toward a minimum at the distal end of the catheter shaft 602. A harder junction core 642 can readily withstand these elevated pressures in the proximal region, and can be more resistant to swelling. Moreover, a harder junction core 642 can be more resistant to alcohol exposure during an alcohol lock event.

In further instances, it can be desirable to include the softer junction cover 644, particularly in instances where a hard junction core 642 is used. The junction cover can render the junction 640 more comfortable for a patient. This may, in some instances, be of particular utility with respect to PICC catheters, where the patient may often come into contact with the exposed junction 640 during the extended periods over which PICCs are typically used. In some instances, the junction cover 644 may not only be softer than the junction core 642, but may likewise be softer than the extension tubes 613, 614 and/or the catheter shaft 602.

In some instances, the catheter shaft 602 and the extension tubes 613, 614 may be formed of the same material and/or may have the same hardness. For example, in some instances, the catheter shaft 602 and the extension tube 613, 614 may be formed of materials that have identical chemical formulations. In further instances, the materials may not be compounded with any additives, or may be physically compounded with identical additives.

In other instances, the catheter shaft 602 and the extension tubes 613, 614 may be formed of different materials and/or may have different hardness values. For example, in some embodiments, the extension tubes 613, 614 may be formed of a siliconized polycarbonate polyurethane that has a relatively greater proportion of hard segment than does a siliconized polycarbonate polyurethane of which the catheter shaft 602 is formed. Stated otherwise, the extension tubes 613, 614 may be formed of a siliconized polycarbonate polyurethane having a different chemical formulation than that of a siliconized polycarbonate polyurethane of which the catheter shaft 602 is formed. In some instances, when a harder material is used for the extension tubes 613, 614, the extension tubes may, in some instances, thereby better withstand deformations from repeated and/or prolonged closure of the clamps 631, 632. In other or further embodiments, harder extension tubes 613, 614 may better withstand elevated pressures than may be experienced by at least a proximal end of the catheter shaft 602, depending on the overall configuration of the PICC device 600 and/or that of the catheter shaft 602.

In some instances, the material of the catheter shaft 602 and that of the extension tubes 613, 614 can vary with respect to the additives contained therein. For example, in some embodiments, the catheter shaft 602 may be compounded with one or more radiopacifiers, whereas the material of the extension tubes 613, 614 may not. Further, the catheter shaft 602 and one or more of the extension tubes 613, 614 may be compounded with different types and/or amounts of colorants. For example, in some embodiments, the extension tubes 613, 614 and the catheter shaft 602 may be formed of siliconized polycarbonate polyurethanes that have identical chemical formulations, but differ with respect to the presence or absence of additives that have been physically compounded therewith. In other instances, the chemical formulations of the siliconized polycarbonate polyurethanes can be different, and in further instances, these polyurethanes are physically compounded with different types and/or amounts of colorants and/or other additives In some instances, the extension tubes 613, 614 are formed of the same material, which may or may not be the same material as that which is used for the catheter shaft 602. In other embodiments, each extension tube 613, 614 is formed of a different material. For example, in some embodiments, one extension tube 613 is formed of a siliconized polycarbonate polyurethane having a first chemical formulation, and the other extension tube 614 is formed of a siliconized polycarbonate polyurethane having a second chemical formulation. In some instances, the first and second chemical formulations are identical to each other, but the polyurethanes are physically compounded with different types and/or amounts of colorants and/or other additives. For example, the extension tubes 613, 614 may be colored differently to signify different functionalities or designations for each extension tube 613, 614 (e.g., one extension tube 613, 614 may be designated for power injections, whereas the other may not). In other instances, the first and second chemical formulations can be different, and in further instances, the polyurethanes are physically compounded with different types and/or amounts of colorants and/or other additives.

Where the junction core 642 is joined to the catheter shaft 602 and the extension tubes 613, 614 via overmolding, as in the illustrated embodiment, it can be desirable to ensure overmolding compatibility of the materials from which these components are formed. In particular, the materials should be capable of securely bonding to each other during overmolding. Stated otherwise, as the molten junction core 642 material is introduced around the tips of the catheter shaft 602 and the extension tubes 613, 614 at elevated temperatures, the various materials that come into contact with each other should be readily able to flow together and harden into a secure bond when cooled. For power injectable catheters, these bonds should be capable of withstanding high pressures, or stated otherwise, the bonds should be leak-proof at the elevated pressures associated with power injection.

In certain embodiments, the catheter shaft 602, the extension tubes 613, 614, and the junction core 642 are formed of the same or different embodiments of siliconized polycarbonate polyurethanes according to the present disclosure. For example, in some embodiments, the catheter shaft 602 and the extension tubes 613, 614 can each include the same siliconized polycarbonate polyurethane material, or stated otherwise, the polyurethane component of each material can have the same chemical formulation. In further embodiments, the siliconized polycarbonate polyurethane of the catheter shaft 602 may be compounded with a radiopacifier and a first amount of colorant, and optionally other additives, whereas the same siliconized polycarbonate polyurethane of the extension tubes 613, 614 may not be compounded with any radiopacifiers, but may be compounded with a second amount of colorant, and optionally other additives. In various embodiments, the first and second amounts of colorant may be different. For example, in some instances, the first amount of colorant is greater than the second amount of colorant, and as a result, the catheter shaft 602 may be opaque, whereas the extension tubes 613, 614 may be transparent or translucent. In further embodiments, different types of colorants may be used to achieve different hues.

In further embodiments, the junction core 642 is formed of a different embodiment of the siliconized polycarbonate polyurethane according to the present disclosure. Stated otherwise, the siliconized polycarbonate polyurethane of the junction core 642 may have a different chemical formulation than that of one or more of the extension tubes 613, 614 and/or the catheter shaft 602. For example, the siliconized polycarbonate polyurethane may have a higher hard segment content, or stated otherwise, the isocyanate and the chain extender may be present in greater relative amounts for the junction core 642. In some embodiments, although the soft segment is thus present in a smaller amount for the junction core 642, the relative content of the soft segment may be substantially the same as that of the soft segment of the material used for the catheter shaft 602 and the extension tubes 613, 614. Stated otherwise, in the chemical formulations for the different siliconized polycarbonate polyurethanes, the percentage by weight of the polysiloxane relative to the total weight of the polysiloxane and polycarbonate may be substantially the same. In various embodiments, the percentage by weight of the polysiloxane relative to the soft component can vary between the different materials by an amount no greater than about 0.1, 0.2, 0.3, 0.4, 0.5, 0.75, 1, 1.5, 2, 3, or 5 percent. In certain embodiments, similar polysiloxane contents, relative to the soft segment, can yield strong and reliable bonds between the different siliconized polycarbonate polyurethanes, such as may be particularly well suited to withstand elevated pressures during power injection.

In still further embodiments, the junction cover 644 is formed of a different embodiment of the siliconized polycarbonate polyurethane according to the present disclosure, as compared with that of the junction core 642 and/or one or more of the catheter shaft 602 and the extension tubes 613, 614. For example, the siliconized polycarbonate polyurethane of the junction cover 644 may have a lower hard segment content than each of the other siliconized polycarbonate polyurethanes, or stated otherwise, the isocyanate and the chain extender may be present in smaller relative amounts for the junction cover 644. In some embodiments, although the soft segment is thus present in a greater amount, the relative content of the soft segment may be substantially the same as that of the soft segment of the material used for the junction core 642, the catheter shaft 602, and/or the extension tubes 613, 614. Stated otherwise, in the formulations for the various siliconized polycarbonate polyurethanes, the percentage by weight of the polysiloxane relative to the total weight of the polysiloxane and polycarbonate may be substantially the same among the various materials. In various embodiments of the PICC device 600, the percentage by weight of the polysiloxane relative to the soft component can vary between any two different materials by an amount no greater than about 0.1, 0.2, 0.3, 0.4, 0.5, 0.75, 1, 1.5, 2, 3, or 5 percent, and may vary among all of the different materials by an amount no greater than about 0.1, 0.2, 0.3, 0.4, 0.5, 0.75, 1, 1.5, 2, 3, 5, 7.5, or 10 percent. In certain embodiments, similar polysiloxane contents, relative to the soft segment, can yield strong and reliable bonds between the different siliconized polycarbonate polyurethanes, such as may be particularly well suited to withstand elevated pressures during power injection. The bonds may also ensure a reliable soft-touch covering for the junction core 642 that will remain reliably attached thereto.

In other or further embodiments, the siliconized polycarbonate polyurethanes of the various components (extension tubes, catheter shaft, junction core, and/or junction cover) can also have a range of durometer values. In various examples, the siliconized polycarbonate polyurethane of the catheter shaft can have a Shore A durometer value of from about 65 to about 100, from about 70 to about 90, from about 75 to about 85, from about 91 to about 100, from about 94 to about 98, from about 96 to about 100, from about 95 to about 99, from about 96 to about 98, or from about 97 to about 100 (including to a hardness slightly off the high end of the Shore A scale, or harder than 100). In other or further examples, the siliconized polycarbonate polyurethane of the junction core can have a Shore D durometer value of from about 15 to about 85, from about 60 to about 80, or from about 65 to about 75. In still other or further embodiments, the siliconized polycarbonate polyurethane of the junction cover can have a Shore A durometer value of from about 65 to about 100, from about 70 to about 90, from about 75 to about 85, or from about 90 to about 100.

In other or further embodiments, only a portion of one or more of the components comprises a siliconized polycarbonate polyurethane. For example, in some embodiments, the catheter shaft 602 may generally be formed of a different material (e.g., a different type of polyurethane), and the inner surfaces of the lumens may be coated with an embodiment of the siliconized polycarbonate polyurethane. In other or further embodiments, the catheter shaft 602 may be formed as a coextrusion of a siliconized polycarbonate polyurethane and a different type of polyurethane.

The luer connectors 621, 622 may be formed of any suitable material, and may in some instances be overmolded to the proximal ends of the extension tubes 613, 614. In some embodiments, the connectors 621, 622 may be formed of a rigid thermoplastic polyurethane such as, for example, QUADRAPLAST®, available from Biomerics. The thermoformed bond between the connectors 621, 622 and the extension tubes 613, 614 may desirably sufficiently strong to withstand elevated pressures associated with power injection.

Example 6

In one example, the PICC device 600 includes a catheter shaft 602 of the same form described above with respect to Example 2 and depicted in FIGS. 1, 2A, and 2B. In particular, with reference to FIG. 1, the various identified dimensions of the catheter shaft 602 are as follows: $L_C$ is between 0.35 inches and 0.51 inches, $L_T$ is no greater than 2.0 inches (typically between 1.3 inches and 1.6 inches), and $L_E$ is approximately 22.4 inches (typically between 22.3 and 22.5 inches; i.e., approximately 57.0 centimeters, and typically between 56.8 and 57.2 centimeters). With reference to FIG. 2A, the various identified dimensions of the connection region 110 are as follows: $W_{SW1}$ is no less than 0.007 inches, $W_{IW1}$ is no less than 0.007 inches, and $OD_1$ is 0.092 inches (+0.002/−0.003 inches). With reference to FIG. 2B, the various identified dimensions of the reduced diameter region 114 are as follows: $W_{SW2}$ is no less than 0.004 inches (generally about 0.007 inches), $W_{IW2}$ is no less than 0.005 inches, and $OD_2$ is 0.069 inches (+0.002/−0.003 inches).

The PICC device 600 further includes substantially identical extension tubes 613, 614, each of which defines a substantially cylindrical hollow tube having an inner diameter of 0.066±0.002 inches and an outer diameter of 0.106±0.003 inches. The extension tubes 613, 614 are initially extruded into long tubes that are cut to length of 3.75 inches prior to being overmolded with the luer connectors 621, 622 at their proximal ends and the junction core 642 at their distal ends. After overmolding, the exposed length is within a range of from 2.75 inches to 3.25 inches (typically 2.9±0.03 inches).

The clamps 631, 632 are formed of a rigid plastic. The clamps 631, 632 each include a flexible latching arm via which selective opening and closure of the extension tubes 613, 614 is achieved. The clamps 631, 632 close the extension tube 613, 614 by compressing and deforming the tubes to pinch them shut and the clamps are locked (in a selectively releasable manner) to maintain the tubes in the deformed, closed condition.

The catheter shaft 602, the extension tubes 613, 614, the junction core 642, and the junction cover 644 are each formed of materials that include embodiments of siliconized polycarbonate polyurethanes according to the present disclosure. The materials were manufactured using the raw materials and processes described in Example 1 and, where applicable, the additional processes described in Example 2, above. The GLYCOLUBE™ VL additive, however, was added during polymerization, but does not participate in the reaction. Rather, this additive is dispersed throughout the mixture during polymerization and ends up physically blended into the cured polymer. The materials for the catheter shaft 602 and the extension tubes 613, 614 each include the siliconized polycarbonate polyurethane identified as Sample 3 in Example 1, above. Further, the material designated as Lot 3 in Example 2, above, was used for the catheter shaft 602. The formulations for the materials are provided in Table 5, below.

TABLE 5

Siliconized Polycarbonate Polyurethane

| Component | Measurement Description | Polycarbonate diol Soft Segment | PDMS Soft Segment | MDI Hard Segment | BDO Hard Segment | Isocyanate Index | Hardness (Shore Durometer) | Siliconized Polycarbonate Polyurethane (wt %) | Barium Sulfate (wt %) | Colorant (wt %) | GLYCOLUBE™ VL (wt %) |
|---|---|---|---|---|---|---|---|---|---|---|---|
| Catheter Shaft | individual wt % | 50.4 | 5.7 | 34.6 | 9.3 | 1.015 | 97A | 69.1 | 29.6 | 1.3 | 0 |
|  | wt % of polyol component | 89.8 | 10.2 | n/a | n/a |  |  |  |  |  |  |
|  | soft segment wt % vs. hard segment wt % | 56.1 |  | 43.9 |  |  |  |  |  |  |  |
| Extension Tubes | individual wt % | 50.4 | 5.7 | 34.6 | 9.3 | 1.015 | 97A | 99.6 | 0 | 0.1 | 0.3 |
|  | wt % of polyol component | 89.8 | 10.2 | n/a | n/a |  |  |  |  |  |  |
|  | soft segment wt % vs. hard segment wt % | 56.1 |  | 43.9 |  |  |  |  |  |  |  |
| Junction Core | individual wt % | 44.5 | 5.0 | 39.3 | 11.2 | 1.023 | 71D | 99.7 | 0 | 0 | 0.3 |
|  | wt % of polyol component | 89.9 | 10.1 | n/a | n/a |  |  |  |  |  |  |
|  | soft segment wt % vs. hard segment wt % | 49.5 |  | 50.5 |  |  |  |  |  |  |  |
| Junction Cover | individual wt % | 61.8 | 6.9 | 25.8 | 5.6 | 1.022 | 81A | 99.2 | 0 | 0.5 | 0.3 |
|  | wt % of polyol component | 90.0 | 10.0 | n/a | n/a |  |  |  |  |  |  |
|  | soft segment wt % vs. hard segment wt % | 68.7 |  | 31.3 |  |  |  |  |  |  |  |

Various properties of the compounded materials identified in Table 5 are listed in Table 6, below. These properties were measured on quantities of the materials that had not been extruded into the tubes or shafts and had not been overmolded, or stated otherwise, were not formed into any of the PICC device components. For each property, the tests were performed according to the ASTM standards identified in Table 6. Although the measured values are not expressed with a specified level of uncertainty, it is understood that at least some uncertainty of these values is present. Thus, each value may be bracketed by a small range of values. Moreover, a range of acceptable values is also possible for the raw materials, such that a concomitant range of the values measured in Table 6 is also contemplated. For example, the concentration of barium sulfate can be present in an amount of 29.6±2 wt %, and the amounts of the remaining components can be adjusted accordingly. Stated otherwise, in some instances, a target amount (e.g., the amount set forth a specification for formulating the final product) of the barium sulfate is 29.6 wt % with a tolerance of ±2 wt %.

TABLE 6

| Compounded Material (Identified by Associated PICC Component) | Test Description | Test Standard | Units | Measured Value |
|---|---|---|---|---|
| Catheter Shaft | Melt Flow Rate | ASTM D1238 | g/10 min | 8.9 |
| | Specific Gravity | ASTM D792 | unitless | 1.529 |
| | Shore Hardness (A) (Durometer) | ASTM D2240 | Shore A | 97 |
| | Ash Test (Barium Sulfate Content) | ASTM D5630 | % | 30.2 |
| | Stress @ 100% (Tensile @ 100%) | ASTM 412 | psi | 2,445 |
| | Ultimate Elongation | ASTM 412 | % | 394 |
| | Ultimate Tensile Strength | ASTM 412 | psi | 3,899 |
| Extension Tubes | Melt Flow Rate | ASTM D1238 | g/10 min | 1.9 |
| | Specific Gravity | ASTM D792 | unitless | 1.201 |
| | Shore Hardness (A) (Durometer) | ASTM D2240 | Shore A | 96 |
| | Stress @ 100% (Tensile @ 100%) | ASTM 412 | psi | 2,551 |
| | Ultimate Elongation | ASTM 412 | % | 417 |
| | Ultimate Tensile Strength | ASTM 412 | psi | 6,535 |
| Junction Core | Melt Flow Rate | ASTM D1238 | g/10 min | 0.7 |
| | Specific Gravity | ASTM D792 | unitless | 1.197 |
| | Shore Hardness (D) (Durometer) | ASTM D2240 | Shore D | 71 |
| | Stress @ 100% (Tensile @ 100%) | ASTM 412 | psi | 4,760 |
| | Ultimate Elongation | ASTM 412 | % | 172 |
| | Ultimate Tensile Strength | ASTM 412 | psi | 7,325 |
| Junction Cover | Melt Flow Rate | ASTM D1238 | g/10 min | 6.0 |
| | Specific Gravity | ASTM D792 | unitless | 1.176 |
| | Shore Hardness (A) (Durometer) | ASTM D2240 | Shore A | 81 |
| | Stress @ 100% (Tensile @ 100%) | ASTM 412 | psi | 943 |
| | Ultimate Elongation | ASTM 412 | % | 240 |
| | Ultimate Tensile Strength | ASTM 412 | psi | 3,452 |

Example 7

A first test group (Group 1) of 40 PICC devices according to the specifications of Example 6 were assembled and then sterilized via standard ethylene oxide sterilization techniques (referred to herein as sterilization conditioning). The PICC devices were then subjected to thermal conditioning according to standard ASTM D4332-14 at the following parameters: −18±2° C. at uncontrolled relative humidity for 72 hours minimum; 23° C.±5° C. at 50% relative humidity (RH)±10% RH for 12 hours minimum; and 40° C.±2° C. at 90% RH±5% RH for 72 hours minimum. The PICC devices were additionally subjected to soak conditioning in which they were submerged in a 0.9% saline solution held at a temperature of 37±2° C. for a minimum of 2 hours. The catheter shaft of each such preconditioned device was tested to determine the tensile strength, modulus, secant modulus, and elongation (strain at peak force) of the devices.

A second test group (Group 2) of 40 PICC devices was manufactured and subjected to sterilization and thermal conditioning in the same manner as Group 1 and was then subjected to accelerated aging to achieve an equivalence of 6 months of natural aging (referred to herein as accelerated aging conditioning). The accelerated aging process included storing the PICC devices for a minimum of 28 days at 50° C. and ambient relative humidity. The aged devices were subjected to soak conditioning, as previously described. The catheter shaft of each device was tested to determine the tensile strength, modulus, secant modulus, and elongation (strain at peak force) of the devices. The results for both Group 1 (identified as T=0, to indicate a lack of accelerated aging) and Group 2 (identified as T=6 Mo. AA, to indicate 6 months of accelerated aging) are provided in Table 7.

TABLE 7

| Test Group | Tensile Strength (lbf) | Elastic Modulus (psi) | Secant Modulus (psi) | Elongation (%) |
|---|---|---|---|---|
| 1: T = 0 | 8.5 ± 0.4 | 1174 ± 55 | 1268 ± 59 | 267 ± 15 |
| 2: T = 6 Mo. AA | 9.5 ± 0.6 | 1311 ± 67 | 1450 ± 90 | 267 ± 15 |

Example 8

A test group (Group 3) of 40 PICC devices according to the specifications of Example 6 were assembled, sterilized, and thermal conditioned. A further test group (Group 4) was subjected to the same conditioning as Group 3, and was additionally subjected to six-month accelerated aging conditioning.

Both Group 3 and Group 4 were subjected to the soaking condition, and were then locked with 70% ethanol for 60 minutes with a tolerance of +15/−0 minutes. Specifically, one of the female luer connectors was coupled with a 10-mL syringe that was filled with 70% ethanol. The syringe was used to flush and prime one lumen of the catheter shaft with the 70% ethanol. Without removing the syringe from the female luer connector, the distal end of the catheter was folded over and pinched with a binder clip to clamp the shaft shut. The syringe was then removed and immediately replaced with a male luer lock cap. The binder clip was then removed from the distal end of the catheter shaft. The catheter was then submerged again in the 0.9% saline bath at 37±2° C. for a period of 60 minutes (+15/−0 minutes). The catheter was then removed again from the 0.9% saline bath. The male luer lock cap was removed and immediately replaced with a 10-mL syringe filled with 0.9% saline at 37±2° C. The syringe was then used to flush the catheter shaft and subsequently removed. At the conclusion of the ethanol lock and flush, each sample was placed back into the saline soak at 37±2° C. for a recovery period of 60 minutes (+15/−0 minutes). The test PICC devices were then subjected to power injection, as described below, at the end of the recovery period.

One testing procedure verified compliance of the PICC devices with power injection specifications, per ISO 10555-1. These tests subjected the catheters to pressures at or above that which they would see under normal use conditions and confirmed their resistance to leaking or bursting after numerous rounds of power injections.

Power injection for the T=0 samples (Group 3) was performed using Visipaque warmed to approximately 37° C. with a viscosity of 11.8 cP+/−0.3 cP. If not within range, deionized water or additional contrast media (Visipaque) was added to adjust viscosity range of power injection fluid. Power injection for the 6-month AA samples (Group 4) was performed using a glycerin solution heated to 37±2° C. with a viscosity of 11.8 cP+/−0.3 cP. Similarly, if viscosity was not within range, additional glycerin or deionized water was added to adjust range.

Group 3 and Group 4 were subjected to preconditioning, as described above, including ethanol locking followed by a recovery period of 60 minutes+15/−0 minutes in the saline bath. Upon termination of the recovery period for each catheter, the catheter was removed from the saline bath and one of the luer connectors was coupled with power injection testing equipment. The equipment then delivered a 120 mL bolus of the viscous fluid (11.8 cP+/−0.3 cP solution, either Visipaque for Group 3 or glycerin for Group 4) at a rate of 5 mL/sec through a single lumen of the catheter. The catheter was then decoupled from the equipment and returned to the 0.9% saline bath at 37° C. and soaked overnight. At the end of each overnight soaking period, each catheter underwent another ethanol lock, flush, 60 minutes+15/−0 minutes recovery period in the saline bath, followed immediately by a single power injection of a 120 mL bolus of viscous fluid, and was then returned to the bath for another overnight soaking. This procedure was repeated for ten days total, thus resulting in 800 total power injections: 400 power injections for Group 3 (40 catheters for 10 days) and 400 for Group 4 (40 catheters for 10 days). For each of the 800 power injections, no leak or burst events were observed (as also discussed with respect to Example 11, below).

Example 9

During power injection, no section of the implantable length of the catheter should swell more than twice the catheter labeled size (e.g., 5 French, in the present example). The extent of swelling a catheter displays is directly related to pressure, wall thickness, and material modulus characteristics. Power injectable PICC devices, such as certain varieties that have received FDA clearance in the U.S., have been established with acceptable OD swelling characteristics. For example, a 5 French power injectable catheter sold by CR Bard under the designation 5 French Triple Lumen PowerPICC® HF has been shown, in clinical use, to have acceptable swelling characteristics under power injection use pressures. That catheter is indicated for use in power injections up to 5 cc/sec (5 mL/sec). Therefore, a comparison can be made between the test catheters of the present example and the 5 FR PowerPICC HF with respect to OD swell.

When comparing the factors that dictate OD swell during injection the following points can be made: (1) outer wall thickness for the present test PICC devices is substantially the same as the power-injectable outer wall of the 5 FR TL PowerPICC HF, (2) both catheters are trimmable designs provided with 55 cm of implantable length, (3) both catheters experience use pressures from injections with contrast media up to 5 cc/sec, (4) both catheters are made of compliant polyurethane materials.

With similar design dimensions for lumen area, length, and wall thickness, and injection pressures for both up to 5 cc/sec, a factor that could lead to differing OD swell performance between the 5 FR TL PowerPICC HF and the samples of the present example is modulus. Due to this, a modulus comparison between the material of the 5 FR TL PowerPICC HF and that of the test PICCs is sufficient to prove acceptable swelling performance of the test PICCs. If the test catheters have an elastic modulus that is greater than that of the Bard 5 FR TL PowerPICC HF then the OD swell of the test catheters will be acceptable for power injection Five test catheters, as well as the shafts of five 5 FR TL PowerPICC HF, were tested. The results are provided in Table 8, below.

TABLE 8

| Catheter Shafts | Elastic Modulus (psi) | Secant Modulus (psi) |
|---|---|---|
| Test PICC (5) | 1219 ± 37 | 1320 ± 45 |
| PowerPICC (5) | 1007 ± 51 | 1076 ± 114 |

Based on the moduli results seen above, the present test catheters should swell no more than the Bard 5 FR TL PowerPICC HF and thus have an OD swell suitable for power injection.

Example 10

Another testing procedure assessed stability of the distal tip of the catheters during power injection. A stable catheter tip during power injections is desirable, as an oscillating tip can, for example, damage the vasculature. During power injection procedures, a PICC line is susceptible to unstable oscillations, also be referred to as tip whipping, which can lead to damage to the vasculature, tip dislodgement, and/or malposition of the catheter. Tip whipping occurs when the thrust force from power injection exceeds the buckling stiffness within a section of tubing anchored at a single point.

A further test group (Group 5) of 40 PICC devices according to the specifications of Example 6 were assembled, sterilized, and subjected to thermal and soak conditioning, as previously described. The PICC devices were then tested for stability length. Stability length refers to the length at which unstable oscillations of a cantilevered catheter will begin during power injection. Measuring a stability length of the catheter shaft, or the length at which an unsupported, cantilevered end of the shaft begins whipping, can provide important information pertaining to the likelihood for tip whipping and malposition of the catheter tip when positioned within the vasculature of the patient. In particular, the greater the stability length, the less prone a particular catheter design will be to tip whipping.

Stability length testing involved coupling one extension leg of the PICC device to power injection apparatus. A distal end of the catheter sheath was then inserted through an elastomeric septum and advanced until at least a 15-centimeter length of the catheter shaft extended from the septum. The distal length of the catheter sheath was thus unsupported, or was cantilevered from its contact with the septum. The distal end of the catheter sheath and the septum were then submerged into a heated bath of deionized water held at a temperature of 37° C. A power injection of deionized water was then delivered through the extension leg at a delivery rate of 5.8 mL/sec. The use of deionized water at the specified delivery rate achieves the same thrust at the distal tip of the catheter as would contrast media delivered at 5.0 mL/sec. As the power injection proceeded, the catheter shaft was slowly drawn through the septum to reduce the unsupported length of the catheter shaft until the catheter stopped whipping or flailing. The unsupported length at which flailing discontinued is the stability length of the PICC device. Testing of the Group 5 PICC devices in the foregoing manner revealed a mean stability length of the catheter shaft of 12.1±0.4 centimeters.

Stability length is affected by modulus, lumen area, and area moment of inertia, with greater values leading to greater stability lengths for cantilevered tubes (e.g., cylindrical catheter shafts). While there is no generally accepted minimum mean stability length for power injectable catheters, as previously noted, the PICC devices have a greater modulus when compared to that of the Bard 5 FR TL PowerPICC HF catheter discussed in Example 9, above. Accordingly, the stability length of the Group 5 PICC devices likely exceeds that of the Bard 5 FR TL PowerPICC HF catheter and is a further indication of the suitability of the PICC devices for power injection.

Example 11

A variety of tests were conducted to confirm the strength and soundness of the bonds of the assembly (which bonds were previously described in detail). Some of the tests further confirmed the strength, alcohol resistance, and resilience of the siliconized polycarbonate polyurethane components-particularly the catheter shaft and extension tubes.

Some of the tests were conducted on the 40 PICC assemblies of test Group 1 and the 40 PICC assemblies of test Group 2, as described in Example 7 above. As previously noted, the PICC assemblies of test Group 1 were subjected to sterilization and thermal conditioning, and the PICC assemblies of test Group 2 were additionally subjected to six-month accelerated aging conditioning. All PICC assemblies were subjected to soak conditioning prior to testing.

For each PICC assembly of Group 1 and Group 2, a portion of the catheter sheath was cut and tested for tensile strength, modulus, and ultimate elongation, as previously described in Example 7 and detailed in Table 7. Each PICC assembly was further cut into additional pieces for further tensile strength testing. In particular, one of the extension legs was cut from each PICC assemblies, thus leaving a partial assembly that included the remaining extension leg, the junction hub, and a proximal portion of the catheter shaft. The female luer connector was then cut from each of said remaining extension legs, such that the partial assembly included a portion of an extension tube at its proximal end and a portion of the catheter shaft at its distal end, with each of said extension tube and catheter shaft portions remaining connected to the junction hub.

Each partial assembly was then tested for tensile strength. The extension tube portion was clamped in a first set of grips, the catheter sheath portion was clamped in a second set of grips, and then one of the first and second sets of grips was then pulled away (e.g., in an opposite direction) from the other of the first and second sets of grips until failure was achieved to determine the ultimate tensile strength of the assembly. This tested, inter alia, the strength of the bonds between the extension tube and the junction hub and between the junction hub and the catheter shaft. The results of this test are as follows:

TABLE 9

| | Shaft-to-Extension Tensile Strength Group 1; N = 40 (T = 0) | Shaft-to-Extension Tensile Strength Group 2; N = 40 (T = 6 Month AA) |
|---|---|---|
| Average | 11.1 lbf | 10.0 lbf |
| Std. Dev. | 1.0 lbf | 1.2 lbf |
| Min. | 8.8 lbf | 7.3 lbf |
| Max. | 13.6 lbf | 12.0 lbf |

For each extension leg that was cut from the PICC assemblies of Groups 1 and 2, the luer connector was secured in a fixture that was held by the first set of grips and the extension tube was clamped in the second set of grips. The luer connector and the extension tube were then pulled in opposite directions. This tested, inter alia, the bond strength between the luer and the extension tube. The results are as follows:

TABLE 10

| | Luer-to-Ext. Leg Tensile Strength Group 1; N = 40 (T = 0) | Luer-to-Ext. Leg Tensile Strength Group 2; N = 40 (T = 6 Month AA) |
|---|---|---|
| Average | 19.2 lbf | 19.0 lbf |
| Std. Dev. | 1.4 lbf | 0.99 lbf |
| Min. | 15.9 lbf | 17.1 lbf |
| Max. | 23.5 lbf | 21.1 lbf |

In addition, leak tests were performed, which demonstrated the solidarity of the overmolded bonds. The test confirmed that for positive pressures of no less than 43.5 psi, no water leaked from any of the bonds. Positive pressure tests using air at the elevated pressure also confirmed resistance to leakage, and likewise imply that under lower levels of negative pressure (such as would be present during aspiration), the bonds prevent external air from being entrained into the PICC.

All samples passed leak tests in the dry state following sterilization (EO) and thermal conditioning (TC). A total of 298 samples were leak tested in a soaked condition with 118 of the 298 being cyclic kink conditioned (described further below with respect to Example 12) and 40 of the 298 undergoing 10-day power injection with 10-day EtOH locking, as described above with respect to Example 8, prior to leak testing. All samples passed the ISO 10555-1 hydraulic leak test.

For PICC devices that were subjected to the 6-Month Accelerated Aging conditioning, a total of 58 samples were tested in a soaked condition with 40 of the 58 undergoing 10-day power injection with 10-day EtOH locking, as described above with respect to Example 8, prior to leak testing. All samples passed the ISO 10555-1 hydraulic leak test.

The assemblies were also tested for hydraulic burst pressure. The burst pressures were compared with the usage pressures (i.e., pressures encountered during power injection) to confirm that the highest power injection usage pressures encountered during testing were well below the burst pressure. Stated otherwise, burst pressure exceeded the peak pressure present in catheter at maximum flow conditions during power injection (use pressure). That is, burst testing was performed to ensure the PICC devices can withstand extreme use and injection pressures at maximum flow rates. Table 11 summarizes test data for assembly burst pressures. This table identifies various conditioning to which the PICC devices of each test group were subjected prior to testing. In particular, in Table 11, "EO" represents ethylene oxide sterilization, "TC" represents temperature conditioning, and "Soak" represents soak conditioning, as previously described with respect to Example 7. Further, the "10-Day Power Injection" and "EtOH (ethanol) Lock" conditioning are as described previously with respect to Example 8. "Cyclic Kink" is discussed below with respect to Example 12, and "Lipid Lock" is discussed below with respect to Example 13. Group 3 and Group 4 in the two final columns of Table 11 are as previously described with respect to Example 8.

TABLE 11

Burst Pressure

| Conditioning | Group A<br>N = 40<br>EO, TC, Soak | Group B<br>N = 40<br>EO, TC, Soak,<br>Cyclic Kink | Group 3; N = 40<br>(T = 0)<br>EO, TC, Soak,<br>Lipid Lock, 10-<br>Day Power<br>Injection, EtOH<br>Lock | Group 4; N = 40<br>(T = 6 Month AA)<br>EO, TC, 6-Month<br>AA, Soak, 10-Day<br>Power Injection,<br>EtOH Lock |
|---|---|---|---|---|
| Average (Median) | 289 psi (289 psi) | 291 psi (290 psi) | 289 psi | 288 psi |
| Std. Dev. | 2 psi | 2 psi | 2 psi | 2.5 psi |
| Min. | 279 psi | 288 psi | 284 psi | 283 psi |
| Max. | 292 psi | 296 psi | 294 psi | 296 psi |

For each set of conditioning, the PICC devices—or, specifically, the fluid paths thereof—exhibited high burst pressures, thus indicating their suitability for use in power injection, even after alcohol locking events. Indeed, regardless of the preconditions to which the fluid paths of the PICC devices were subjected—even including multiple ethanol locking events, followed by recovery periods (as previously described)—the PICC devices were operable at pressures up to 180, 190, 200, 210, 220, 230, 240, 250, 260, 270, 280, or even 285 psi.

Figure 9:
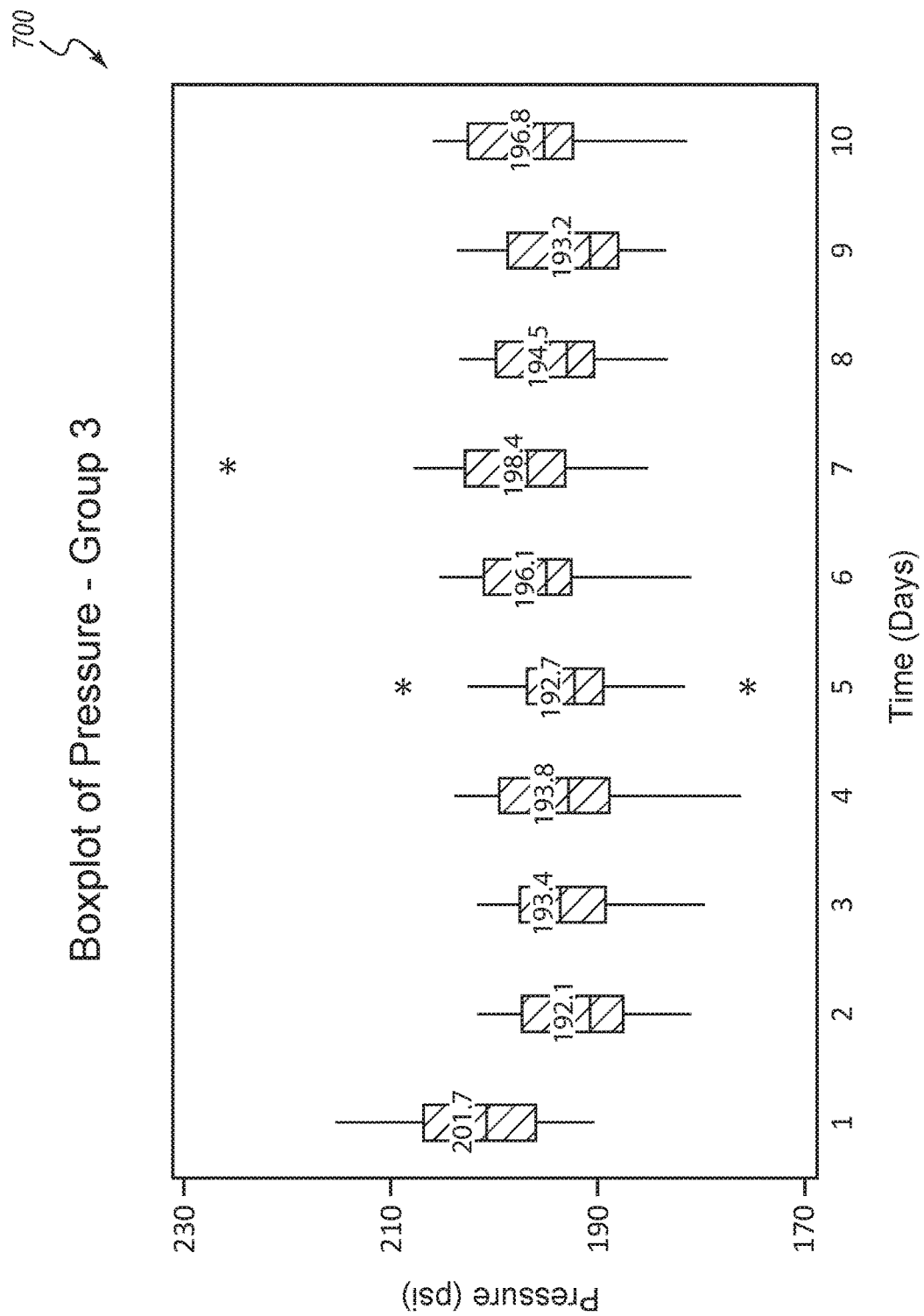
FIG. 9 is a plot of average operational pressures experienced by a group of 40 PICC catheters such as that depicted in FIG. 7 during power injection events over a 10-day period, wherein each catheter was alcohol locked and allowed to recover for a one-hour recovery period prior to each power injection.
Figure 10:
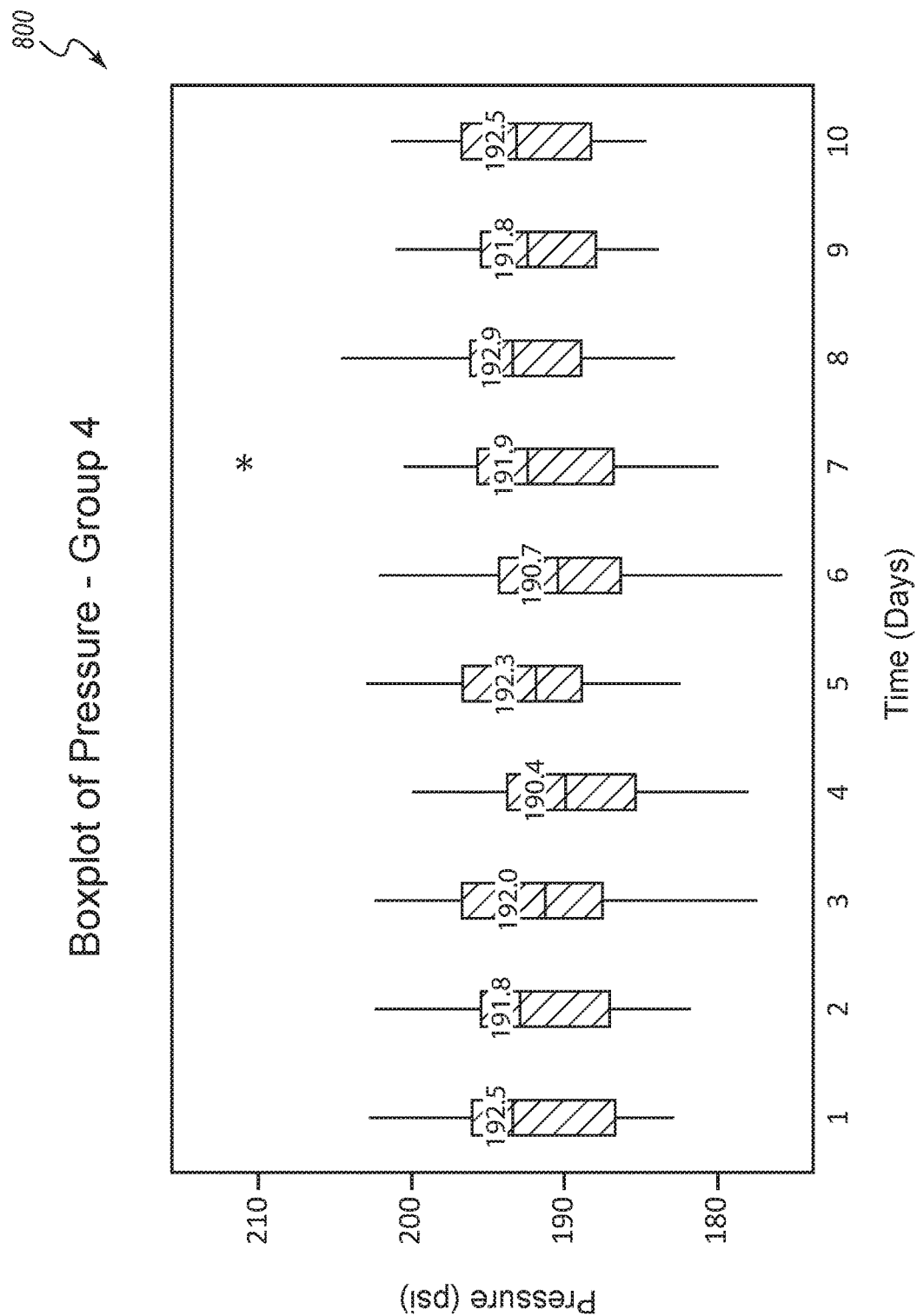
FIG. 10 is a plot of average operational pressures experienced by a different group of 40 PICC catheters, such as that depicted in FIG. 7 and which had been subjected to 6-month accelerated aging conditioning, during power injection events over a 10-day period, wherein each catheter was alcohol locked and allowed to recover for a one-hour recovery period prior to each power injection.

Usage pressures during power injection are as shown in Table 12 below. The usage pressures, as measured on a day-to-day basis, are plotted in FIGS. 9 and 10. In FIG. 9, plot 700 is a box plot of the data gathered from the 40 PICC devices of Group 3 of Example 8. In FIG. 10, plot 800 is a box plot of the data gathered from the 40 PICC devices of Group 4 of Example 8.

TABLE 12

Power Injection Usage Pressure

|  | Group 3; N = 400<br>(T = 0) | Group 4; N = 400<br>(T = 6 Month AA) |
|---|---|---|
| Average (Median) | 195 psi | (192 psi) |
| Std. Dev. | 7 psi | 5 psi |

TABLE 12-continued

Power Injection Usage Pressure

|  | Group 3; N = 400<br>(T = 0) | Group 4; N = 400<br>(T = 6 Month AA) |
|---|---|---|
| Min. | 176 psi | 176 psi |
| Max. | 226 psi | 211 psi |

The usage pressure is defined as the peak pressure encountered during the course of a power injection. As can be seen in each of FIGS. 9 and 10, the usage pressures did not vary greatly from one day to the next. Indeed, for test Group 3 (FIG. 9), the maximum and minimum average usage pressures vary by no more than 5 percent. For test Group 4 (FIG. 10), the maximum and minimum average usage pressures vary by no more than 1.5 percent. In various embodiments, the usage pressure of a catheter from one day to another—or stated otherwise, after at least one overnight period that includes at least one alcohol lock and recovery period sequence—is no greater than, for example, 1, 2, 3, 4, 5, or 10 percent. Moreover, the usage pressures do not reveal any apparent degradation of the PICC devices over time or due to repeated alcohol locking events and repeated power injections.

Table 13 below compares the burst pressures to the usage pressures (i.e., burst pressure−max use pressure) for the two groups (Group 3 and Group 4).

TABLE 13

Burst Pressure - Max Usage Pressure

|  | Group 3; N = 40<br>(T = 0) | Group 4; N = 40<br>(T = 6 Month AA) |
|---|---|---|
| Average (Median) | 86 psi | 93 psi |
| Std. Dev. | 8 psi | 6 psi |
| Min. | 64 psi | 76 psi |
| Max. | 101 psi | 102 psi |

Thus, the burst pressure far exceeds the max use pressure encountered during testing. Use pressures appear to be consistent and reveal slightly higher pressures on day one in most cases. Burst pressures remained consistent across all groups, regardless of conditioning. Average and median burst values do not appear to be affected by power injection, ethanol locking, cyclic kink conditioning (explained below), or 6-month accelerated aging when compared to a baseline burst of sterilization, thermal, and soak conditioning. The PICC devices were not negatively affected by a worst-case simulated use conditioning regime.

Burst performance and acceptability was determined by subtracting the maximum use pressure, observed in a catheter throughout 10 power injections, from the burst value measured in the same catheter sample. A total of 40 data points were collected for distributional analysis, and revealed a normal distribution well above the acceptance criteria, with a mean difference of 86 psi for T=0 samples and 93 psi for T=6-month accelerated aging samples.

These test results demonstrate the capability of the PICC devices to withstand extreme use, including 10 power injections at max flow rate of 5 cc/sec and, prior to each such injection, intraluminal locking of ethanol for 1 hour (with a 1 hour recovery period) preceding the injection. The PICC devices are capable of sustained use at the elevated pressures associated with power injections. For example, the PICC devices are capable of sustaining injection pressures of up to 180, 190, 200, 210, 220, 230, 240, 250, 260, or 270 psi without leaking or bursting, even after repeated alcohol lock events.

Moreover, as is well known, increasing the catheter length increases the operating pressure. Because the burst pressures for these 57.0 centimeter PICC devices are so much higher than their usage pressures, it should be possible to increase the length substantially beyond 57.0 centimeters, which could be advantageous, for example, for larger patients (e.g., bariatric patients). Stated otherwise, the tests demonstrate that in additional embodiments, the PICC device, which can be power injectable before and after ethanol locking, can have an effective length greater than 57 centimeters.

Example 12

Kink diameter was measured for 40 PICC devices constructed in accordance with Example 6 and subjected to sterilization, thermal, and soak conditioning, as described in Example 7. Kink diameter refers to the diameter at which the catheter shaft will kink. That is, at the kink diameter and at diameters smaller than the kink diameter, the catheter shaft will kink, whereas the catheter shaft will not kink at diameters greater than the kink diameter. The results are provided in Table 14.

TABLE 14

| Kink Diameter; N = 40 | |
|---|---|
| Average | 1.24 cm |
| Std. Dev. | 0.08 cm |
| Min. | 0.97 cm |
| Max. | 1.37 cm |

Testing of cyclic kink was also performed. The purpose of this procedure was to simulate stresses from extreme use in the clinic and verify that the catheter shaft can withstand kinking that may occur during dressing changes. This testing likewise demonstrates flexural fatigue tolerance, as cyclic kink conditioning places both tensile and compressive stresses upon the sample and simulates device manipulation anticipated for one year of use. A group of 118 samples were kinked 365 times per sample near the zero mark at the catheter junction (i.e., at a position adjacent to the junction hub). Samples were burst tested following cyclic kink to assess any material damage.

Cyclic kink is intended to simulate dressing changes, during which the catheter may be manipulated and folded for cleaning skin near the insertion site. This would typically occur near the 0 mark towards the proximal end of the shaft tubing. Typical dressing changes occur every 7 days with respect to PICC line maintenance. This yields approximately 26 dressing changes in a six-month period and approximately 52 dressing changes over the course of a year. However, a "worst-case" assessment for a one-year period may be performed by assuming line manipulation daily. Accordingly, cyclic kink was performed with 365 cycles prior to assessing leak and burst of the PICC line.

In this procedure, the catheter shaft is folded over at a position near the junction hub until a kink is observed. The catheter shaft is then unfolded back to the straight position. This process was repeated 365 times for each sample. Thereafter, the PICC assemblies were tested for air or hydraulic leakage at a minimum of 43.5 psi, in manners such as previously described. A sample size of 118 PICC devices was evaluated. All 118 passed this cyclic kinking test without any leakage.

Durability of the extension leg tubing was similarly evaluated. A group of 40 samples underwent 1095 cycles of clamping per extension leg, using the device thumb clamp, prior to burst testing.

Catheter durability testing conditions extension legs with 1095 cycles of clamping via device thumb clamp. This conditioning exposes test samples to typical handling for a year of use. A problematic leak from clamp conditioning would only be possible if the clamps weakened the material to a point that the burst pressure dropped below the power injection (at 5 cc/sec) use pressure. Results of the extension leg burst testing are provided in Table 15. The results clearly demonstrate that extension leg tubing was not damaged below acceptable performance following clamp conditioning.

TABLE 15

| Ext. Leg Burst; N = 40 | |
|---|---|
| Conditioning | EO, TC, Clamp Conditioning, Soak |
| Average | 582 psi |
| Std. Dev. | 14 psi |
| Min. | 551 psi |
| Max. | 608 psi |

Example 13

The PICC devices can be used to accommodate total parenteral nutrition (TPN) therapy and thereby be exposed to a variety of chemical agents including amino acids, sugars, lipids, and electrolytes. For example, PICCs are frequently used with pediatric patients to whom TPN is administered via the PICC. This is true for numerous conditions, including, for example short bowel syndrome.

The most common parenteral nutrition fat source for lipid emulsions used in the United States is soybean oil. G. L. Fell et al., "Intravenous Lipid Emulsions in Parenteral Nutrition," Adv Nutr, 2015. Furthermore, common fat emulsions such as Intralipid, Omegaven, SMOFlipid, and Clinolipid are supplied with lipid concentrations at either 10% or 20% in emulsion. Fell et al.

Adult patient dosing for triglycerides consists of a maximum 3 g triglycerides per kilogram of body weight per day. Baxter Healthcare CORP specifies an allowable supplementation of up to 70% of the maximum adult dosage for triglycerides with Intralipid 20% (a 20% soybean oil lipid emulsion). Assuming an average body weight of 70 kg in an adult patient, the maximum daily dose of soybean oil based Intralipid 20% would be 735 mL per day.

On average, acute care parenteral nutrition has a duration of 10-14 days. J. Mirtallo et al., "Safe Practices for Parenteral Nutrition," Journal of Parenteral and Enteral Nutrition, vol. 28, no. 6, 2004. Upper injection rates of lipid emulsions are established based on patient fat elimination and have been set at a maximum of 500 mL per 5 hours in adult patients using Intralipid. Given the maximum daily dose and maximum infusion rate, a PICC line would be exposed to a 20% lipid emulsion (most likely soybean oil) for 7.35 hours per day and 102.9 total hours for 14 days of parenteral nutrition.

A soybean oil concentration five times that of Intralipid 20% was used to establish compatibility of the PICC devices with lipids. Due to this, time of exposure was reduced by an amount less than fivefold. Thus, the PICC devices had an intraluminal exposure to 100% soybean oil for a minimum duration of 20 hours and 35 minutes.

To assess the effects of lipids on the properties of the siliconized polycarbonate polyurethane, a single lipid conditioning step was performed on power injection samples prior to the first ethanol lock and power injection. Lipid conditioning consisted of locking the PICC sample with 100% soybean oil and soaking in 0.9% saline for a minimum of 20.58 hours. Burst testing was used to characterize any deleterious effects from lipid, ethanol, and power injection conditioning and to verify functional capabilities following lipid conditioning.

Performing intraluminal exposure to 100% soybean oil for a minimum duration of 20.58 hours provided a clinically relevant condition for evaluating lipid interaction with the siliconized polycarbonate polyurethane material.

Conditioning was as follows. The lumen to be power injected was primed with 100% soybean oil using a 10 mL syringe. Without removing the syringe from the luer, the distal end of the catheter shaft was folded and pinched with a binder clip to clamp shut. The syringe was removed and immediately replaced with a male luer lock cap. The samples were placed back into the 0.9% saline soaking bath at 37° C. The samples were allowed to soak while locked with soybean oil for a minimum of 20 hours and 35 minutes. Both lumens of each of the PICC device samples were flushed with deionized water prior to subsequent conditioning and testing.

The results of tests that involved lipid preconditioning, such as just described, are shown with respect to the PICC devices of Group 3 in Tables 11, 12, and 13 and in plot 700 of FIG. 9. For Group 3, which was subjected to lipid conditioning prior to all power injection testing, no leaks were observed during 400 total power injections. Moreover, all 40 test units passed air leak tests. Additionally, it is noted that the power injections took place after the lipid exposure, thus showing that ethanol locking could be used for removal of lipid occlusions in the PICC devices.

Example 14

Numerous PICC devices according to Example 6 were manufactured and tested for biocompatibility. Testing was performed under appropriate ISO 10993 standards (including ISO 10993-1:2009, -3:2014, -4:2009, -4:2017, -5, -6:2016, -10:2010, -11:2006, -12:2012, -17:2008, -17:2012, and -18:2013); ISO 14971:2007/(R) 2010; and European Union Medical Device Directive 93/42/EEC. The devices were determined to be non-cytotoxic, non-sensitizing, non-irritating, non-toxic, non-pyrogenic, and non-hemolytic; to have no statistical difference from a reference marketed PICC catheter (specifically, the 5 French, triple lumen PowerPICC HF discussed above) with respect to activation of the complement system and to have similar clotting times to the marketed PICC catheter. The devices were also determined to be non-thrombus forming via dog thrombogenicity testing. Overall, the PICC devices were determined to be a non-irritant and biocompatible.

Some of the sample PICC devices underwent an extractable/leachable analysis per ISO 10993-18:2013. The device was extracted in triplicate by full immersion in purified water and isopropyl alcohol (IPA) at 50° C. for 72 hours. The water extract was analyzed by inductively coupled plasma-mass spectrometry (ICP/MS) and cold vapor atomic absorption spectroscopy (CVAAS) for metals, and gas chromatography-mass spectrometry (GC/MS) analyzing for volatiles, semi-volatiles, and a limited set of non-volatile organics. The IPA extract was analyzed by GC/MS methods for semi-volatile organics. Using these analytical chemistry techniques, the extractable/leachable compounds were identified and quantified to determine the chemical dose to the user. The compounds identified were then assessed in a Toxicological Risk Assessment.

In particular, the Toxicological Risk Assessment was performed on the following compounds identified in the chemistry extractable/leachables testing: barium (CAS 7440-39-3)/barium sulfate (CAS 7727-43-7), boron, caprolactam (CAS 105-60-2), di(2-ethylhexyl) phthalate (CAS 117-81-7), din-butyl phthalate (CAS 84-74-2), n-octadecane (CAS 593-45-3), silicon/silica dioxide, and strontium. The intent of the risk assessment was to closely examine the toxicological hazard of the identified compounds and to evaluate and address any risks associated with the biological endpoints of subacute/subchronic and chronic toxicity, genotoxicity and carcinogenicity for adult and pediatric populations. Tolerable intake (TI), tolerable exposure (TE), and margins of safety (MOS) were calculated according to the ISO 10993-17:2008: *Biological evaluation of medical devices—Part 17: Establishment of allowable limits for leachable substances*. An MOS greater than one is indicative of a low toxicological hazard for the evaluated substance. Based on the calculated margins of safety in the Toxicological Risk Assessment, it was determined that the likelihood of adverse effects from the device is considered low for all compounds. The assessment also indicated that subacute/subchronic and chronic toxicity, genotoxicity, and carcinogenicity from the use of device are not expected. Additionally, results within the Toxicological Risk Assessment demonstrate the device's toxicological safety is supported in neonates weighing down to 2.3 kg (based on the lowest calculated MOS value in neonates for silicon/silica dioxide).

That is, the toxicological risk assessment tests demonstrated that the PICC devices are safe in neonates weighing down to 2.3 kg. Moreover, although the toxicological risk assessment tested for presence of barium and barium sulfate (due to potential leaching of the compounded barium sulfate from the catheter material), the lower safety limit was based on the lowest calculated MOS value in neonates for silicon/silica dioxide. This indicates that the catheter material performs well at retaining the compounded barium sulfate, or stated otherwise, leaches this component (which constitutes 30% of the total weight of the material) in very small amounts.

These results are particularly impressive given the tests were performed on a 5 French catheter, for which there is significantly more material present than there would be for a smaller diameter (e.g., lower flow rate) catheter, and likewise, a larger surface area from which leaching may take place.

Further, the silicon/silica dioxide that leached from the test PICC devices, which was the limiting leachate upon which the 2.3 kg value was based, may have been due to the presence of lubricants used during extrusion. As mentioned elsewhere herein, certain embodiments of the siliconized polycarbonate polyurethane can be extruded without the presence of such lubricant additives. Stated otherwise, the siliconized polycarbonate polyurethanes of which one or more of the catheter shaft, the junction hub, and/or the extension tubes are formed may be devoid of lubricant additives. In certain of such embodiments, the 5 French PICC devices, which can contain, e.g., up to 30 wt % barium sulfate, can be safe for use in neonates weighing less than 2.3 kg.

V. Further Examples

Example 15

Three additional siliconized polycarbonate polyurethanes were prepared, with varying formulations and polymerization processes, and their hardness evaluated. The test formulations and the hardness of each are summarized in Table 16.

Test Formulation 3 comprises a different composition from that of Test Formula 1, and was prepared via substantially the same process as that used for Formula 2. In particular, the preheated PDMS and MDI were added to a common vessel and mixed for 5 minutes. The preheated PHMCD was then added to the mixture, which was then mixed for an additional 5 minutes. Finally, the preheated BDO was added and the mixture was mixed for approximately one additional minute.

For each of Test Formulations 1, 2, and 3, upon completion of the mixing, the mixture was poured onto baking sheets and cured overnight in an oven at 230° F. After curing, the material was removed from the baking sheets and mechanically ground into particles having an average particle size less than about 10 millimeters. The particles were then dried in a desiccant dryer and subsequently stored for subsequent use. A quantity of the particles was then molded into test plaques for hardness testing, which was evaluated according to ASTM D2240 using a Check-Line HPSA manual durometer.

TABLE 16

| Test Formulation # | Measurement Description | Polycarbonate diol (PHMCD) Soft Segment | PDMS | MDI Hard Segment | BDO | Hardness (Shore A Durometer) |
|---|---|---|---|---|---|---|
| 1 | weight (g) | 1921.8 | 507.3 | 1716.8 | 443.2 | 97 |
|  | individual wt % | 41.9 | 11.1 | 37.4 | 9.7 |  |
|  | wt % of polyol component | 79.1 | 20.9 | n/a | n/a |  |
|  | soft segment wt % vs. hard segment wt % | 52.9 |  | 47.1 |  |  |
| 2 | weight (g) | 1919.6 | 508.9 | 1713.8 | 448.3 | 97 |
|  | individual wt % | 41.8 | 11.1 | 37.3 | 9.8 |  |
|  | wt % of polyol component | 79.0 | 21.0 | n/a | n/a |  |
|  | soft segment wt % vs. hard segment wt % | 52.9 |  | 47.1 |  |  |
| 3 | weight (g) | 2071.4 | 546.1 | 1577.6 | 389.6 | 90 |
|  | individual wt % | 45.2 | 11.9 | 34.4 | 8.5 |  |
|  | wt % of polyol component | 79.1 | 20.9 | n/a | n/a |  |
|  | soft segment wt % vs. hard segment wt % | 57.1 |  | 42.9 |  |  |

For each of Test Formulations 1, 2, and 3, the polycarbonate polyol, polysiloxane polyol, isocyanate, and chain extender where the same as those described above with respect to Example 1. Moreover, each reactant was preheated, as described with respect to Example 1.

For Test Formulation 1, the preheated PHMCD, PDMS, and MDI were added to a common vessel and mixed for 5 minutes, without separately controlling the heat. That is, the reaction was permitted to occur on its own, with the heat increasing due to the exothermic nature of the reaction. The preheated BDO was then added to the mixture and the mixture was mixed for approximately one additional minute.

Test Formulation 2 comprises the same general composition as Test Formula 1, but was prepared via a different process. In particular, the preheated PDMS and MDI were added to a common vessel and mixed for 5 minutes. The preheated PHMCD was then added to the mixture, which was then mixed for an additional 5 minutes. Finally, the preheated BDO was added and the mixture was mixed for approximately one additional minute.

Example 16

Test plaques were molded from the siliconized polycarbonate polyurethanes of each of Test Formulations 1, 2, and 3 of Example 15, above. Smaller samples were cut from each of these test plaques and were soaked in 70% ethanol for 46 hours at 37° C. The swelling of the siliconized polycarbonate polyurethane samples, as measured by % increase in mass, was around 5-7% for each test formulation. This result was compared with the same testing of a commercially available aromatic polyether polyurethane, PELLETHANE® 2363-65D, which showed 16% swell, and a commercially available aliphatic polyether polyurethane, QUADRAFLEX® ALE (QFLEX-ALE-91A-B30-003-002), which showed 41% swell, as summarized in Table 17 below. Whereas Test Formulations 1, 2, and 3 and the PELLETHANE were formed directly into the test plaques, without being physically compounded with other additives, the QUADRAFLEX material was compounded with 30 wt % barium sulfate and colorant.

TABLE 17

| Material | % Swell in 70% Ethanol |
|---|---|
| Test Formulation 1 | 5.5 |
| Test Formulation 2 | 5.5 |
| Test Formulation 3 | 6.3 |
| PELLETHANE | 16.2 |
| QUADRAFLEX | 40.5 |

Although there was little difference in swelling between Test Formulations 1 and 2, other factors indicate that the "three-shot" process for Test Formulation 2 may be preferable for materials intended for use in PICC devices. For example, the modulus of the Test Formulations 1 and 2 materials were each tested before and after ethanol exposure (70% EtOH), and while the moduli were very similar prior to exposure, the Formulation 2 material was slightly higher after exposure. Further, the test plaques molded for both materials showed some layering and delamination, which was marginally less pronounced for the three-shot, Test Formulation 2 material. Without being bound by theory, this appeared to indicate a better distribution of the PDMS material for Test Formulation 2.

Example 17

PICC devices having the components and physical dimensions set forth in Example 6, above, can be assembled from materials of the formulations set forth in Table 18, below. Methods of forming such materials can proceed, for example, in any of the manners disclosed herein. Some amount of variability from the target values set forth in Table 18 is contemplated. For example, the concentration of barium sulfate can be present in an amount of 30±2 wt %, and the amounts of the remaining components can be adjusted accordingly. Stated otherwise, in some instances, a target amount of the barium sulfate is 30 wt % with a tolerance of ±2 wt %.

TABLE 18

| | | Siliconized Polycarbonate Polyurethane | | | | | | Final Material | | | |
|---|---|---|---|---|---|---|---|---|---|---|---|
| Component | Measurement Description | Polycarbonate diol Soft Segment | PDMS Soft Segment | MDI Hard Segment | BDO Hard Segment | Isocyanate Index | Hardness (Shore Durometer) | Siliconized Polycarbonate Polyurethane (wt %) | Barium Sulfate (wt %) | Colorant (wt %) | GLYCOLUBE™ VL (wt %) |
| Catheter Shaft | individual wt % | 50.4 | 5.6 | 34.8 | 9.2 | 1.05 | 97A | 68.75 | 30.0 | 1.25 | 0 |
| | wt % of polyol component | 90.0 | 10.0 | n/a | n/a | | | | | | |
| | soft segment wt % vs. hard segment wt % | 56.0 | | 44.0 | | | | | | | |
| Extension Tubes | individual wt % | 50.4 | 5.6 | 34.8 | 9.2 | 1.05 | 97A | 99.9 | 0 | 0.1 | 0 |
| | wt % of polyol component | 90.0 | 10.0 | n/a | n/a | | | | | | |
| | soft segment wt % vs. hard segment wt % | 56.0 | | 44.0 | | | | | | | |
| Junction Core | individual wt % | 44.5 | 5.0 | 39.3 | 11.2 | 1.023 | 71D | 99.7 | 0 | 0 | 0.3 |
| | wt % of polyol component | 89.9 | 10.1 | n/a | n/a | | | | | | |
| | soft segment wt % vs. hard segment wt % | 49.5 | | 50.5 | | | | | | | |
| Junction Cover | individual wt % | 61.8 | 6.9 | 25.8 | 5.6 | 1.022 | 81A | 99.2 | 0 | 0.5 | 0.3 |
| | wt % of polyol component | 90.0 | 10.0 | n/a | n/a | | | | | | |
| | soft segment wt % vs. hard segment wt % | 68.7 | | 31.3 | | | | | | | |

Example 18

PICC devices having the components and physical dimensions set forth in Example 6, above, can be assembled from materials of the formulations set forth in Table 19, below. Methods of forming such materials can proceed, for example, in any of the manners disclosed herein. Some amount of variability from the target values set forth in Table 19 is contemplated. For example, the concentration of barium sulfate can be present in an amount of 30±2 wt %, and the amounts of the remaining components can be adjusted accordingly. Stated otherwise, in some instances, a target amount of the barium sulfate is 30 wt % with a tolerance of ±2 wt %.

TABLE 19

| Component | Measurement Description | Polycarbonate diol (Soft Segment) | PDMS (Soft Segment) | MDI (Hard Segment) | BDO (Hard Segment) | Isocyanate Index | Hardness (Shore Durometer) | Siliconized Polycarbonate Polyurethane (wt %) | Barium Sulfate (wt %) | Colorant (wt %) | GLYCOLUBE™ VL (wt %) |
|---|---|---|---|---|---|---|---|---|---|---|---|
| Catheter Shaft | individual wt % | 50.4 | 5.6 | 34.8 | 9.2 | 1.05 | 97A | 68.75 | 30.0 | 1.25 | 0 |
| | wt % of polyol component | 90.0 | 10.0 | n/a | n/a | | | | | | |
| | soft segment wt % vs. hard segment wt % | 56.0 | | 44.0 | | | | | | | |
| Extension Tubes | individual wt % | 50.4 | 5.6 | 34.8 | 9.2 | 1.05 | 97A | 99.9 | 0 | 0.1 | 0 |
| | wt % of polyol component | 90.0 | 10.0 | n/a | n/a | | | | | | |
| | soft segment wt % vs. hard segment wt % | 56.0 | | 44.0 | | | | | | | |
| Junction Core | individual wt % | 44.5 | 5.0 | 39.3 | 11.2 | 1.035 | 70D | 99.7 | 0 | 0 | 0.3 |
| | wt % of polyol component | 89.9 | 10.1 | n/a | n/a | | | | | | |
| | soft segment wt % vs. hard segment wt % | 49.5 | | 50.5 | | | | | | | |
| Junction Cover | individual wt % | 61.8 | 6.9 | 25.8 | 5.6 | 1.035 | 80A | 99.2 | 0 | 0.5 | 0.3 |
| | wt % of polyol component | 90.0 | 10.0 | n/a | n/a | | | | | | |
| | soft segment wt % vs. hard segment wt % | 68.7 | | 31.3 | | | | | | | |

For the extruded components of the present example, as well as other extruded components disclosed herein, lubricants and/or release agents, such as GLYCOLUBE®, fumed silica, etc., were omitted from the overall formulation of the material. Such omissions can also be possible for the molded components. Stated otherwise, in some embodiments, no lubricants or release agents are added to the material, whether at the polymerization stage, during compounding, and/or during extrusion or molding. Rather, the siliconized polycarbonate polyurethane can be sufficiently lubricious on its own, or without assistance from other materials, to achieve extrusion (e.g., without pellets adhering together so as to clog the hopper) or molding.

This property of the materials can be a significant advantage. Lubricants (including release agents) and/or other additives (e.g., nucleating agents) generally contribute to the toxicity and/or thrombogenicity of an extrudate or molded component. Accordingly, elimination of such materials from, for example, the catheter shaft and/or from the extension tubes can enhance the performance of the devices formed therefrom (PICCs, midlines, PIVs, etc.) within the body of a patient.

By way of illustration, in Example 12, above, the PICC devices on which the toxicological risk assessment was performed included GLYCOLUBE® in the extension tubes and fumed silica in the extension tubes and the catheter shaft. Even with these additives, the amount of leachates was very small, demonstrating that the material is advantageously resistant to leaching. Indeed, the finding that the 5 French PICC device is suitable for use with neonates weighing down to 2.3 kg is remarkably good. Nevertheless, the limiting factor in determination was the presence of silicon/silica dioxide. Omission of GLYCOLUBE® and fumed silica from the extruded materials should render similarly constructed PICC devices suitable for use with even smaller patients, or stated otherwise, in patients weighing less than 2.3 kg.

Example 19

To assess relative thrombus accumulations, fifteen (15) 5 French, dual-lumen catheter shafts having the dimensions and configurations of those described in Example 2 were extruded from a siliconized polycarbonate polyurethane of the formulation set forth in Table 20, below. The polycarbonate polyol, polysiloxane polyol, isocyanate, and chain extender, as well as the method of material preparation, were the same as those described above with respect to Example 1. These are identified herein as the Group I catheter shafts. For comparison, fifteen (15) 5 French, dual-lumen catheter shafts having the dimensions and configurations of those described in Example 2 were extruded from a material having approximately 69 wt % of a catheter-grade aliphatic polyether polyurethane sold under the trademark QUADRAFLEX®, which is available from Biomerics, which was compounded with 30 wt % barium sulfate and approximately 1 wt % colorant. These are identified herein as the Group II catheter shafts. Fifteen (15) catheter shafts were also cut from fifteen (15) commercially available 5 French, dual-lumen power injectable PICC catheter assemblies sold under the trademark ARROW®, available from Teleflex of Wayne, Pa., which are identified herein as the Group III catheter shafts.

TABLE 20

Group I Material

Siliconized Polycarbonate Polyurethane

| Measurement Description | Polycarbonate diol Soft Segment | PDMS Soft Segment | MDI Hard Segment | BDO Hard Segment | Isocyanate Index | Hardness (Shore Durometer) | Final Material Siliconized Polycarbonate Polyurethane (wt %) | Barium Sulfate (wt %) | Colorant (wt %) | Lubricant additives (e.g., fumed silica) (wt %) |
|---|---|---|---|---|---|---|---|---|---|---|
| individual wt % | 50.3 | 5.6 | 34.9 | 9.2 | 1.047 | 97A | 69.12 | 29.62 | 1.25 | 0 |
| wt % of polyol component | 90.0 | 10.0 | n/a | n/a | | | | | | |
| soft segment wt % vs. hard segment wt % | 55.9 | | 44.1 | | | | | | | |

Notably, no fumed silica, GLYCOLUBE®, or any other lubricants and/or release agents were used in the formulation. As previously discussed, such materials can increase the thrombogenicity of an extrudate or molded component. Accordingly, omission of such materials from the formulation can enhance the antithrombogenic performance (e.g., reduce the thrombogenicity) of medical devices formed therefrom (PICCs, midlines, PIVs, implants of any suitable variety, etc.) within the body of a patient.

A total of 15 blood loop experiments were performed. In each experiment, three blood circulation test loops were used, with each test loop including a water bath at 37° C., a receptacle containing fresh heparinized bovine blood with autologous radiolabeled platelets positioned in the water bath, and a section of tubing having opposite ends inserted into the bovine blood and an intermediate portion passing through a roller pump to continuously circulate blood through the tubing. In each test loop, an end of a catheter shaft was inserted to permit blood flow about the outer surface of the shaft, thus modeling insertion of the catheter within the vasculature of a patient. The inserted tip of the catheter shaft sample was sealed with epoxy to eliminate luminal blood ingress and to focus the study on the catheter external surface. Each test loop contained one sample from either Group I, Group II, or Group III. At the end of each experiment, the catheter shafts were explanted from the tubing, rinsed with saline, and placed in a gamma counter for thrombus quantification.

Each experiment consisted of three independent blood circulation test loops (each corresponding to one of Group I, Group II, or Group III) each circulating blood from the same animal. This enabled simultaneous comparisons without cross-over effects. Blood from fifteen (15) different animals was tested.

Experimental parameters are set forth in Table 21.

TABLE 21

Experimental Parameters

| | |
|---|---|
| Heparin concentration | 0.75 U/ml |
| Internal diameter of test loop tubing | 0.25 (6.4 mm) inches |
| Blood flow rate | 200 ml/min |
| Experiment time | 60-120 min |
| Number of replications (N)* | 15 |

Raw data from the 15 experiments are provided in table 22.

*Blood from a different animal was used in each replication (i.e., a unique blood lot per replicate).

TABLE 22

Thrombus Accumulation

Radiation counts per minute (cpm)

| Expt. # | Group I (siliconized polycarbonate polyurethane) | Group II (QUADRAFLEX®) | Group III (ARROW®) |
|---|---|---|---|
| 1 | 2299 | 6276 | 6482 |
| 2 | 994 | 1845 | 513 |
| 3 | 1571 | 1388 | 665 |
| 4 | 1945 | 2923 | 242 |
| 5 | 492 | 3510 | 1201 |
| 6 | 627 | 1157 | 899 |
| 7 | 3991 | 2869 | 3674 |
| 8 | 18882 | 18027 | 16557 |
| 9 | 82 | 576 | 751 |
| 10 | 156 | 1354 | 579 |
| 11 | 1030 | 2351 | 2589 |
| 12 | 105 | 1941 | 2207 |
| 13 | 2073 | 1773 | 2619 |
| 14 | 2803 | 7826 | 1450 |
| 15 | 845 | 1938 | 1117 |

Figure 11:
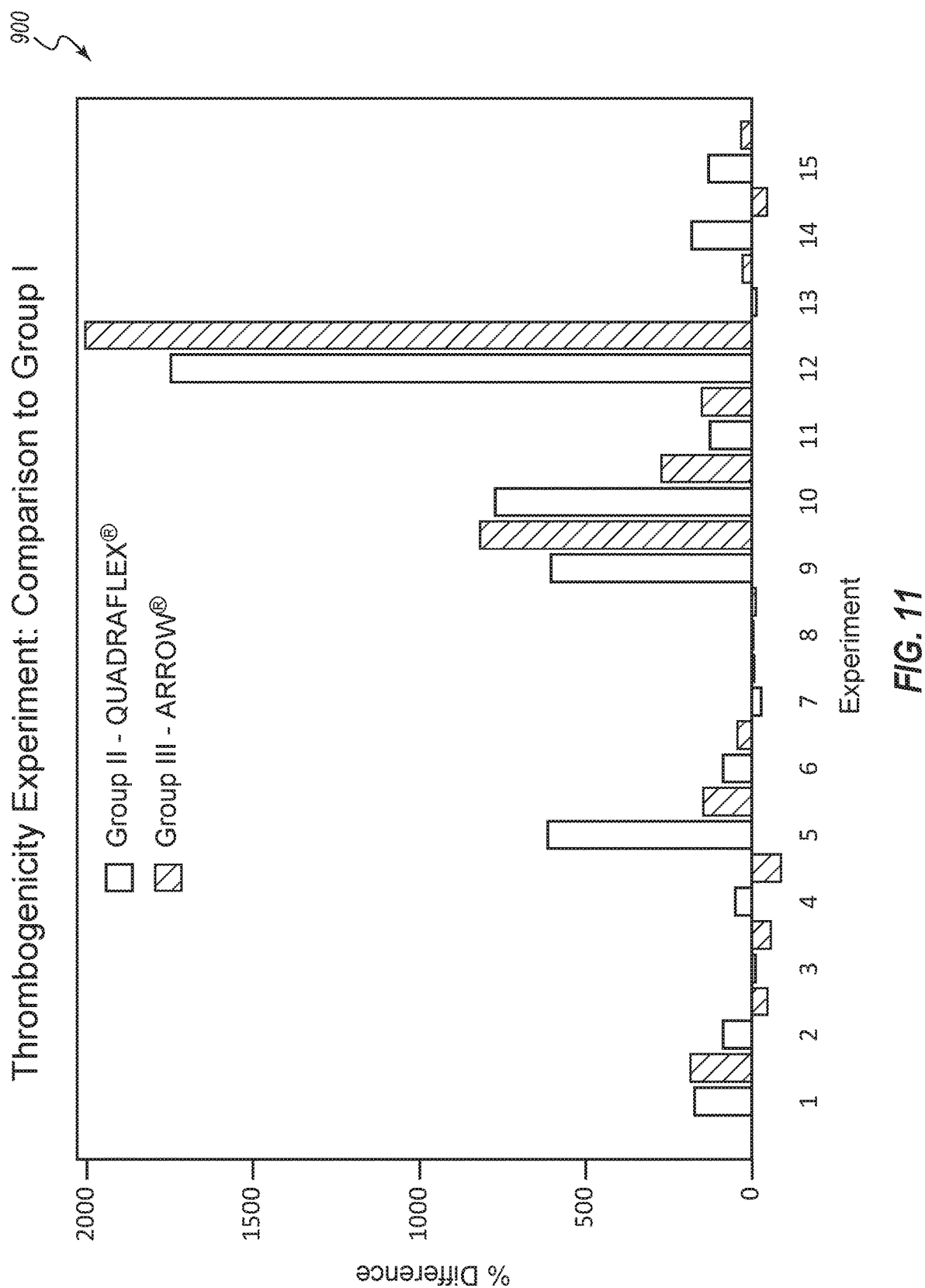
FIG. 11 is a plot comparing thrombus formation on the exterior surfaces of three different types of catheter shafts for fifteen separate experimental runs.

Distributions for all groups were non-normal. Due to inherent blood differences between experiments, study variability was high. However, this variability is determined appropriate, as it would also be expected in a human patient-to-patient situation. In FIG. 11, plot 900 compares the results of Group II and Group III to the results of Group I within each experiment.

Evaluating percent increase with respect to Group I at the experiment level shows Group II having 300% more thrombus accumulation, on average, and Group III having 227% more thrombus accumulation, on average. Moreover, statistical significance is found when comparing mean and median values for Group I and Group II. Due to distribution skew and outliers, it can be desirable to use a non-parametric test. Since the data is paired, a two-sample, two-tailed Wilcoxon signed rank test can be used to demonstrate that the distribution of Group I is significantly lower than the distribution of Group II (p-value=0.015), with Group II reporting a median value that is 88% greater than that of Group I. Group III reports a median increase of 17% when compared to the median of Group I; however, the distribution of Group I is not significantly lower than the distribution of Group III (p-value=0.71).

Thus, the catheter shafts of Group I, which are formed from a siliconized polycarbonate polyurethane in accordance with one embodiment of the present disclosure, outperformed both the QUADRAFLEX® catheter shafts of Group II (which are of a variety used in known commercial power injectable PICCs) and the ARROW® catheter shafts of Group III in the foregoing in vitro blood loop study evaluating thrombus accumulation. Statistical significance is shown in comparison of median values between Group I and Group II, with the Group I shafts reporting a lower median value for thrombus accumulation. Based on these results, it is expected that catheters formed of the siliconized polycarbonate polyurethane of the formulation set forth in Table 20 (Group I) will have less thrombus accumulation in clinical use, as compared with at least competitive PICC products employing shafts such as those formed of QUADRAFLEX® (Group II). Moreover, thrombus accumulation performance of Group I is at least as good as the commercial power injectable PICC products (ARROW®) associated with Group III.

Example 20

To evaluate surface energies, four (4) 5 French, dual-lumen catheter shafts having the dimensions and configurations of those described in Example 2 were extruded from a siliconized polycarbonate polyurethane (SPCPU) of the formulation set forth in Table 20, above. Thus, the SPCPU catheter shafts were substantially the same as those of Group I in Example 19. Further, a commercially available 5 French PowerPICC® catheter was obtained.

Testing of the catheter shafts proceeded as follows. A catheter tube sample was secured to a horizontal stage located within the field of view of a microscope camera. A single drop of water was deposited onto the surface of the catheter tube sample in a sessile drop arrangement. A magnified image of the sessile drop was captured for measurement analysis. Drops were deposited and measured at three or four different positions along each catheter tube. Contact angle was determined by measuring the angle formed between the liquid-solid interface and the liquid-vapor interface. Results of the test are provided in Table 23.

TABLE 23

Contact Angle

| Group | Siliconized Polycarbonate Polyurethane Sample # | | | | PowerPICC® |
| --- | --- | --- | --- | --- | --- |
|  | 1 | 2 | 3 | 4 | 1 |
| 1st Location | 57° | 70° | 89° | 71° | 93° |
| 2nd Location | 69° | 65° | 87° | 80° | 99° |
| 3rd Location | 56° | 78° | 70° | 87° | 105° |
| 4th Location | — | — | — | 91° | — |

The mean contact angle for the SPCPU catheter tubes was 74.6 degrees, with a standard deviation of 11.3, and the mean contact angle for the PowerPICC® catheter tube was 99 degrees, with a standard deviation of 4.9. Based on the foregoing results, the SPCPU surface appears to be less hydrophobic, which is believed to be indicative of a greater surface free energy. Indeed, anecdotally, it was much more difficult to keep a drop of water on the surface of the small tube of the PowerPICC® device than it was to keep them on the SPCPU tubes. Many water droplets ran off of the PowerPICC® surface, such that the values shown in Table 23 are likely on the low end of the actual population distribution. Conversely, placing a drop of water on the SPCPU tubes was relatively easy, which would seem to correspond well with the smaller contact angle data shown in Table 23.

According to Xu et al., Proteins, Platelets, and Blood Coagulation at Biomaterial Interfaces, *Colloids Suf B Biointerfaces,* 2014 Dec. 1, 124:49-68, the surface energy of a biomaterial can play a significant role in the extent to which the biomaterial activates thrombosis. The process of biomaterial-associated thrombosis consists of both platelet-mediated reactions (platelet adhesion, activation, and aggregation) and coagulation of blood plasma. Plasma protein interactions with surfaces trigger the coagulation cascade of blood, resulting in thrombus production and formation of a fibrin clot. Coagulation involves a series of self-amplifying, zymogen-enzyme conversions which are traditionally grouped as the intrinsic and extrinsic pathways.

Xu et al. note that the initiation of the intrinsic pathway is generally referred to as contact activation, which mainly involves coagulation factor XII (FXII, Hageman factor) and three other proteins. The traditional biochemistry of contact activation shows that FXII is converted to the active enzyme form FXIIa, which can be produced by at least three different biochemical reactions. One of these reactions is known as contact autoactivation, in which FXII interacts with a procoagulant surface and converts into the active enzyme form FXIIa through autoactivation due to a conformational structural change upon the binding of FXII to the surface. This conversion then leads to subsequent coagulation cascade reactions.

Xu et al. state that FXII contact activation is surface-dependent. Without being bound by theory, it is believed that the surface energy, or wettability, of a biomaterial can have a significant effect on the extent to which the biomaterial causes contact activation of FXII. Since common observations clearly show that plasma coagulation is more efficient in activation by contact with anionic or hydrophilic surfaces, it was at one time concluded that contact autoactivation of FXII was more specific for hydrophilic surfaces than hydrophobic surfaces, based on traditional biochemistry theory. However, experimental evidence has demonstrated that hydrophobic and hydrophilic surfaces have nearly equal autoactivation properties in neat-buffer solution of FXII. That is, contact activation of FXII is not specific to anionic hydrophilic surfaces in neat buffer. In fact, contact activation of FXII in neat-buffer solution exhibits a generally parabolic profile when scaled as a function of surface energy. Nearly equal activation is observed at both extremes of activator water wettability (e.g., nonwetting and perfectly wetting), and falls through a broad minimum where the water contact angle $\theta$ is in a range of from about 55 degrees to about 75 degrees. Relatively low activation is also present just outside of either end of the foregoing range. The recited contact angle range corresponds to a surface energy T within a range of from about 20 dyn/cm (at $\theta$=about 75 degrees) to about 40 dyn/cm (at $\theta$=about 55 degrees), and energies just outside of either end of this range also exhibit relatively low activation.

Accordingly, biomaterials that exhibit a water contact angle $\theta$ within a range of from about 55 degrees to about 75 degrees, or even from about 50 degrees to about 80 degrees, may exhibit superior antithrombogenic properties, in that they are less prone to activate thrombi. This corresponds with the observations of the catheter shafts in this present Example 20 and in Example 19 (discussed above). In particular, under the given experimental conditions, the mean contact angle for the SPCPU catheter tubes of the present Example 20 (which were formed identically to the catheter shafts of Example 19) was 74.6 degrees. This falls within the 55-degree-to-75-degree water contact angle range for minimum FXII contact activation identified in Xu et al. Without being bound by theory, the surface energy of the catheter shafts of Group I may at least partially account for their reduced thrombus production. Further, it has been observed that hydrophilic surfaces lacking ionic charge and lacking strong hydrogen-bonding groups can be desirable for minimizing platelet activation. See Griggs et al., *Thrombosis* and Thromboembolism Associated with Intravascular Catheter Biomaterials, Medical Device Evaluation Center, Salt Lake City, Utah, U.S.A., May 20, 2008; see also Samuel Eric Wilson, Vascular Access: Principles and Practice, p. 60.

In various embodiments, catheter tubes formed from any of various embodiments of siliconized polycarbonate polyurethanes disclosed herein can exhibit a water contact angle within a range of from about 55 degrees to about 75 degrees, from about 55 degrees to about 70 degrees, from about 55 degrees to about 65 degrees, from about 55 degrees to about 60 degrees, from about 60 degrees to about 75 degrees, from about 60 degrees to about 70 degrees, from about 60 degrees to about 65 degrees, from about 65 degrees to about 75 degrees, from about 65 degrees to about 70 degrees, from about 70 degrees to about 75 degrees, from about 50 to about 80 degrees, from about 50 to about 65 degrees, from about 50 to about 60 degrees, from about 50 to about 55 degrees, from about 65 degrees to about 80 degrees, from about 70 to about 80 degrees, or from about 75 to about 80 degrees, or of about 50 degrees, about 55 degrees, about 60 degrees, about 65 degrees, about 70 degrees, about 75 degrees, or about 80 degrees. In various embodiments, catheter tubes formed from various embodiments of siliconized polycarbonate polyurethanes disclosed herein can have a surface energy within a range of from about 20 dyn/cm to about 40 dyn/cm, from about 20 dyn/cm to about 35 dyn/cm, from about 20 dyn/cm to about 30 dyn/cm, from about 20 dyn/cm to about 25 dyn/cm, from about 25 dyn/cm to about 40 dyn/cm, from about 25 dyn/cm to about 35 dyn/cm, from about 25 dyn/cm to about 30 dyn/cm, from about 30 dyn/cm to about 40 dyn/cm, from about 30 dyn/cm to about 35 dyn/cm, or from about 35 dyn/cm to about 40 dyn/cm, from about 15 dyn/cm to about 45 dyn/cm, from about 15 dyn/cm to about 30 dyn/cm, from about 15 dyn/cm to about 25 dyn/cm, from about 15 dyn/cm to about 20 dyn/cm, from about 30 dyn/cm to about 45 dyn/cm, from about 35 dyn/cm to about 45 dyn/cm, or from about 40 dyn/cm to about 45 dyn/cm, or of about 15, 20, 25, 30, 35, 40, or 45 dyn/cm. In various of the foregoing embodiments, the catheter tubes can have an outer diameter of 4 French, 5 French, or 6 French. Further, in various of the foregoing embodiments, the siliconized polycarbonate polyurethane material may be free of additive lubricants, release agents, nucleating agents, etc. (e.g., fumed silica) that might otherwise lead to greater thrombogenicity. In various of the foregoing embodiments, the catheter shafts can be incorporated into catheter assemblies such as previously described, which may be used as PICC catheters or, in further instances, as power injectable PICC catheters such as previously described. In still further instances, the catheters (e.g., power injectable PICCs) can be ethanol-lock resistant or compatible, such as previously described.

As should be apparent from the foregoing disclosure, including various combinations or compilations of the foregoing examples, certain materials described herein are extremely well suited for use in medical devices, and particularly in power injectable PICCs. In particular, the present inventors have discovered that specific varieties of polycarbonate polyols, polysiloxane, and isocyanates can be reacted in specific manners, including in relative amounts that fall within very particular ranges, to achieve siliconized polycarbonate polyurethanes that simultaneously meet numerous performance objectives for power injectable PICCs. Certain of the properties exhibited by the resultant materials are even unexpected.

PICCs formed of such materials are advantageously capable of repeatedly operating at elevated power injection pressures without performance degradation. The material is thus strong and resilient. Further, the PICCs are capable of repeatedly being ethanol- or alcohol-locked. The PICCs also exhibit impressive resistance to thrombus formation, which may at least in part result from having a surface energy that appears to fall within an ideal or desirable range for non-activation of factor XII. Further still, the PICCs prevent leaching to such a degree that even relatively large diameter PICCs are suitable for use in very small pediatric patients, including neonates down to 2.3 kg in some instances, and in even smaller or lighter patients in further instances.

In some embodiments, a PICC device, such as any of those described above, is included with a kit. In addition to the PICC device, the kit may include an introducer. The kit may include instructions for use, which may provide directions with respect to any of the processes disclosed herein. The instructions for use can specifically recommend or direct a user to employ alcohol locking, as described herein. For example, in the event of infection and/or lipid occlusion, the instructions may direct that alcohol locking for a clinically effective period, including any of those previously disclosed (e.g., one hour), sufficient to resolve the issue, and can further instruct that the user wait for a recovery period, including any of those previously disclosed (e.g., one hour), prior to, for example, power injecting via the catheter. In various embodiments, the kit—and, in particular, the instructions for use thereof—can be approved of or authorized by a regulating body of a particular jurisdiction. For example, the kit, and the instructions for use thereof, may be approved of or authorized by the Food and Drug Administration of the United States of America and/or may comply with the regulations of other jurisdictions, such as by qualifying for CE marking in the European Union.

In certain examples discussed above, alcohol locking for a clinically effective treatment period of one hour (e.g., 60 minutes+15/−0 minutes) and a recovery period of one hour (e.g., 60 minutes+15/−0 minutes) are discussed. Other suitable periods are contemplated. For example, in various embodiments, alcohol locking may be conducted for clinically effective treatment periods of no less than about 10, 15, 20, 25, 30, 35, 40, 45, 50, 55, or 60 minutes. In other or further embodiments, the PICC devices may be suitable for use after such alcohol locking events (e.g., after the alcohol has been flushed from the device) after a recovery period of no less than about 10, 15, 20, 25, 30, 35, 40, 45, 50, 55, or 60 minutes.

Although much of the foregoing discussion is devoted to catheters, and in particular, PICC catheters, the materials and other teachings of the present disclosure are more generally applicable. These may be applicable, or suitable for use in, a variety of other medical devices and catheters, for example. The medical devices, or components thereof, can be at least partially formed of one of more varieties of the material. The medical devices may include, for example, any suitable variety of medical catheter, vascular access device, central access device, midline catheter, IV catheter, implantable port, etc. For example, any of a variety of medical devices other than catheters may be manufactured from any of the materials disclosed herein, including in any of the examples or in any other portion of the present disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claims 1, 2, or 3, with these separate dependencies yielding three distinct embodiments; claim 5 can depend from any one of claims 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. An alcohol-resistant siliconized polycarbonate polyurethane formed from reactants that comprise:
   a polycarbonate polyol having a structure according to formula (I):

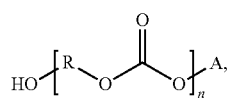

(I)

wherein R is selected from a linear or branched, substituted or unsubstituted $C_1$-$C_{24}$ alkylene group; A is selected from hydrogen (H) or R'OH; R' is selected from a linear or branched, substituted or unsubstituted $C_1$-$C_{24}$ alkylene group and is either the same as or different from R; and n is an integer from 2 to 30;
   a polysiloxane having a structure according to formula (IV):

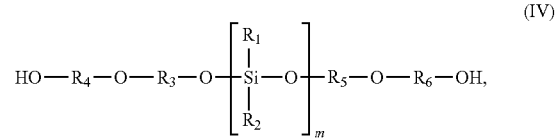

(IV)

wherein $R_1$ and $R_2$ are independently selected from a linear $C_1$-$C_6$ alkyl group or a hydrogen group, $R_3$ and $R_5$ are independently selected from a C1-C12 alkylene group, $R_4$ and $R_6$ are independently selected from a C1-C8 alkylene group, and m is an integer from 2 to 30;
   an isocyanate; and
   a chain extender,
   the siliconized polycarbonate polyurethane comprising:
      a hard segment;
      a soft segment that comprises the polysiloxane in an amount of from 5 wt % to 15 wt %; and
      an isocyanate index of from 1.01 to 1.06.

2. The siliconized polycarbonate polyurethane of claim 1, wherein the polysiloxane has a number average molecular weight ($M_n$) of from about 925 g/mol to about 1025 g/mol.

3. The siliconized polycarbonate polyurethane of claim 2, wherein the soft segment comprises the polysiloxane in an amount of from 9 wt % to 11 wt %.

4. The siliconized polycarbonate polyurethane of claim 3, wherein the isocyanate index is from 1.03 to 1.06.

5. The siliconized polycarbonate polyurethane of claim 1, wherein the polysiloxane is a carbinol-modified polydimethylsiloxane having a structure according to formula (V):

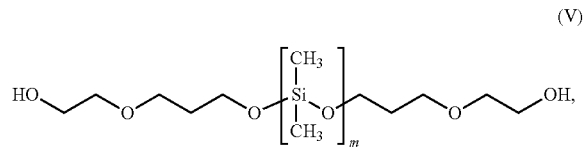

(V)

wherein m is an integer from 2 to 30.

6. The siliconized polycarbonate polyurethane of claim 5, wherein the polysiloxane has a number average molecular weight ($M_n$) of from about 925 g/mol to about 1025 g/mol.

7. The siliconized polycarbonate polyurethane of claim 6, wherein the polycarbonate polyol has a number average molecular weight ($M_n$) of from about 1840 g/mol to about 2200 g/mol.

8. The siliconized polycarbonate polyurethane of claim 7, wherein the isocyanate index is within a range of from 1.03 to 1.06.

9. The siliconized polycarbonate polyurethane of claim 8, wherein the polycarbonate polyol comprises poly(hexamthylene carbonate) diol.

10. The siliconized polycarbonate polyurethane of claim 8, wherein the isocyanate is aromatic.

11. The siliconized polycarbonate polyurethane of claim 1, wherein the hard segment is present in an amount of between 40 wt % to 50 wt % and the soft segment is present in an amount of between 50 wt % to 60 wt %.

12. The siliconized polycarbonate polyurethane of claim 11, wherein the siliconized polycarbonate polyurethane has a Shore A durometer value of between about 96 to about 100.

13. A medical device comprising at least one component that comprises the siliconized polycarbonate polyurethane according to claim 1.

14. The medical device of claim 13, wherein the medical device comprises a peripherally inserted central catheter (PICC) device comprising at least one fluid path that is power injectable.

15. The medical device of claim 14, wherein said at least one fluid path of the PICC device is power injectable after (1) having been subjected to an ethanol locking event for a period sufficient to disinfect said at least one fluid path and (2) having been flushed after the ethanol locking event and permitted to recover for a recovery period.

16. The medical device of claim 15, wherein the recovery period is no less than one hour.

17. The medical device of claim 13, wherein the medical device comprises a peripherally inserted central catheter (PICC) device comprising at least one fluid path that is capable of sustaining injection pressures of up to 180 psi without bursting and without leaking.

18. A kit comprising:
- a catheter comprising at least one component that comprises the siliconized polycarbonate polyurethane according to claim 1; and
- instructions for using the catheter, said instructions providing directions to:
  - introduce alcohol into a lumen of the catheter and maintain the alcohol therein for a clinically effective locking period;
  - flush the alcohol from the lumen of the catheter; and
  - wait for a recovery period after flushing the alcohol from the lumen prior to using the lumen for an injection.

19. The kit of claim 18, wherein the recovery period is at least one hour.

20. The kit of claim 18, wherein a length of a shaft of the catheter that is configured to be introduced into a vasculature of a patient defines a 5 French outer diameter.

21. The kit of claim 20, wherein the instructions for use indicate that the catheter is usable for patients weighing at least 2.3 kg.

22. The kit of claim 21, wherein the alcohol-resistant siliconized polycarbonate polyurethane of the shaft is compounded with a radiopacifier in an amount sufficient to render the shaft visible under radiography when the shaft is within a patient.

23. The kit of claim 22, wherein the radiopacifier comprises barium sulfate.

24. The kit of claim 18, wherein the injection is a power injection.

* * * * *